United States Patent
Mulder

(10) Patent No.: US 7,741,043 B2
(45) Date of Patent: Jun. 22, 2010

(54) CONTROL OF TGFβ SIGNALING BY KM23 SUPERFAMILY MEMBERS

(76) Inventor: Kathleen M. Mulder, 713 W. Elm St., Palmyra, PA (US) 17078-3029

(*) Notice: Subject to any disclaimer, the term of this patent is extended or adjusted under 35 U.S.C. 154(b) by 618 days.

(21) Appl. No.: 11/648,939

(22) Filed: Jan. 3, 2007

(65) Prior Publication Data
US 2007/0122836 A1 May 31, 2007

Related U.S. Application Data

(60) Division of application No. 10/227,988, filed on Aug. 26, 2002, now Pat. No. 7,229,758, which is a continuation-in-part of application No. PCT/US01/06176, filed on Feb. 26, 2001.

(60) Provisional application No. 60/184,843, filed on Feb. 25, 2000.

(51) Int. Cl.
*C12Q 1/68* (2006.01)
(52) U.S. Cl. .............................. 435/6; 530/350
(58) Field of Classification Search ....................... None
See application file for complete search history.

(56) References Cited

FOREIGN PATENT DOCUMENTS

| EP | 1033401 A2 | 9/2000 |
|---|---|---|
| WO | WO 99/51727 | 10/1999 |
| WO | WO 00/55180 | 9/2000 |

OTHER PUBLICATIONS

Dermer, G. Biotechnology vol. 12:320. 1994.*
Chabert et al. Int. J. Cancer vol. 53:837-842. 1993.*
Lucetini, J. The Scientist vol. 18:1-5. 2004.*
Kroese, M. Genetics in Medicine vol. 6:475-480. 2004.*
Database SWALL [Online] Accession No. 088567, Nov. 1, 1998.
Database EMBL [Online] Accession No. AF161511, Feb. 1, 2000.
Database SWALL [Online] Accession No. Q9NQM2, Oct. 1, 2000.
Database SWALL [Online] Accession No. Q9NP97, Oct. 1, 2000.
Database EMBL [Online] Accession No. AF165516, Jul. 21, 2000.
Bowman et al.; Drosophila roadblock and Chlamydomonas LC7: A Conserved Family of Dynein-associated Proteins Involved in Axonal Transport, Flagellar Motility, and Mitosis; The Journal of Cell Biology; vol. 146; No. 1; Jul. 12, 1999 165-179.
Hirokawa; Kinesin and Dynein Superfamily Proteins and the Mechanism of Organelle Transport; Science; vol. 279, Jan. 23, 1998 519-526.
Yue and Mulder; Transforming Growth Factor-β Signal Transduction in Epithelial Cells; Pharmacology and Therapeutics; vol. 91; No. 1; 2001 1-34.
Massagué; TGF-β Signal Transduction; Annu. Rev. Biochem; 1998; 67:753-91.
Hartsough and Mulder; Transforming Growth Factor-β Signaling in Epithelial Cells; Pharmacology and Therapeutics; vol. 75; No. 1; 1997; 21-41.
Wakefield et al.; Distribution and Modulation of the Cellular Receptor for Transforming Growth Factor-Beta; The Journal of Cell Biology; vol. 105; Aug. 1987; 965-975.
Sporn et al.; Some Recent Advantages in the Chemistry and Biology of Transforming Growth Factor-Beta; The Journal of Cell Biology; vol. 105; Sep. 1987; 1039-1045.
Kim et al.; Molecular Mechanisms of inactivition of FGF-β receptors during carcinogenesis; Cytokine & Growth Factors Reviews 11 (2000) 159-168.
Tang et al.; A novel TGFβ receptor-interacting protein that is also a light chain of the motor protein dynein; Mol. Biol Cell; In Press; 2002.
Mátyus, László; Fluorescence resonance energy transfer measurements on cell surfaces. A spectroscopic tool for determining protein interactions; J. Photochem. Photobiol B. Biol., 12 (1992) 323-337.
Hartsough et al.; Altered Transforming Growth Factor β Signaling in Epithelial Cells when Ras Activation is Blocked; The Journal of Biological Chemistry; vol. 271, No. 37; Issue of Sep. 13, 1996 pp. 22368-22375.
Yue and Mulder; Requirement of Ras/MAPK Pathway Activation by Transforming Growth Factor β for Transforming Growth Factor $β_1$ Production in a Smad-dependent Pathway; The Journal of Biological Chemistry; vol. 275, No. 40; Issue of Oct. 6, 2000; pp. 30765-30773.

* cited by examiner

*Primary Examiner*—Heather G Calamita
(74) *Attorney, Agent, or Firm*—Hoffmann & Baron, LLP

(57) ABSTRACT

Methods of identifying therapeutic agents that inhibit, potentiate or mimic the ability of a km23 polypeptide mutant form, or a nucleic acid encoding the mutant form to modulate the signal transduction activity of a growth factor or cytokine are provided. The methods involve treating a cell with a candidate compound so as to alter at least one cell process associated with the TGFβ signaling pathway, and measuring the effect of the candidate on the cell. Further provided are cell and non-cell based methods of screening for a therapeutic agent that inhibits or stimulates the interaction of an altered form of wild-type km23 with a specific binding protein, such as the dynein intermediate chain (DIC), Smad2 or RI and RII TGFβ receptors. These methods involve determining the inhibition or stimulation of a therapeutic candidate on the interaction of the specific binding protein with the km23 altered form. The km23 mutant/altered forms of the methods of the present invention indicate an increased risk of ovarian cancer.

2 Claims, 21 Drawing Sheets

```
hkm23  -80                                  GACAGAAACCTTTGCGCAGGCGCAGAAAG    -52
rkm23 -118 GAAGAAACCCTGACAAGGACACAACGTGAGCAGGTGCTTTGGGCGTCAGGCCTCGTGCCGAATTCGG -52
                                            *   *      * **  *     * ***   *

1   2 ➔
                                                                  ┌─────────┐
                                                                   M   A   E   V    4
hkm23  -51 GCACAGGACTCGCTAAGTGTTCGCTACGCGGGGCTACCGGATCGGTCGGAA ATG GCA GAG GTG  12
rkm23  -51 CACGAGACTCGGCTGAGTGTTGGCGATTCGGAGCTGCTGTGTCTGTCCGAG ATG GCA GAG GTG  12
               **  ***** ****** **  **   * *  * *   **  ***  * **  *** *** *** ***

PKC                  PKC
                  ┌────────┐           ┌────────┐
            5  E   E   T   L   K   R   L   Q   S   Q   K   G   V   Q   G   I   I   21
hkm23      13 GAG GAG ACA CTG AAG CGA CTG CAG AGC CAG AAG GGA GTG CAG GGA ATC ATC  63
rkm23      13 GAG GAA ACA CTC AAG AGG CTT CAG AGC CAG AAA GGA GTG CAG GGC ATC ATC  63
              *** **  *** **  *** **   *   *** *** *** **  *** *** *** **  *** ***

3 ➔
                                                    CK II
                                                ┌────────────┐
           22  V   V   N   T   E   G   I   P   I   K   S   T   M   D   N   P   T   38
hkm23      64 GTC GTG AAC ACA GAA GGC ATT CCC ATC AAG AGC ACC ATG GAC AAC CCC ACC 114
rkm23      64 GTG GTG AAC ACA GAA GGC ATT CCC ATC AAG AGC ACA ATG GAC AAT CCC ACC 114
              **  *** *** *** *** *** *** *** *** *** *** **  *** *** **  *** ***

39  T   T   Q   Y   A   S   L   M   H   S   F   I   L   K   A   R   S   55
hkm23     115 ACC ACC CAG TAT GCC AGC CTC ATG CAC AGC TTC ATC CTG AAG GCA CGG AGC 165
rkm23     115 ACG ACA CAG TAC GCC AAC CTC ATG CAC AAC TTC ATC TTA AAG GCT CGG AGC 165
              **  **  *** **  *** *   *** *** *** *   *** *** *   *** **  *** ***

PKC/CK II
             ┌────────────┐
           56  T   V   R   D   I   D   P   Q   N   D   L   T   F   L   R   I   R   72
hkm23     166 ACC GTG CGT GAC ATC GAC CCC CAG AAC GAT CTC ACC TTC CTT CGA ATT CGC 216
rkm23     166 ACT GTG CGT GAG ATT GAC CCC CAG AAT GAC CTA ACC TTC CTT CGA ATT CGC 216
              **  *** *** **  **  *** *** *** **  **  **  *** *** *** *** *** ***

4 ➔
                PKC
             ┌────────┐
           73  S   K   K   N   E   I   M   V   A   P   D   K   D   Y   F   L   I   89
hkm23     217 TCC AAG AAA AAT GAA ATT ATG GTT GCA CCA GAT AAA GAC TAT TTC CTG ATT 267
rkm23     217 TCC AAG AAA AAT GAA ATT ATG GTG GCA CCA GAT AAA GAC TAT TTC CTG ATT 267
              *** *** *** *** *** *** *** **  *** *** *** *** *** *** *** *** ***
```

FIG. 1A

```
                    90  V   I   Q   N   P   T   E   ^                                          97
hkm23    268 GTG ATT CAG AAT CCA ACC GAA TAA GCCACTCTCTTGGCTCCCTGTGTCATTCCTTAATT   326
rkm23    268 GTG ATT CAG AAT CCA ACT GAA TAA GGCACTGTCTTGGCTTCCTGTGTCATTCCTTAATT   326
             * * * * *   * *  * ** **** ******************* hkm23    327 TAATGCCCCCCAAGAATGTTAATGTCAATCATGTCAGTGGACTAGCACATGGCAGTCGCTTGGAACC   393
rkm23    327 TAATGTCCCCCGAGAATAATAGCGTTAATCATGTCAGTGG----GCACATG-TGGCTGCCTGGAGCC   388
             *** * *    ***********       *****  * hkm23    394 CACTCACACCAATCCAGTGACCGTGTGTGGGCTGGCGGCTCTTCTCCCCCACCAACGGAACCCCTGT   460
rkm23    389 -----ATGCAGACCTTGGCATTG-GTGAAG---GGCAGCTCTGCCCACCCCACCAAGGAGTGCCTCT   446
                  *   *    *  *    *  *    *    * *** *  ****  *  * hkm23    461 GTGCACCAACCTTCCCCAGAGCTCCGGAGCGCCCTCTCCTCACTTCCAGGTTTTGGAGCAAGAGCTT   527
rkm23    447 GATGATC-----CGGTCAGTCCCCAGAAGAGCTCAGTTCTCTCT-CCAGGCTTTGGAATGAGAGCTC   507
              *  *        ***  *   **  *  *   *   * **  **** hkm23    528 GCAGGAAGCCCGCACCCAGCTTCCTTCTGACCTTCAGTTCACTTTGTCGCCCTTGGAGAAAGCTGTT   594
rkm23    508 TTGATAAGCCCACAGCCAGCTTCCTTCTAACCTTCATTTCACTTTGTCCCCCTTGGAAGCTGTTTTT   574
                 ****  *********** *** ******* ******  *  * ** hkm23    595 TTTCTTT--AACTAAAAATAACCAAAATGCTAAAAAAAAAAAAAAAAAA                   641
rkm23    575 GTTTTTTTAAACTAAAAATAACTTCAACCCCAAAAAAAAAAGAAAAAAAAAAAAAA            631
              ** ***  ************  ** *  * *********  *******
```

FIG. 1B

Blot Ab: myc

Blot Ab: HA

SEQUENCE LISTING

<160> NUMBER OF SEQ ID NOS: 23

<210> SEQ ID NO 1
<211> LENGTH: 96
<212> TYPE: PRT
<213> ORGANISM: Homo sapiens

<400> SEQUENCE: 1

Met Ala Glu Val Glu Glu Thr Leu Lys Arg Leu Gln Ser Gln Lys Gly
1               5                   10                  15

Val Gln Gly Ile Ile Val Val Asn Thr Glu Gly Ile Pro Ile Lys Ser
            20                  25                  30

Thr Met Asp Asn Pro Thr Thr Thr Gln Tyr Ala Ser Leu Met His Ser
        35                  40                  45

Phe Ile Leu Lys Ala Arg Ser Thr Val Arg Asp Ile Asp Pro Gln Asn
    50                  55                  60

Asp Leu Thr Phe Leu Arg Ile Arg Ser Lys Lys Asn Glu Ile Met Val
65                  70                  75                  80

Ala Pro Asp Lys Asp Tyr Phe Leu Ile Val Ile Gln Asn Pro Thr Glu
                85                  90                  95

<210> SEQ ID NO 2
<211> LENGTH: 96
<212> TYPE: PRT
<213> ORGANISM: Rattus sp.

<400> SEQUENCE: 2

Met Ala Glu Val Glu Glu Thr Leu Lys Arg Leu Gln Ser Gln Lys Gly
1               5                   10                  15

Val Gln Gly Ile Ile Val Val Asn Thr Glu Gly Ile Pro Ile Lys Ser
            20                  25                  30

Thr Met Asp Asn Pro Thr Thr Thr Gln Tyr Ala Asn Leu Met His Asn
        35                  40                  45

Phe Ile Leu Lys Ala Arg Ser Thr Val Arg Glu Ile Asp Pro Gln Asn
    50                  55                  60

Asp Leu Thr Phe Leu Arg Ile Arg Ser Lys Lys Asn Glu Ile Met Val
65                  70                  75                  80

Ala Pro Asp Lys Asp Tyr Phe Leu Ile Val Ile Gln Asn Pro Thr Glu
                85                  90                  95

<210> SEQ ID NO 3
<211> LENGTH: 721
<212> TYPE: DNA
<213> ORGANISM: Homo sapiens

<400> SEQUENCE: 3
gacagaaacc tttgcgcagg cgcagaaagg cacaggactc gctaagtgtt cgctacgcgg      60
ggctaccgga tcggtcggaa atggcagagg tggaggagac actgaagcga ctgcagagcc     120
agaagggagt gcagggaatc atcgtcgtga acacagaagg cattcccatc aagagcacca     180
tggacaaccc caccaccacc cagtatgcca gcctcatgca cagcttcatc ctgaaggcac     240
ggagcaccgt gcgtgacatc gaccccagga acgatctcac cttccttcga attcgctcca     300
agaaaaatga attatggtt gcaccagata aagactattt cctgattgtg attcagaatc      360
caaccgaata agccactctc ttggctccct gtgtcattcc ttaatttaat gcccccaag      420 aatgttaatg tcaatcatgt cagtggacta gcacatggca gtcgcttgga acccactcac     480

```
accaatccag tgaccgtgtg tgggctggcg gctcttctcc cccaccaacg gaacccctgt    540
gtgcaccaac cttccccaga gctccggagc ccctctcct cacttccagg tttggagca     600 agagcttgca ggaagcccgc acccagcttc cttctgacct tcagttcact ttgtcgccct   660
tggagaaagc tgttttctt taactaaaaa taaccaaat gctaaaaaa aaaaaaaaaa      720 a                                                                    721
```

<210> SEQ ID NO 4
<211> LENGTH: 749
<212> TYPE: DNA
<213> ORGANISM: Rattus sp.

<400> SEQUENCE: 4

```
gaagaaaccc tgacaaggac acaacgtgag caggtgcttt gggcgtcagg cctcgtgccg    60
aattcggcac gagactcccc ggagtgttgg tgattcggag ctgctgtgtc tgtccgagat   120
ggcagaggtg gaggaaacac tcaagaggct tcagagccag aaaggagtgc agggcatcat   180
cgtggtgaac acagaaggca ttcccatcaa gagcacaatg gacaatccca ccacgacaca   240
gtacgccaac ctcatgcaca acttcatctt aaaggctcgg agcactgtgc gtgagattga   300
cccccagaat gacctaacct tccttcgaat tcgctccaag aaaaatgaaa ttatggtggc   360
accagataaa gactatttcc tgattgtgat tcagaatcca actgaataag gcactgtctt   420
ggcttcctgt gtcattcctt aatttaacgt ccccgagaa taatagcgtt aatcatgtca    480
gtgggcacat gtggctgcct ggagccatgc agaccttggc attggtgaag gcagctctg   540 cccacccac caaggagtgc ctctgatgat ccggtcagtc cccagaagag ctcagttctc   600
tctccaggct ttggaatgag agctcttgat gagcccacag ccagcttcct tctaaccttc   660
atttcacttt gtccccttg gaagctgttt ttgttttttt aaactaaaaa taacttcaac   720
cccaaaaaaa aaagaaaaaa aaaaaaaaa                                      749
```

<210> SEQ ID NO 5

<400> SEQUENCE: 5

000                                                                   1

<210> SEQ ID NO 6
<211> LENGTH: 107
<212> TYPE: PRT
<213> ORGANISM: Homo sapiens

<400> SEQUENCE: 6

```
Met Ala Glu Val Glu Glu Thr Leu Lys Arg Leu Gln Ser Gln Lys Gly
1               5                   10                  15

Val Gln Gly Ile Ile Val Val Asn Thr Glu Gly Ile Pro Ile Lys Ser
            20                  25                  30

Thr Met Asp Asn Pro Thr Thr Thr Gln Tyr Ala Ser Leu Met His Ser
        35                  40                  45

Phe Ile Leu Lys Ala Arg Ser Thr Val Arg Asp Ile Asp Pro Gln Asn
    50                  55                  60

Asp Leu Thr Phe Leu Arg Ile Arg Ser Lys Lys Asn Glu Ile Met Val
65                  70                  75                  80

Ala Pro Asp Lys Asp Tyr Phe Leu Ile Val Ile Gln Asn Pro Thr Glu
                85                  90                  95

His Ala Thr Leu Leu Ala Pro Cys Val Ile Pro
```

<210> SEQ ID NO 7
<211> LENGTH: 324
<212> TYPE: DNA
<213> ORGANISM: Homo sapiens

<400> SEQUENCE: 7

```
atggcagagg tggaggagac actgaagcga ctgcagagcc agaagggagt gcagggaatc    60
atcgtcgtga acacagaagg cattcccatc aagagcacca tggacaaccc caccaccacc   120
cagtatgcca gcctcatgca cagcttcatc ctgaaggcac ggagcaccgt gcgtgacatc   180
gacccccaga acgatctcac cttccttcga attcgctcca agaaaaatga aattatggtt   240
gcaccagata aagactattt cctgattgtg attcagaatc caaccgaaca cgccactctc   300
ttggctccct gtgtcattcc ttaa                                          324
```

<210> SEQ ID NO 8
<211> LENGTH: 21
<212> TYPE: DNA
<213> ORGANISM: Artificial Sequence
<220> FEATURE:
<223> OTHER INFORMATION: synthetic primer

<400> SEQUENCE: 8
tgctattcca gttctcccca a    21

<210> SEQ ID NO 9
<211> LENGTH: 21
<212> TYPE: DNA
<213> ORGANISM: Artificial Sequence
<220> FEATURE:
<223> OTHER INFORMATION: synthetic primer

<400> SEQUENCE: 9
atcctctgga gacaccactg t    21

<210> SEQ ID NO 10
<211> LENGTH: 21
<212> TYPE: DNA
<213> ORGANISM: Artificial Sequence
<220> FEATURE:
<223> OTHER INFORMATION: synthetic primer

<400> SEQUENCE: 10
tccacatcct ctcagtctcc g    21

<210> SEQ ID NO 11
<211> LENGTH: 21
<212> TYPE: DNA
<213> ORGANISM: Artificial Sequence
<220> FEATURE:
<223> OTHER INFORMATION: synthetic primer

<400> SEQUENCE: 11
aatgtgccat gaggtctgtt c    21

<210> SEQ ID NO 12
<211> LENGTH: 20
<212> TYPE: DNA
<213> ORGANISM: Artificial Sequence
<220> FEATURE:
<223> OTHER INFORMATION: synthetic primer

<400> SEQUENCE: 12
tgccaggtgc ctgagtatta        20

<210> SEQ ID NO 13
<211> LENGTH: 21
<212> TYPE: DNA
<213> ORGANISM: Artificial Sequence
<220> FEATURE:
<223> OTHER INFORMATION: synthetic primer

<400> SEQUENCE: 13
gatcagattc atgaagggct t        21

<210> SEQ ID NO 14
<211> LENGTH: 21
<212> TYPE: DNA
<213> ORGANISM: Artificial Sequence
<220> FEATURE:
<223> OTHER INFORMATION: synthetic primer

<400> SEQUENCE: 14
caaacgtatg attcatctgc c        21

<210> SEQ ID NO 15
<211> LENGTH: 20
<212> TYPE: DNA
<213> ORGANISM: Artificial sequence
<220> FEATURE:
<223> OTHER INFORMATION: synthetic primer

<400> SEQUENCE: 15
atgctgtgtt atggctgctt        20

<210> SEQ ID NO 16
<211> LENGTH: 21
<212> TYPE: DNA
<213> ORGANISM: Artificial sequence
<220> FEATURE:
<223> OTHER INFORMATION: synthetic primer

<400> SEQUENCE: 16
atttggagat gctgaacgtt g        21

<210> SEQ ID NO 17
<211> LENGTH: 21
<212> TYPE: DNA
<213> ORGANISM: Artificial Sequence
<220> FEATURE:
<223> OTHER INFORMATION: synthetic primer

<400> SEQUENCE: 17
aagcgactgc catgtgctag t        21

<210> SEQ ID NO 18
<211> LENGTH: 21
<212> TYPE: DNA
<213> ORGANISM: Artificial Sequence
<220> FEATURE:
<223> OTHER INFORMATION: synthetic primer

<400> SEQUENCE: 18
tggtttattt gctttcttgt g        21

<210> SEQ ID NO 19
<211> LENGTH: 21
<212> TYPE: DNA

```
<213> ORGANISM: Artificial Sequence
<220> FEATURE:
<223> OTHER INFORMATION: synthetic primer

<400> SEQUENCE: 19
agtccactga catgattgac a                                              21

<210> SEQ ID NO 20
<211> LENGTH: 21
<212> TYPE: DNA
<213> ORGANISM: Artificial Sequence
<220> FEATURE:
<223> OTHER INFORMATION: synthetic primer

<400> SEQUENCE: 20
gttttgacag aaacctttgc g                                              21

<210> SEQ ID NO 21
<211> LENGTH: 19
<212> TYPE: DNA
<213> ORGANISM: Artificial Sequence
<220> FEATURE:
<223> OTHER INFORMATION: synthetic primer

<400> SEQUENCE: 21
ttggtgcaca caggggttc                                                 19

<210> SEQ ID NO 22
<211> LENGTH: 21
<212> TYPE: DNA
<213> ORGANISM: Artificial Sequence
<220> FEATURE:
<223> OTHER INFORMATION: synthetic primer

<400> SEQUENCE: 22
actcgctaag tgttcgctac g                                              21

<210> SEQ ID NO 23
<211> LENGTH: 21
<212> TYPE: DNA
<213> ORGANISM: Artificial Sequence
<220> FEATURE:
<223> OTHER INFORMATION: synthetic primer

<400> SEQUENCE: 23
tgccatgtgc tagtccactg a                                              21
```

US 7,741,043 B2

CONTROL OF TGFβ SIGNALING BY KM23 SUPERFAMILY MEMBERS

CROSS REFERENCE TO RELATED APPLICATIONS

The present application is a divisional application of U.S. application Ser. No. 10/227,988, filed Aug. 26, 2002, now U.S. Pat. No. 7,229,758 which is a continuation-in-part of International Application No. PCT/US01/06176, filed Feb. 26, 2001, which claims the benefit of U.S. Provisional Application No. 60/184,843, filed Feb. 25, 2000, the contents all of which are incorporated herein by reference.

FIELD OF THE INVENTION

The present invention relates generally to isolated or recombinant polypeptides, or fragments thereof, which function in growth factor or cytokine signaling pathways. More specifically, the present invention relates to the specific family of polypeptides, or fragments thereof, termed km23 or mLC7, and its various forms, which interact with TGFβ receptors and/or are present in a signaling pathway for TGFβ superfamily members, or with subunits of the dynein motor complex. The km23 family members of the present invention are molecular targets against which therapeutics can be designed by molecular, immunological or pharmacological approaches, or for detection, diagnosing, or determining the prognosis of patients with abnormal growth control.

BACKGROUND OF THE INVENTION

The publications and other materials used herein to illuminate the background of the invention, and in particular to provide additional details relating to the invention, are referenced in the following text and are grouped in the appended list of references.

Transforming growth factor β's (TGFβ) are one of the few natural growth inhibitors which inhibit the growth of most epithelial cells. In contrast to other inhibitors, TGFβ is generally non cytotoxic, even at concentrations which are orders of magnitude above its effective concentration. TGFβ is the prototype for over 40 family members which share structural and functional similarities. The TGFβ superfamily plays an essential role in almost every aspect of cellular processes, including early embryonic development, cell growth, differentiation, cell motility, and apoptosis. See for example Yue and Mulder (2001); Sporn and Vilcek (2000); Massaque (1998); and Hartsough and Mulder (1997). The ability of TGFβ to potently inhibit the growth of many epithelial cells and solid tumors of epithelial origin, i.e. colon, breast, prostrate, lung, liver, ovarian, etc. is well established. However, many solid tumors develop resistance to the growth inhibitory effects of TGFβ. When cells become resistant to TGFβ, they no longer have the natural growth check provided by TGFβ and, as a result, may proliferate continually. Thus, TGFβ plays an important role in tumorigenesis and tumor aggressiveness. This resistance to TGFβ-mediated growth inhibition may occur at many levels. For example, the tumor cells may become unable to activate latent TGFβ (see for example, Wakefield et al. (1987); and Sporn et al., (1987), may display mutations in signaling receptors (Kim et al., 2000), or may develop defective TGFβ signaling pathways (Hartsough and Mulder, 1997).

TGFβ interacts with two major signaling receptors, designated RI and RII. The current working model for activation of the TGFβ receptors involves TGFβ binding by RII, which is constitutively phosphorylated. RII recruits RI into a complex (TβR complex) and phosphorylates RI in its GS domain. The complex then propagates the signal, presumably by interacting with and/or phosphorylating downstream cytoplasmic components (Wrana et al., 1994).

TGFβ RI and RII are mutated in human cancer cells (Massague, 1998). Mutations in TGFβ type II receptors are most common, particularly in human colon and gastric cancers; these are associated with microsatellite instability and a loss of TGFβ responsiveness (Markowitz et al., 1995). In addition, gross structural defects in the RII gene, as well as alterations in transcriptional repression of RII, contribute to a loss of TGFβ responsiveness (Kim et al., 2000). Although alterations in TGFβ RI receptors are less common, transcriptional repression of RI may be an alternative mechanism for subverting the growth inhibitory response to TGFβ. Other more subtle alterations in RI may also exist (Kim et al., 2000). However, if normal TGFβ receptors are expressed in cells with mutated receptors, TGFβ responsiveness does not always return. Thus, signal transduction pathways must also be altered.

Several types of signaling components have been described as participants in TGFβ signaling. These include protein kinase C (PKC), phospholipase C, protein phosphatase 1, Ras, several mitogen-activated protein kinases (Mapks), the Smads, and some of the Rho family members (Hartsough and Mulder, 1997; Mulder, 2000). Aside from the Ras/Mapk and Smad pathways, however, the generality and biological significance of the other components in the TGFβ pathway is unclear.

It has been demonstrated that TGFβ activates Ras within 3-6 min in untransformed epithelial cells that are TGFβ-sensitive, but not in cells that are TGFβ-resistant (Mulder and Morris, 1992). Several mitogen-activated protein kinases (Mapks) are also rapidly activated (within 5-30 min) after addition of TGFβ (Hartsough and Mulder, 1995; Frey and Mulder, 1997). The activation of some of the Mapks is sustained, indicative of nuclear translocation of the protein and subsequent regulation of transcription. The rapid kinetics for these effects indicate that they are direct, and not the consequence of the release of other growth factors that could subsequently regulate the Ras/Mapk pathways. It has also been shown that activation of Ras by TGFβ is required for the regulation of various cell cycle proteins in the nucleus (Yue et al., 1998). More recently, it has become clear that TGFβ activation of these pathways is required for transcriptional regulation of TGFβ itself, and the resulting autoproduction of TGFβ (Yue and Mulder, 2000).

The Smad superfamily are highly conserved proteins which include the *Drosophila* MAD and DAD proteins, three *C. elegans* proteins, a few *xenopus* proteins, and nine mammalian Smad isoforms (reviewed in Wrana and Attisano, 2000; Miyazono, 2000). Based upon accumulating evidence pertaining to the Smads, a general model for Smad function has been proposed. The so-called "receptor activated" RSmads (i.e., Smads 1-3 and 5) are phosphorylated after receptor activation and form a complex with the Smad 4 type components (common-partner Smad or co-Smad). Smad 4/dpc4 itself is not phosphorylated, but its heterocomplex formation with the other Smads is thought to mediate translocation of Smads to the nucleus and transcriptional activation.

Over the past years, progress has been made in identifying signal transduction components activated by TGFβ superfamily members. However, even though various signaling proteins have been analyzed, the cytoplasmic pathways regulated by TGFβ are still very poorly understood. It should be noted that discovery of TGFβ signaling components which are essential for mediating the biological responses of TGFβ has been difficult. For example, Smads were identified based upon homology screens using the *Drosophila* or *C. elegans* cDNAs. It is further noted that both the Smad and the Ras/Mapk pathways regulate transcriptional events. Clearly, TGFβ has functions in addition to transcriptional regulation. Thus, there is a need for identifying components which play a role in TGFβ signaling and/or regulate cellular events in addition to transcription.

Several potential TGFβ signaling components have been identified based upon their interaction with TGFβ receptors. Initial studies led to the identification of FKBP12 and the alpha subunit of farnesyl transferase as TGFβ RI interactors, TRIP-1 as an RII-interacting protein, and clusterin (also called apolipoprotein J) as a component that interacts with both TGFβ receptors. (See for example, Kawabata et al., 1995; Ventura et al., 1996; Reddy et al., 1996). Additional studies led to the discovery of TRAP-1 as an interactor of the constitutively active triple RI mutant (L193A, P194A, T204D) and STRAP (a WD-domain protein) as a component that associates with both RI and RII (See for example, Charng et al., 1998; Datta et al., 1998). Another WD domain protein that interacts with TGFβ RI was identified as the $β_α$ subunit of protein phosphatase 2A (See for example, Griswold-Prenner et al., 1998). However, the functional significance of these factors is, at present, unclear.

Various Smad-interacting proteins have also been identified, including SARA, which interacts with both Smads and TGFβ receptors (See for example, Tsukazaki et al., 1998). Several of the Smad-interacting factors have been shown to function as transcriptional repressors or co-activators (See for example, Massague and Chen, 2000; Hata et al., 2000). These factors address the transcriptional functions of TGFβ. However, they do not explain or provide insight into how TGFβ accomplishes the diverse activities which make it a multifunctional polypeptide. In addition, the alterations found thus far in these signaling components do not explain the diverse types of cancers that arise from a loss of growth control related to TGFβ or its signaling pathways. Thus, it is clear that there are additional TGFβ signaling components and pathways which are important to the complete understanding of how TGFβ asserts its growth suppressive and other functions inside cells and how these pathways are subverted to result in epithelial cancers.

Since TGFβ plays a critical role in such a vast array of human pathologies, any factor in one of TGFβ's signaling pathways is sure to have therapeutic potential for one or more of these diseases. These human pathologies include cancer, atherosclerosis, restenosis, arteriosclerosis, diabetic kidney disease, glomerulosclerosis, most progressive renal disorders, other sclerotic diseases, stroke, chronic inflammation, arthritis, hyperreactivity of the lymphoid system, asthma, periodontal disease, glaucoma, pulmonary fibrosis, other fibrotic diseases, scarring during wound healing, osteoporosis, neurodegenerative diseases, ischemic injury, encephalomyelitis, autoimmunity, immunodeficiencies, and other immune mediated-pathologies (See Sporn and Vilcek, 2000).

Of particular interest, TGFβ has been shown to be a tumor suppressor displaying true haploid insufficiency in its ability to protect against tumorigenesis (Tang et al. 1998). Many of the signaling components identified in the TGFβ signaling pathway have also been shown to function as tumor suppressors. Notwithstanding new technologies, aggressive surgery, and modern chemotherapy, there has been little change in the survival of cancer patients having specific types of cancers over the past several years. The genetics of cancer is complicated, involving multiple dominant, positive regulators of the transformed state (oncogenes) as well as multiple recessive, negative regulators (tumor suppressor genes). Over 100 oncogenes have been characterize thus far. However, fewer than a dozen tumor suppressor genes have been identified, although the number is expected to increase significantly (Knudson, 1993).

The involvement of so many genes underscores the complexity of the growth control mechanisms that operate in cells to maintain the integrity of normal tissue. So far, no single gene has been shown to participate in the development of all, or even the majority, of human cancers. The most frequently mutated tumor suppressor gene is the p53 gene, mutated in roughly 50% of all tumors. The hope for a new generation of specifically targeted anti-tumor therapeutics may rest upon the ability to identify tumor suppressor genes that play important roles in the control of cell division. TGFβ receptor-interacting proteins or components of TGFβ superfamily member signaling pathways are likely to represent potential tumor suppressor genes.

Dynein is a molecular motor protein which mediates intracellular transport; it conveys its cargo along polarized microtubules (MTs) toward the minus ends. It is a massive multi-subunit complex composed of heavy chains (HC's), intermediate chains (IC's), light intermediate chains (LIC's), light chains (LC's), and IC/LC-associated proteins (Hirokawa, 1998). The MT-binding domain is located within the HC's that form the globular heads and stems of the complex, whereas cargo-binding activity involves the IC's and several classes of LC's that associate at the base of the soluble dynein particle. Evidence also exists to suggest that the IC/LC complexes have a distinct and stable structure (King, 2000).

Dynein superfamily members appear to control various cell functions which include axonal transport, flagellar motility, organization of the mitotic spindle, distribution of late endosomes and lysosomes, the centrosomal localization of the Golgi complex, vesicular transport from early to late endosomes, the apical transport of Golgi-derived membranes in epithelial cells, the movement of phagosomes, and others (see for example, in Hirokawa, 1998). However, little is known about the regulation of the movement that the dynein motors drive. A large number of cytoplasmic dynein-associated proteins with diverse structural and functional roles have been identified (Milisav, 1998). However, it remains obscure as to the requirement by dynein of so many associated LC's, and LC/IC-associated proteins.

A new family of dynein-associated proteins which are both *Drosophila* roadblock (robl)-like, *Chlamydomonas* dynein light chain 7 (LC7)-like, and *Drosophila* bithoraxoid (bxd)-like have been described (Bowman et al., 1999). The original *Drosophila* bithoraxoid (bxd) gene of this family has been described in detail, but the transcripts are not encoded into protein (Lipshitz et al., 1987). Bxd is actually part of a huge bithorax gene complex (BX-C) which plays a role in segment development in *Drosophila* (Morata and Kerridge 1981; Smolik-Utlaut 1990; Stern, 1998). However, no functional studies have been reported with regard to bxd-like encoded proteins. km23 has 67% homology with robl and is identical to the class 1 mammalian robl-like proteins thought to play a role in cytoplasmic dynein functions. Accordingly, these results suggest that km23 is a dynein LC of the LC7 family that plays an important role in MT dynamics. Our data indicate that this is, indeed, the case. However, more importantly, our discovery of km23 as a TGFβ-receptor interactor and a dynein-interactor establishes the first connection between TGFβ-receptors and minus end MT dynamics, and indicates that such receptors can regulate dynein-mediated MT functions.

Although a recent report has described MTs as a cytoplasmic sequestering network for the Smads (Dong et al., 2000), these results again focus on the transcriptional functions of TGFβ. In this context, MTs appear to function by negatively regulating Smad transcriptional responses. However, no direct studies have been performed to determine how TGFβ may regulate MTs to induce the intracellular transport of specific proteins, and/or to mediate the diverse functions of TGFβ.

MTs are 25-nm tubule-like structures composed of alpha- and beta-tubulin heterodimers (reviewed in Hirokawa, 1998). Several parallel protofilaments composed of linearly arranged heterodimers form the MT wall, to which MT-associated proteins and motor proteins bind. MTs are polar structures with a fast-growing plus end and a minus end. They function as "rails" for the transport of organelles via MT-associated motor proteins such as dynein. MTs are important for many cellular processes, and play an important role in the generation and maintenance of epithelial cell polarity (Hofer et al., 1998). Outer arm dynein-associated proteins interact with dynein at the base of the dynein particle, as well as possibly with other proteins present in the cytoplasmic dynein complex (Bowman et al., 1999). However, it is unclear whether growth factors such as TGFβ can regulate dynein MT transport.

The sum total of distinct, yet interacting, signaling pathways that are activated simultaneously after TGFβ receptor activation, will play a significant role in both the normal growth of cells and in a variety of critical pathological conditions. Accordingly, identification of additional TGFβ signaling components and pathways will greatly advance our overall understanding of intracellular targets that dictate the fate of the organism. Thus, a need in the art exists for the discovery of TGFβ receptor-interacting proteins or TGFβ signaling components, and the polynucleotides encoding them, in order to provide new compositions which are useful in the diagnosis, prevention, and treatment of disorders associated with cancer and other diseases the development and progression in which TGFβ has been implicated.

SUMMARY OF THE INVENTION

The present invention relates to the family of polypeptides known as km23 or mLC7, and its various forms, which interact with TGFβ receptors and/or are present in signaling pathways for TGFβ superfamily members. The members also interact with the dynein motor complex. The km23/mLC7 family members of the present invention are useful for detecting, diagnosing, or determining the prognosis of patients with abnormal growth control, and are molecular targets against which therapeutics can be designed by molecular, immunological or pharmacological approaches. For the purposes of this invention, km23 shall refer to all mammalian homologues of the LC7 family of dynein light chains (mLC7's).

The invention provides for isolated or recombinant km23 polypeptides, including protein fragments, and mutant km23 polypeptides. The present invention is based, in part, on the ability of km23 protein generally represented by the formula SEQ ID NO:1 or SEQ ID NO:2 to mediate the signal transduction activity of the TGFβ superfamily of growth factors.

The invention particularly relates to alterations in the km23 genes that result in the production of mutant km23 polypeptides, truncated km23 polypeptides and elongated km23 protein forms, and their use in the diagnosis or predisposition to several cancers, including, but not limited to, ovarian cancer, breast cancer, and colon cancer.

The present inventor has developed various methods of determining the presence or absence of a lesion in a patient sample which is characterized by an alteration in the sequence of a km23 nucleic acid or polypeptide form. One such method according to the present invention includes: (a) providing a km23 RNA form from a patient specimen; (b) providing a first pair of PCR primers which span the entire open reading frame of km23; (c) performing a first round of nested RT-PCR using (i) the km23 RNA form as the reaction template and (ii) the first primer pair under suitable conditions to obtain a first PCR product; (d) providing a second pair of PCR primers capable of binding within the first PCR product; (e) performing a second round of nested RT-PCR using the first PCR product as the reaction template under suitable conditions to obtain a second PCR product; and (f) sequencing and aligning the second PCR product with a wild-type km23 nucleic acid form to determine a specific alteration in sequence. This method is useful for detecting the types of alterations in a patient and their frequency in a given patient population.

The invention further provides a method of determining the presence or absence of a lesion in a patient specimen which is characterized by a specific alteration in sequence of a km23 nucleic acid or polypeptide form, the method including: (a) providing a km23 genomic nucleic acid form from a patient specimen; (b) providing a first pair of PCR primers which span exon 3 of said km 23 genomic nucleic acid form; and (c) performing a first round of nested PCR amplification of a region of the km23 genomic nucleic acid form that includes exon 3 using the first pair of primers under suitable conditions to obtain a first PCR product; (d) providing a second pair of PCR primers capable of binding within the first PCR product; (e) performing a second round of nested PCR amplification using the first PCR product as the reaction template under suitable conditions to obtain a second PCR product; and (f) sequencing and aligning the second PCR product with a wild-type km23 nucleic acid form to determine a specific alteration in sequence.

Also provided is a method of determining the presence or absence of a lesion in a patient specimen which is characterized by a specific alteration in sequence of a km23 nucleic acid or polypeptide form, the method including: (a) providing a km23 genomic nucleic acid form from a patient specimen; (b) providing a first pair of PCR primers which span exon 2 of the km23 genomic nucleic acid form; and (c) performing a first round of nested PCR amplification of a region of the km23 genomic nucleic acid form that includes exon 2 using the first pair of primers under suitable conditions to obtain a first PCR product; (d) providing a second pair of PCR primers capable of binding within the first PCR product; (e) performing a second round of nested PCR amplification using the first PCR product as the reaction template under suitable conditions to obtain a second PCR product; and (f) sequencing and aligning the second PCR product with a wild-type km23 nucleic acid form to determine a specific alteration in sequence.

Moreover, the invention provides a method of determining the presence or absence of a lesion in a patient specimen characterized by a specific alteration in sequence of a km23 nucleic acid or polypeptide form, the method including: (a) providing a km23 genomic nucleic acid form from a patient specimen; (b) providing a first pair of PCR primers which span exon 4 of the km23 genomic nucleic acid form; and (c) performing a first round of nested PCR amplification of a region of the km23 genomic nucleic acid form that includes exon 4 using the first pair of primers under suitable conditions to obtain a first PCR product; (d) providing a second pair of PCR primers capable of binding within the first PCR product; (e) performing a second round of nested PCR amplification using the first PCR product as the reaction template under suitable conditions to obtain a second PCR product; and (f) sequencing and aligning the second PCR product with a wild-type km23 nucleic acid form to determine a specific alteration in sequence.

The invention further relates to methods for screening for specific alterations in a km23 nucleic acid form relative to the wild-type km23 nucleic acid form. In particular, the invention provides a method for screening for the presence or absence of a lesion in a patient specimen which is characterized by an alteration in a km23 nucleic acid or polypeptide form, the method including: (i) providing a km23 nucleic acid form from a patient specimen; and (ii) detecting the presence of an alteration in a km23 nucleic acid form relative to the wild-type km23 nucleic acid form, which alteration results in one of the following: (a) a mutant km23 polypeptide having a Gly at the amino acid corresponding to amino acid number 55 of SEQ ID NO: 1 or SEQ ID NO: 2; (b) a mutant km23 polypeptide having a Val at the amino acid corresponding to amino acid number 89 of SEQ ID NO: 1 or SEQ ID NO: 2; (c) a mutant km23 polypeptide having a Ile at the amino acid corresponding to amino acid number 46 of SEQ ID NO: 1 or SEQ ID NO: 2; and (d) a mutant km23 polypeptide having a Ser at the amino acid corresponding to amino acid number 56 of SEQ ID NO: 1 or SEQ ID NO: 2; (e) a mutant km23 polypeptide having an Ala at the amino acid corresponding to amino acid number 4 of SEQ ID NO:1 or SEQ ID NO:2; (f) a mutant km23 polypeptide having an Ala, Asp, or Glu at the amino acid corresponding to amino acid number 32 of SEQ ID NO: 1 or SEQ ID NO: 2; (g) a mutant km23 polypeptide having a Glu or Asp at the amino acid corresponding to amino acid number 55 of SEQ ID NO: 1 or SEQ ID NO: 2; (h) a mutant km23 polypeptide having a Ala, Glu, or Asp at the amino acid corresponding to amino acid number 73 of SEQ ID NO: 1 or SEQ ID NO: 2; (i) a mutant km23 polypeptide having a Ala, Asp, or Glu at the amino acid corresponding to amino acid number 7 of SEQ ID NO: 1 or SEQ ID NO: 2; (j) a mutant km23 polypeptide having a Ala, Asp, or Glu at the amino acid corresponding to amino acid number 33 of SEQ ID NO: 1 or SEQ ID NO: 2; and (k) a mutant km23 polypeptide having a Ala, Asp, or Glu at the amino acid corresponding to amino acid number 56 of SEQ ID NO: 1 or SEQ ID NO: 2; (l) a mutant km23 polypeptide having an Ala or Glu at the amino acid corresponding to amino acid number 13 of SEQ ID NO:1 or SEQ ID NO:2; (m) a km23 polypeptide having SEQ ID NO:1 or SEQ ID NO:2, except that the polypeptide lacks amino acids corresponding to amino acids 27-82 in SEQ ID NO:1 or SEQ ID NO:2; and (n) a km23 polypeptide having the amino acid sequence corresponding to SEQ ID NO:6.

Another aspect of the invention relates to a method of determining if a patient is at risk for a disorder or has a disorder by detecting, in a patient specimen, the presence or absence of a lesion in a patient specimen characterized by an alteration in post-translational modification of a km23 nucleic acid or polypeptide form.

Each of the above-described methods is useful for both diagnostic, as well as prognostic screening.

As described above, the present inventor has discovered that km23 is a TGFβ signaling intermediate. As such, the present invention provides a method of mediating or modulating the signal transduction activity of at least one TGFβ superfamily member, the method including introducing into the cell a km23 polypeptide, fragment thereof or mutant form of either.

Another aspect of the invention relates to a method of modulating the signal transduction activity of at least one TGFβ superfamily member, the method including introducing into the cell an antagonist of a km23 nucleic acid form, or an antagonist of amino acids encoded by the nucleic acid form.

The invention also relates to a method of modulating at least one of the following: regulation of gene expression, cell growth, cell differentiation, cell survival, apoptosis, senescence, cell migration, angiogenesis, fibrosis, wound healing, extracellular matrix induction, adhesion, autoproduction, embryogenesis and combinations thereof, the method including introducing into the cell an antagonist of a km23 nucleic acid form or an antagonist of amino acids encoded by the nucleic acid form.

Furthermore, the invention provides a method of modulating at least one of the following: actin cytoskeleton dynamics, microtubule dynamics, intracellular transport, cell polarity, dynein-mediated microtubule transport and combinations thereof, the method including introducing into the cell an antagonist of a km23 nucleic acid form or an antagonist of amino acids encoded by the nucleic acid form.

The invention further provides various methods for identifying therapeutic agents. For example, the invention provides a method for identifying therapeutic agents that inhibit, potentiate, or mimic the ability of a km23 polypeptide, mutant form thereof, or a nucleic acid encoding the polypeptide or mutant form thereof, to modulate the signal transduction activity of a growth factor or cytokine, the method including: (a) treating a cell with an effective amount of at least one candidate so as to alter at least one of the following: regulation of gene expression, cell growth, cell differentiation, cell survival, apoptosis, senescence, cell migration, angiogenesis, fibrosis, wound healing, extracellular matrix induction, adhesion, autoproduction, embryogenesis and combinations thereof; and (b) measuring the effect of the candidate on the cell.

The invention further provides a method for identifying therapeutic agents that inhibit, potentiate, or mimic the ability of a km23 polypeptide, mutant form thereof, or a nucleic acid encoding the polypeptide, or mutant form thereof, to modulate the signal transduction activity of a growth factor or cytokine, the method including: (a) treating a cell with an effective amount of at least one candidate so as to alter at least one of the following: actin cytoskeleton dynamics, microtubule dynamics, intracellular transport, cell polarity, dynein-mediated microtubule transport and combinations thereof; and (b) measuring the effect of the candidate on the cell.

Also provided is a method of screening for a therapeutic agent that inhibits or stimulates the interaction of a km23 polypeptide form with a specific binding protein (e.g. a receptor or the dynein intermediate chain), the method including: (a) providing drug-inducible km23 expressing cells, wherein the expressed km23 is a wild-type form or an altered form thereof; (b) treating the cells of (a) with an effective amount of a therapeutic candidate so as to alter the growth inhibitory effect of km23; and (c) measuring the effect of the candidate on the cells with a cell growth assay.

In addition, the invention provides a method of screening for a therapeutic agent that modulates the interaction of a km23 polypeptide form with the dynein intermediate chain, the method including: (a) providing a fusion protein comprising a dynein intermediate chain polypeptide form labeled with a first fluorophore; (b) providing a fusion protein comprising a km23 polypeptide form labeled with a second fluorophore; (c) incubating components (a) and (b) in the presence and absence of an effective amount of a therapeutic candidate under suitable conditions to allow protein interaction between components (a) and (b); and (d) detecting the effect of the candidate on the interaction by comparing the fluorescence spectra for each of the fluorescently labeled polypeptides in the presence and absence of the candidate.

Another aspect of the invention relates to a method of restoring the growth inhibitory activity of at least one TGFβ superfamily member, the method including introducing into the cell an antagonist of a mutant km23 polypeptide form.

The invention further relates to a method of regulating TGFβ production, the method including introducing into the cell a mimetic or an antagonist of a mutant km23 polypeptide form.

The invention also provides new compositions which are useful in the diagnosis, prevention, and treatment of disorders associated with cancer and other diseases, the development and progression in which TGFβ has been implicated.

For example, the invention provides an isolated or recombinant km23 polypeptide, fragment, or mutant form thereof, wherein the fragment mediates or modulates the intracellular signal transduction activity of at least one TGFβ superfamily member.

The invention also provides a km23 polypeptide fragment selected from the following: (a) a fragment including the amino acid sequence corresponding to amino acids 1-26 in SEQ ID No:1 or SEQ ID: NO:2; (b) a fragment including the amino acid sequence corresponding to amino acids 2-26 in SEQ ID No:1 or SEQ ID: NO:2; (c) a fragment including the amino acid sequence corresponding to amino acids 27-82 in SEQ ID No:1 or SEQ ID: NO:2; (d) a fragment comprising the amino acid sequence corresponding to amino acids 83-96 in SEQ ID No:1 or SEQ ID: NO:2; (e) a fragment of claim 1 including the amino acid sequence corresponding to amino acids 2-82 in SEQ ID No:1 or SEQ ID: NO:2; (f) a fragment including the amino acid sequence corresponding to amino acids 27-96 in SEQ ID No:1 or SEQ ID: NO:2; and (g) a fragment including a combination of (a) the amino acid sequence corresponding to amino acids 1-26 in SEQ ID NO:1 or SEQ ID NO:2; and (b) the amino acid sequence corresponding to amino acids 83-96 in SEQ ID NO:1 or SEQ ID NO:2.

Further provided is an isolated or recombinant km23 polypeptide comprising SEQ ID NO:1 or SEQ ID NO:2, except that the polypeptide lacks amino acids corresponding to amino acids 27-82 in SEQ ID NO:1 or SEQ ID NO:2.

The invention also provides an isolated or recombinant km23 polypeptide comprising the amino acid sequence corresponding to SEQ ID NO:6.

Further provided is a mutant km23 polypeptide or a fragment thereof which mediates or modulates the intracellular signal transduction activity of at least one TGFβ superfamily member. In particular, the invention provides a mutant km23 polypeptide selected from the following: (a) a mutant km23 polypeptide having a Gly at the amino acid corresponding to amino acid number 55 of SEQ ID NO: 1 or SEQ ID NO: 2; (b) a mutant km23 polypeptide having a Val at the amino acid corresponding to amino acid number 89 of SEQ ID NO: 1 or SEQ ID NO: 2; (c) a mutant km23 polypeptide having a Ile at the amino acid corresponding to amino acid number 46 of SEQ ID NO: 1 or SEQ ID NO: 2; and (d) a mutant km23 polypeptide having a Ser at the amino acid corresponding to amino acid number 56 of SEQ ID NO: 1 or SEQ ID NO: 2; and (e) a mutant km23 polypeptide having an Ala at the amino acid corresponding to amino acid number 4 of SEQ ID NO:1 or SEQ ID NO:2.

Furthermore, the invention provides a mutant km23 polypeptide selected from the following: (a) a mutant km23 polypeptide having an Ala, Asp, or Glu at the amino acid corresponding to amino acid number 32 of SEQ ID NO: 1 or SEQ ID NO: 2; (b) a mutant km23 polypeptide having a Glu or Asp at the amino acid corresponding to amino acid number 55 of SEQ ID NO: 1 or SEQ ID NO: 2; (c) a mutant km23 polypeptide having a Ala, Glu, or Asp at the amino acid corresponding to amino acid number 73 of SEQ ID NO: 1 or SEQ ID NO: 2; (d) a mutant km23 polypeptide having a Ala, Asp, or Glu at the amino acid corresponding to amino acid number 7 of SEQ ID NO: 1 or SEQ ID NO: 2; (e) a mutant km23 polypeptide having a Ala, Asp, or Glu at the amino acid corresponding to amino acid number 33 of SEQ ID NO: 1 or SEQ ID NO: 2; (f) a mutant km23 polypeptide having a Ala, Asp, or Glu at the amino acid corresponding to amino acid number 56 of SEQ ID NO: 1 or SEQ ID NO: 2; and (g) a mutant km23 polypeptide having an Ala or Glu at the amino acid corresponding to amino acid number 13 of SEQ ID NO: 1 or SEQ ID NO: 2.

The invention also provides a cloned mutant km23 nucleic acid form, wherein the mutant form mediates or modulates the intracellular signal transduction activity of at least one TGFβ superfamily member. Cloned mutant km23 nucleic acid forms are characterized by mutation of at least one nucleotide base relative to a wild-type km23 nucleic acid form. The invention provides cloned mutant km23 nucleic acid forms in which the mutation results in a mutant km23 polypeptide selected from those specific mutant km23 polypeptides described above.

The invention further encompasses cloned km23 nucleic acid forms including a nucleotide sequence encoding the specific km23 polypeptide fragments described above.

Moreover, the invention provides a cloned km23 nucleic acid form, which includes a nucleotide sequence encoding a km23 polypeptide having SEQ ID NO: 1 or SEQ ID NO: 2, except that the polypeptide lacks amino acids corresponding to amino acids 27-82 in SEQ ID NO: 1 or SEQ ID NO: 2.

In addition, the invention provides a cloned km23 nucleic acid form, which includes a nucleotide sequence encoding a km23 polypeptide corresponding to SEQ ID NO: 6.

Another aspect of the invention relates to vectors capable of expressing in a host cell the specific mutant km23 polypeptides described above. Also encompassed by the invention are expression vectors capable of expressing in a host cell a km23 polypeptide having SEQ ID NO: 1 or SEQ ID NO: 2, except that the polypeptide lacks amino acids corresponding to amino acids 27-82 in SEQ ID NO: 1 or SEQ ID NO: 2. Furthermore, the invention provides an expression vector capable of expressing in a host cell a km23 polypeptide corresponding to SEQ ID NO: 6.

The invention also relates to a substantially pure oligonucleotide or primer, the oligonucleotide or primer including a region of nucleotide sequence capable of hybridizing under stringent conditions to at least about 12 consecutive nucleotides of sense or antisense sequence of a cloned mutant km23 nucleic acid form provided by this invention, and the use of such oligonucleotides or primers in the diagnosis and prognosis of hyper-proliferative disorders and in gene therapy.

The invention also provides kits for diagnostic or prognostic screening of a km23 nucleic acid sample. In one embodiment, the kit includes: (a) a first pair of PCR primers having SEQ ID NO: 20 and SEQ ID NO: 21; (b) a second pair of PCR primers having SEQ ID NO: 22 and SEQ ID NO: 23; (c) a negative control comprising a wild-type km23 cDNA; and (d) a positive control comprising a km23 mutant cDNA.

The invention also relates to a monoclonal antibody that binds specifically to an antigenic determinant in a mutant km23 polypeptide form provided by this invention.

BRIEF DESCRIPTION OF THE DRAWINGS

FIG. 1(A and B). Alignment of human (h) and rat (r) km23 cDNA's, including the 5' and 3' regions. The coding region from 1 to 96 is shown in FIGS. 1A and 1B with consensus phosphorylation sites for protein kinase C (PKC) and casein kinase II (CKII) designated by brackets above each potential site. Exon positions are further shown in FIGS. 1A and 1B.

DETAILED DESCRIPTION OF THE INVENTION

Figure 2A:
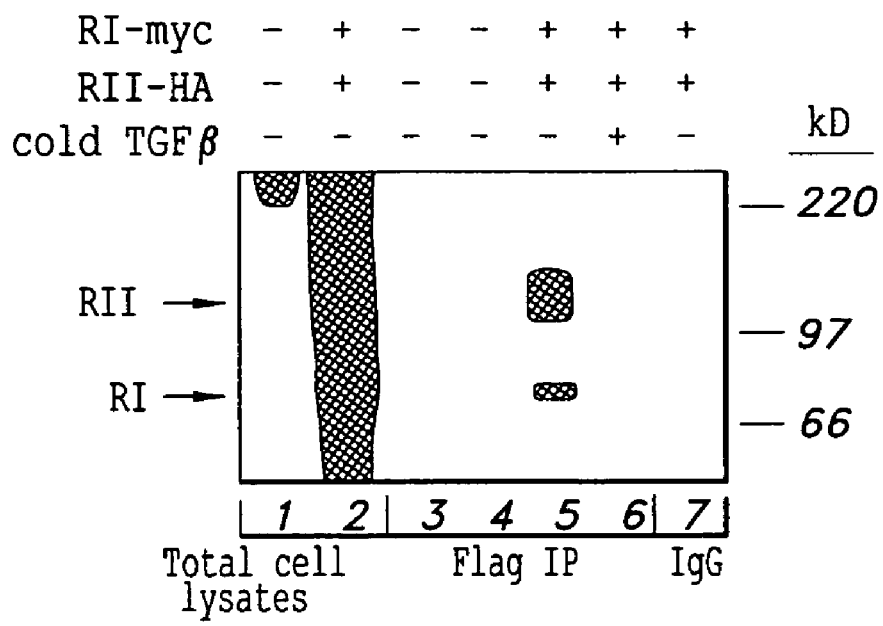
FIG. 2. RI and RII TGFβ receptors are present in km23 immunocomplexes. A: $^{125}$I-TGFβ affinity labeling of 293T cells transiently transfected with km23-flag, RI-myc, and RII-HA. After the 4 h $^{125}$I-TGFβ labeling period (4° C.), the cross-linking agent disuccinimidylsuberate (DSS) was added for an additional 15 min. Total cell lysates (lanes 1-2), or lysates immunoprecipitated (IP'd) with an anti-flag M2 antibody (Ab) (lanes 3-6) or with IgG (lane 7, control) were visualized by SDS-PAGE. B: Flag immunoblot of cell lysates as in A confirms km23 expression in the relevant lanes (2, 4-6). C: Myc immunoblot of cell lysates demonstrating expression of RI-myc in the relevant lanes (2, 5-6). D: RII immunoblot of cell lysates demonstrating expression of RII-HA in the relevant lanes (2, 5-6).

The present invention is based, at least in part, on the discovery of the inventor that a protein termed km23 associates with a transforming growth factor β (TGFβ) receptor. The discovery of km23 as both a TGFβ-receptor interactor and a dynein-interactor establishes the first connection between TGFβ and minus end MT dynamics, and indicates that TGFβ receptors can regulate dynein-mediated MT functions.

The km23 polypeptides, fragments thereof, mutants thereof, and the nucleic acid forms encoding them which are provided by the present invention satisfy a need in the art by providing new compositions which are useful in the diagnosis, prevention and treatment of disorders associated with a lesion of a km23 nucleic acid or polypeptide form. The lesion may be characterized by a specific alteration in sequence, a post-translational modification or some combination thereof of a km23 nucleic acid or peptide form which may result in altered expression or activity of the km23 protein. Any means of altering expression or activity of TGFβ signal transducers or modulators, inclusive of km23, via molecular and immunological approaches, as well as by using pharmacological agonists or antagonists, will have important consequences for the treatment of cancer and many other human diseases for which TGFβ superfamily members regulate the relevant cellular processes involved.

It is noted that unless indicted otherwise, km23 forms include km23 polypeptides, fragments thereof, or mutants thereof, as well as polypeptides, fragments, or mutants which are of the same superfamily as the km23/mLC7 protein. The term "km23 form" also includes all relevant nucleotide sequences encoding these polypeptides. Moreover, in the methods of this invention, useful km23 mutants include, but are not limited to, those described herein.

The present inventor has used a modification of a cloning of receptors targets (CORT) protocol to identify a protein which interacts with the TGFβ receptor. The original protocol required significant modifications for the application to the identification of TGFβ receptor signaling mediators. Briefly, the phosphorylated, activated intracellular domains of the TGFβ receptor complex were used as a probe, under highly specific conditions, to screen an expression library that was prepared by the inventor from a highly TGFβ responsive intestinal, epithelial cell line from rat. This cell line was developed in the inventor's laboratory. Several positive clones were obtained, one of which was termed km23. The nucleic acid sequence obtained from the km23 rat clone is represented by the formula in SEQ ID NO: 4. The cDNA represented in SEQ ID NO: 4, was found to encode the amino acid sequence represented in SEQ ID NO: 2. A full-length clone was further obtained from a human placental expression library, the sequence for which is represented by the formula in SEQ ID NO: 3. The full-length cDNA from human was found to encode the amino acid sequence represented by SEQ ID NO: 1.

Referring now to FIG. 1, which shows the alignment of the human and rat km23 cDNA, including the 5' and 3' regions, the coding region of the human cDNA is shown as extending from amino acids 1-96 and is shown as having consensus phosphorylation sites for protein kinase C (PKC) and casein kinase II (CKII) as designated by brackets above each potential site. In addition, there are several transcriptional regulatory elements in both the 5' and 3' regions, such as, but not limited to, AP-1, SBE, Sp1, and TCE. Positions of exons are also shown. The rat and human sequences are 96% identical and 98% similar based on their cDNA sequences.

Based upon homology to sequences in the database, km23 was determined to be part of a new family of dynein-associated proteins which are both *Drosophila* roadblock-like, (robl), *Chlamydomonas* dynein light chain 7 (LC7)-like, and *Drosophila* bithoraxoid (bxd)-like (Bowman et al., 1999). Based on a review of the Bowman report, as well as further examination of sequences in available databases, it was determined that km23 (also known as mLC7-1, Tang et al. Molec. Biol. of the Cell, In Press, 2002) is identical to the class 1 mammalian robl-like proteins thought to play a role in cytoplasmic dynein functions. However, no association was ever previously made between the class 1 mammalian robl-like proteins and TGFβ superfamily signaling.

The results detailed in the examples shown below demonstrate that km23, in addition to being a member of the dynein-associated proteins, is a TGFβ signaling intermediate. The results detailed in the example section demonstrate that the km23 protein interacts with the TGFβ receptors, is phosphorylated by them, and synergizes with TGFβ to stimulate transcriptional activation of a cAMP-responsive element (CRE) reporter. The inventor's results further demonstrate that km23 (which is also a dynein light chain mCL7-1) does, in fact, bind to the dynein motor protein complex through the dynein intermediate chain (DIC), and that TGFB receptor activation is linked to the recruitment of km23 to the DIC. The inventor's finding that TGFβ can regulate a member, namely km23, of the dynein-associated proteins, and thereby control dynein motoring along microtubules towards the minus ends, indicates a novel function for TGFβ in microtubule dynamics.

Figure 4:
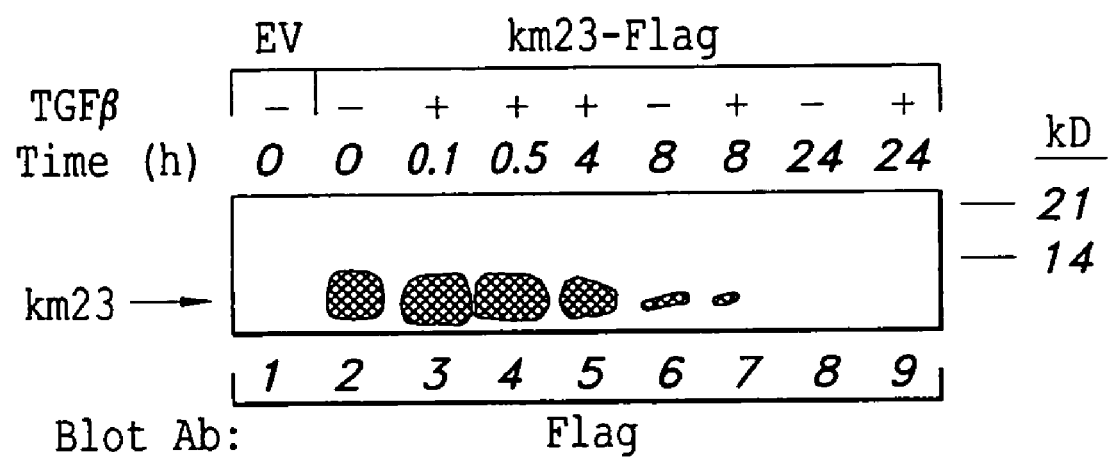
FIG. 4. Kinetics for TGFβ Induction of km23 Expression in MDCK cells. MDCK cells were transiently transfected with km23-flag. 36 h after transfection, cells were treated with TGFβ for various time points and then lysed. Total cell lysates were subjected to Western Blot analysis with an anti-flag Ab.

A clear role for km23 as a signaling intermediate in the TGFβ signal transduction pathway was established by the following specific findings of the inventor: (1) both the RI and RII TGFβ receptors are present in km23 immuno complexes (FIG. 2); (2) km23 is phosphorylated by the RI/RII TGFβ receptor complex (FIG. 3); (3) TGFβ is capable of inducing the expression of km23 proteins in MDCK cells, a canine kidney cell type (FIG. 4); (4) expression of km23 can induce JNK activity and c-Jun phosphorylation (TGFβ signaling events) in the absence of TGFβ (Tang et al., 2002), indicating that km23 may include as one of its functions the production of TGFβ; (5) km23 can synergize with the TGFβ receptor complex and with TGFβ to stimulate CRE luciferase reporter activity, indicating km23 may include as one of its functions the production of TGFβ$_2$ or TGFβ$_3$ (FIG. 5); (6) km23 interacts with Smad 2, which is an important signaling component of TGFβ signaling pathways (FIG. 7); and (7) expression of km23 inhibits cell growth of Mv1Lucells (FIG. 16) and of MDCK cells.

The present inventor has identified novel km23 alterations in ovarian cancer patient tissues. Patient samples were microdissected using LCM, analyzed by nested RT-PCR, and sequenced to detect the precise alterations using the diagnostic/prognostic methods of this invention. The identified km23 alterations were characterized by a mutation of at least one nucleotide base relative to a wild-type km23 nucleic acid form, the mutation resulting in the following mutant km23 polypeptides: (a) a mutant km23 polypeptide having a Gly at the amino acid corresponding to amino acid number 55 of SEQ ID NO: 1 or SEQ ID NO: 2; (b) a mutant km23 polypeptide having a Val at the amino acid corresponding to amino acid number 89 of SEQ ID NO: 1 or SEQ ID NO: 2; (c) a mutant km23 polypeptide having a Ile at the amino acid corresponding to amino acid number 46 of SEQ ID NO: 1 or SEQ ID NO: 2; (d) a mutant km23 polypeptide having a Ser at the amino acid corresponding to amino acid number 56 of SEQ ID NO: 1 or SEQ ID NO: 2; and (e) a mutant km23 polypeptide having an Ala at the amino acid corresponding to amino acid 4 of SEQ ID NO: 1 or SEQ ID NO: 2.

Figure 8:
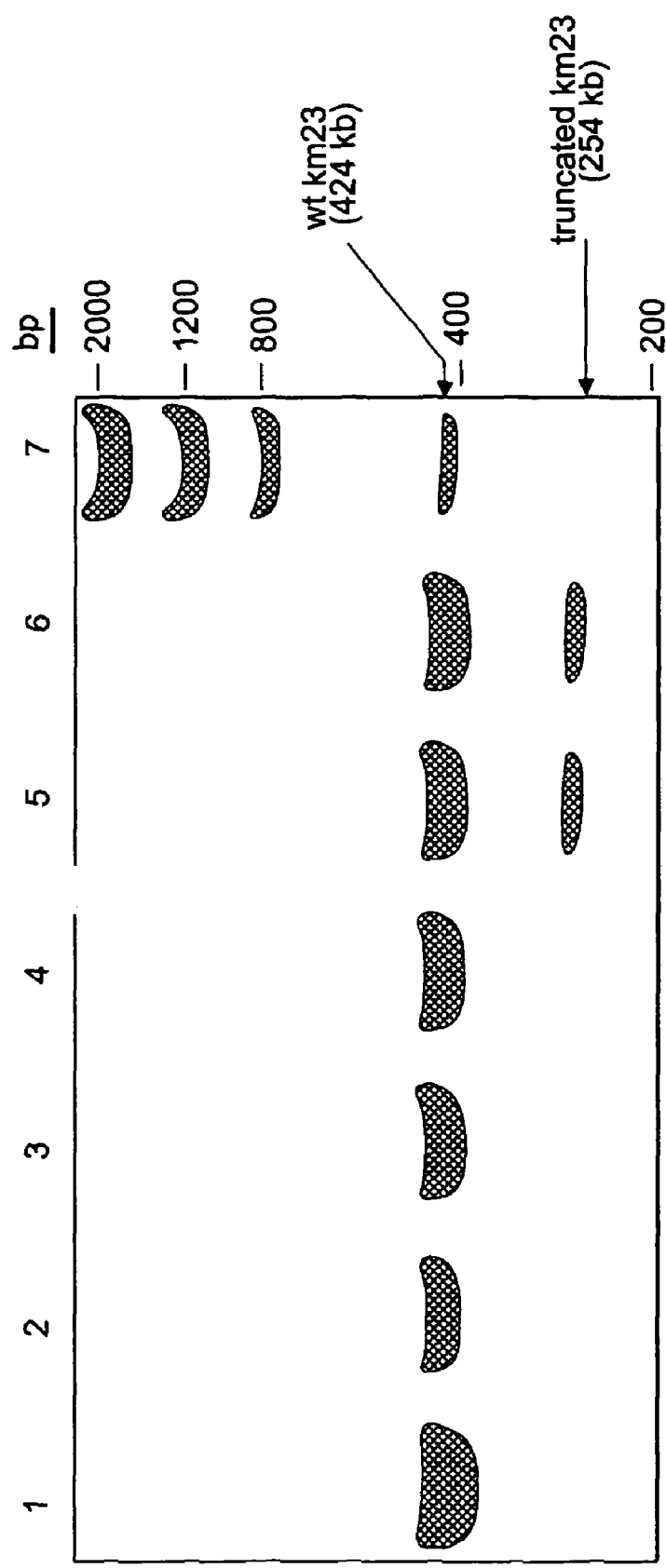
FIG. 8 shows agarose gel analysis of a splicing variant of human km23 polypeptide (truncated form of km23) detected by nested RT-PCR in two out of six human ovarian cancer cell lines which were examined.
Figure 9:
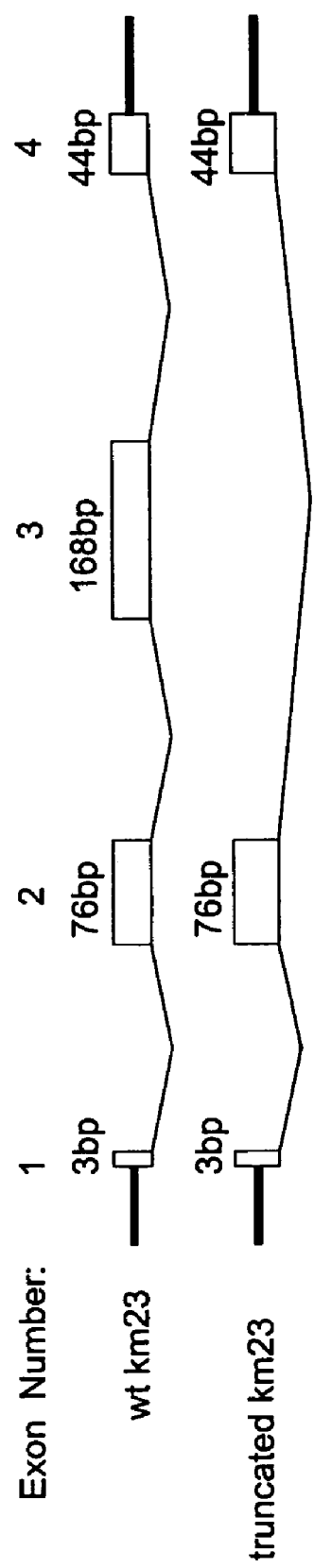
FIG. 9 is a schematic diagram of the positions of the relevant exons of a wt km23 gene aligned above those in the altered km23 gene encoding the truncated form of km23 which is shown in lanes 5 and 6 of FIG. 8, indicating the absence of exon 3 in the truncated form.
Figure 10:
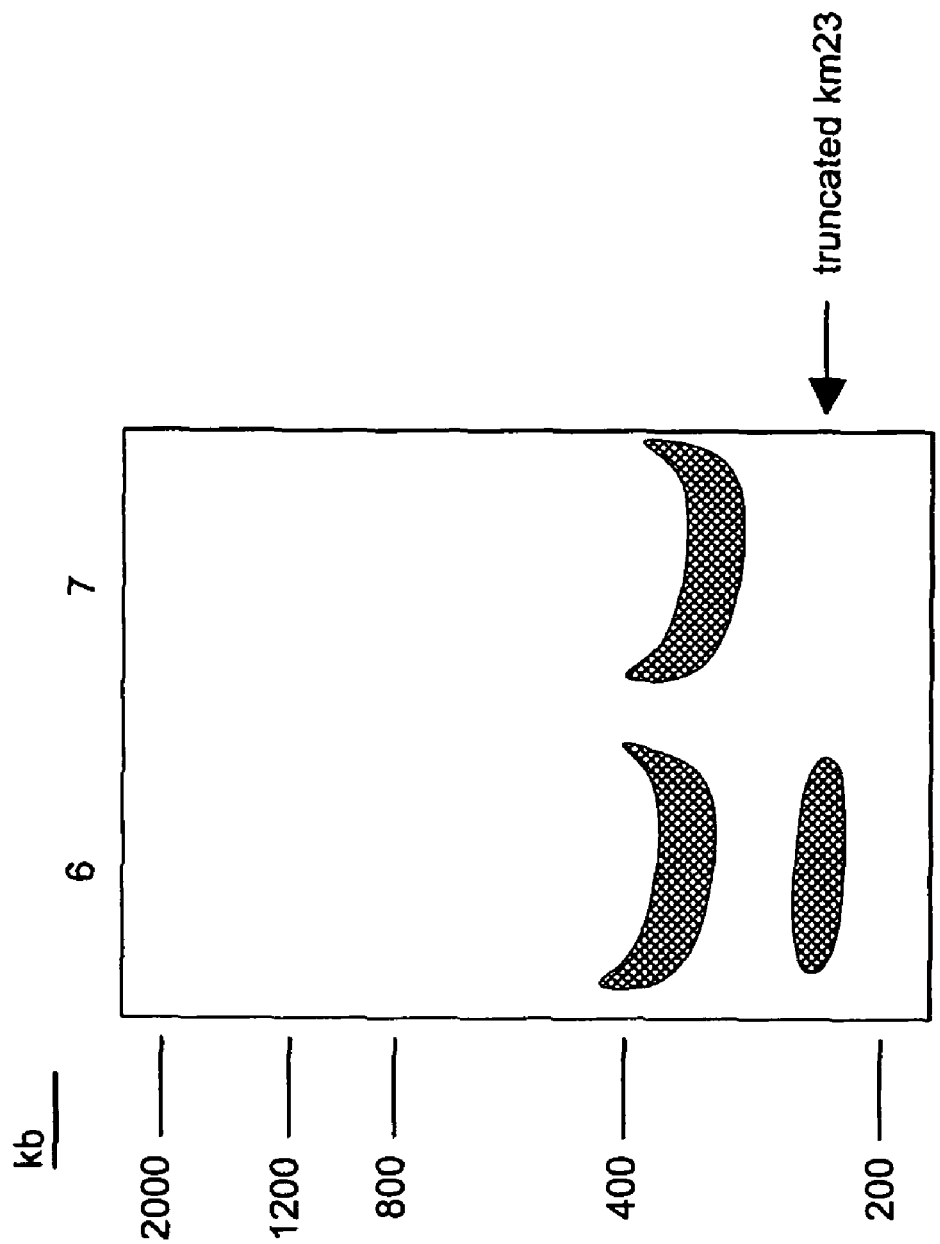
FIG. 10 is an agarose gel analysis of alterations in the wild-type sequence of human km23 nucleic acid which were identified by nested RT-PCR in laser capture microdissected human ovarian cancer tissue samples from patients.

Six human ovarian cancer cell lines were also analyzed by nested RT-PCR and sequenced to identify alterations in the km23 gene using the diagnostic/prognostic screening methods of the present invention. With reference now to FIG. 8, agarose gel analysis of the amplified PCR product indicated the presence of a splicing variant of human km23 which was detectable by nested RT-PCR in two out of six human ovarian cancer cell lines. The splicing variant of km23 (truncated; 254 BP) was found in SK-OV-3 (lane 6) and IGROV-1 cells (lane 5) of the figure. The other ovarian cancer cell lines examined corresponded to OVCA 420 (lane 2), OVCA 429 (lane 1), CaOV 3 (lane 3), and OV-CAR3 (lane 4). The wild-type km23 protein shown in FIG. 8 corresponds to a 424 kb band. Sequence analysis of the truncated form of km23 shown in FIG. 8 illustrated the loss of exon 3 in the ovarian tumor cells. This is illustrated in the schematic diagram of FIG. 9 which shows the relevant exons of km23 aligned above those in the truncated form of km23. This same alteration in human km23 was found in human ovarian cancer tissue samples from patients as shown in FIG. 10. Again, laser capture microdissected tissues were analyzed by nested RT-PCR and sequenced to detect the precise alteration using the diagnostic/prognostic methods of this invention. As shown in FIG. 10, sample 6 contains the splicing variant (truncated form), which is not present in sample 7. However, sequencing of the cDNA of sample 7 indicated that the km23 sequence for this tumor sample codes for a larger protein due to an alteration in the stop codon. This alteration in the stop codon results in a predicted protein of 107 amino acids, as compared to the 96 amino acids of the wild-type form. The elongated protein and a nucleic acid encoding it are provided herein as SEQ ID NO: 6 and SEQ ID NO: 7, respectively.

It is noted that altered forms of km23 such as these described above may interact aberrantly with the TGFβ receptors or the signaling components to cause constitutive signaling. Alternatively, such altered forms may not interact with the receptor or the signaling components as the wild-type protein does. Furthermore, it is noted that altered forms of km23 may not be able to interact or may interact aberrantly with other specific binding partners of km23, such as the dynein intermediate chain (DIC). Experimental evidence of the present inventor detailed below supports the inventor's model that TGFβ receptor activation by TGFβ results in phosphorylation of km23; this causes a conformational change in km23, allowing the C- and N-terminal regions to fold and attach to the DIC. Once this occurs, the cargo (i.e. TGFβ signaling components) can attach to the dynein motor, and move along the microtubule to the appropriate cell location. Cell location is critical for appropriate/efficient cell signaling. If the binding of km23 to the DIC, or the attachment of cargo is altered due to the presence of a variant form of km23, then the signaling components will not move to the proper location, and may either fail to signal, signal constitutively, or signal in a manner unlinked to TGFβ receptor activation. Any of these situations could lead to cancer. It has, in fact, been determined as will be described in further detail below, that the truncated km23 form shown in FIGS. 8 and 10 binds weakly to DIC, as compared to the wild-type form. As described above, this truncated km23 form was found in human ovarian cancer tissue samples and two out of six ovarian cancer cell lines examined by nested RT-PCR.

Based on its role as a mediator of TGFβ activity and further based on the mutational analysis described above, it is likely that the km23 gene acts as a tumor suppressor gene. In fact, the inventor has studies showing that the km23 protein encoded by the km23 gene acts as an inhibitor of cell growth. In particular, it has been found that stable expression in Mv1Lu or MDCK cells of an expression vector carrying the human cDNA sequence for the km23 protein not only resulted in substantial growth inhibition of the cells, relative to the empty vector-transfected control cells, but some of the cell clones stably expressing km23 appear to have undergone either growth arrest or replicative cell senescence. After several weeks in culture, some clones no longer appear to be dividing and cannot be expanded and maintained in culture.

Figure 16:
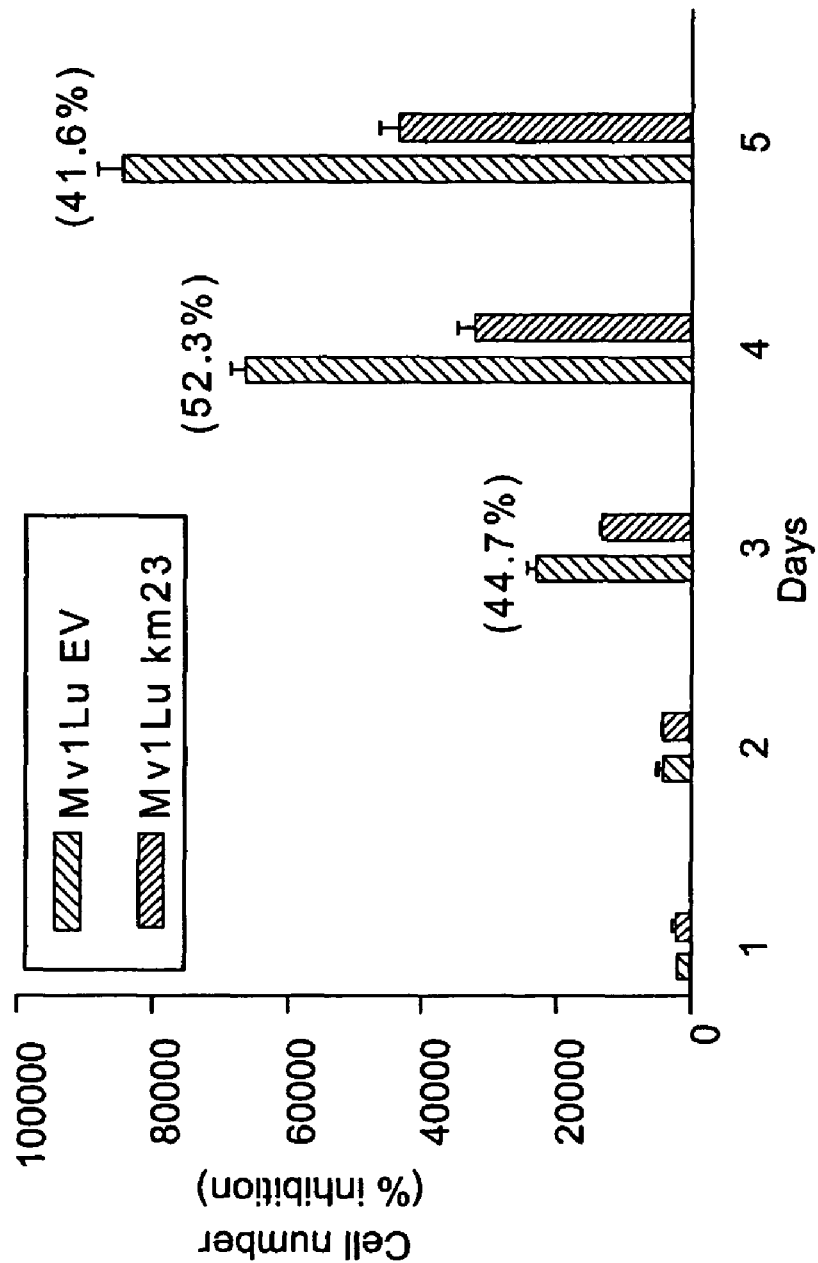
FIG. 16 is a graph showing the percentage of cell growth inhibition associated with stable expression of km23 in Mv1Lu cells as determined by the Crystal Violet Assay.

With reference now to FIG. 16, subsequent studies with Mv1Lu cells which were stably transfected with either MT vector (hatched bars) or GFP-km23-flag (solids bars) indicated that stable expression of km23 inhibits cell growth. In fact, stable expression of km23 resulted in approximately 50% inhibition of the growth of these cells. This indicates that the expression of wild-type km23 results in growth inhibition of epithelial cells, as TGFβ does.

Furthermore, the inventor has preliminary studies indicating a likely role for the km23 protein in TGFβ production (Example 15). Based on the results of a luciferase reporter assay, a mutant form of the km23 polypeptide, which has a valine in place of the arginine at amino acid position 58, appears to inhibit the region of a TGFβ-1 promoter responsible for production. Expression of this mutant appears to inhibit TGFβ induction of this promoter region, as well as basal promoter activity (which reflects autocrine TGFβ). In fact, this particular mutant appears to inhibit by 50% or more both basal and TGFβ-stimulated TGFβ-1 promoter activity. The results of these preliminary studies indicate a likely role of km23 in TGFβ production.

The activation of Jun N-terminal kinase (JNK) and c-Jun by expression of km23 (Tang et al, Molec. Biol. of the Cell, *In Press*, 2002) further supports a role for km23 in TGFβ production (see Example 15.1), since these TGFβ signaling components are required for this effect (Yue and Mulder, 2000; Yue and Mulder, 2001). Similarly, the activation of CRE activity by km23 expression in specific cell types, as well as the synergy between km23 and TGFβ or its receptors in inducing this activity, is likely to contribute to production of TGFβ2 and TGFβ3. The CRE sites in these TGFβ promoters are likely to be important for production of these TGFβ isoforms (Hartsough and Mulder, 1997). Activation of JNK and c-Jun can also lead to activation of CRE sites. Thus, the ability of km23 to activate JNK and c-Jun further supports a role of km23 in production of the TGFβ2 and TGFβ3 isoforms.

Since TGFβ is present everywhere in the body and regulates a diverse array of cellular functions, a km23 polypeptide, mutant or fragment thereof which mediates or modulates TGFβ signals inside the cell is important as a therapeutic target. Any means of altering the expression or activity of km23 family members would have important consequences for TGFβ responses. Accordingly, this invention has applicability related to any need for signal transducers or modulators of TGFβ superfamily members and related uses.

Polypeptides

The present invention provides fragments of the km23 protein. Such fragments are useful as reagents for the screening methods of this invention or for altering TGFβ signal transduction activity. It is well within the contemplation of the present invention that only a fragment of the km23 protein may be required for functional activity. In one embodiment of the present invention, a km23 polypeptide fragment useful in the present invention is of mammal and corresponds to amino acids 1-26 in SEQ ID NO: 1 or SEQ ID NO: 2. In a further embodiment, the fragment may include the amino acids corresponding to amino acids 2-26 in SEQ ID NO: 1 or SEQ ID NO: 2. Further embodiments include fragments corresponding to amino acids 27-82, 83-96 and 27-96, wherein amino acid numbers correspond to those in SEQ ID NO: 1 or SEQ ID NO: 2. These fragments were chosen based on the positions of the exons. For example, with reference to FIG. 1, exon 1 includes only the initiating met, exon 2 comprises amino acids 2-26, exon 3 comprises amino acids 27-82 and exon 4 comprises amino acids 83-96. Of note, is a further inventive fragment comprising a combination of a fragment comprising a combination of (a) the amino acid sequence corresponding to amino acids 1-26 in SEQ ID NO: 1 or SEQ ID NO: 2; and (b) the amino acid sequence corresponding to amino acids 83-96 in SEQ ID NO: 1 or SEQ ID NO: 2, which fragment corresponds to a spliced variant of the km23 protein in a truncated form. As described above, this truncated protein was found in ovarian tissue samples as well as 2 out of 6 ovarian cancer cell lines tested. All of exon 3 is missing from this truncated form (see FIG. 9).

In one embodiment of the invention, the km23 polypeptide fragment interacts with dynein by binding to the dynein intermediate chain (DIC), wherein the interaction with DIC is modulated by TGFβ superfamily members. For example, with reference to Example 11, the truncated km23 lacking amino acids 27-82 interacts weakly with DIC.

The present invention further provides mutant km23 polypeptides. Such mutant km23 polypeptides may alter the function of the TGFβ growth factor signaling pathway. In particular embodiments, the mutant km23 polypeptide is a polypeptide which is selected from the following: (a) a mutant km23 polypeptide having a Gly at the amino acid corresponding to amino acid number 55 of SEQ ID NO: 1 or SEQ ID NO: 2; (b) a mutant km23 polypeptide having a Val at the amino acid corresponding to amino acid number 89 of SEQ ID NO: 1 or SEQ ID NO: 2; (c) a mutant km23 polypeptide having a Ile at the amino acid corresponding to amino acid number 46 of SEQ ID NO: 1 or SEQ ID NO: 2; (d) a mutant km23 polypeptide having a Ser at the amino acid corresponding to amino acid number 56 of SEQ ID NO: 1 or SEQ ID NO: 2; and (e) a mutant km23 polypeptide having an Ala at the amino acid corresponding to amino acid 4 of SEQ ID NO: 1 or SEQ ID NO: 2.

In other embodiments, the mutant km23 polypeptide is a polypeptide selected from the following: (a) a mutant km23 polypeptide having an Ala, Asp, or Glu at the amino acid corresponding to amino acid number 32 of SEQ ID NO: 1 or SEQ ID NO: 2; (b) a mutant km23 polypeptide having a Glu or Asp at the amino acid corresponding to amino acid number 55 of SEQ ID NO: 1 or SEQ ID NO: 2; (c) a mutant km23 polypeptide having a Ala, Glu, or Asp at the amino acid corresponding to amino acid number 73 of SEQ ID NO: 1 or SEQ ID NO: 2; (d) a mutant km23 polypeptide having a Ala, Asp, or Glu at the amino acid corresponding to amino acid number 7 of SEQ ID NO: 1 or SEQ ID NO: 2; (e) a mutant km23 polypeptide having a Ala, Asp, or Glu at the amino acid corresponding to amino acid number 33 of SEQ ID NO: 1 or SEQ ID NO: 2; (f) a mutant km23 polypeptide having a Ala, Asp, or Glu at the amino acid corresponding to amino acid number 56 of SEQ ID NO: 1 or SEQ ID NO: 2; and (g) a mutant km23 polypeptide having an Ala or Glu at the amino acid corresponding to amino acid number 13 of SEQ ID NO: 1 or SEQ ID NO: 2. These alterations occur at potential phosphorylation sites (see FIG. 1) and may affect km23 function.

The invention further provides for a fusion protein including any of the km23 polypeptides, fragments or mutants of this invention, and a second polypeptide having an amino acid sequence unrelated to the amino acid sequence of the km23 polypeptide. For example, in one desired embodiment, the second polypeptide functions as a detectable label for detecting the presence of the fusion protein or as a matrix-binding domain for immobilizing the fusion protein.

Further encompassed within the present invention is a cloned nucleic acid molecule encoding the fusion protein described above.

The invention includes functional equivalents of the km23 polypeptide forms of this invention, including the fragments and mutants described above. Desirably, a protein or fragment is a functional equivalent if its amino acid sequence is at least approximately 60% identical, preferably at least approximately 70% identical. However, the percent identity may be considerably lower than this based on the percent identity of related robl62A (24%), robl37BC (23%) and *Drosophila* bithoraxoid (bxd) (23%).

It is preferred that the km23 polypeptides, mutants or fragments thereof are derived from a mammalian species. Mammals include laboratory animals, such as rats, mice, and rabbits; farm animals, such as cows, pigs, horses and sheep; pet animals, such as dogs and cats; and primates, such as monkeys, orangutans, apes, and humans.

The preferred mammals include mice or humans. The km23 polypeptides and protein fragments are preferably isolated. By the term isolated it is meant that the km23 polypeptides or fragments thereof is partially purified or purified to homogeneity. The protein is considered partially purified if it as at least 25%, preferably at least approximately 50%, more preferably at least approximately 75%, most preferably at least approximately 90% and optimally at least approximately 95% free of other proteins. The polypeptide or polypeptide fragment is considered to be purified to homogeneity if it exhibits a single band by SDS page.

Cloned Nucleic Acid Molecules

The present invention also provides for km23 nucleic acid forms which encode the km23 polypeptides, fragments and mutants of this invention.

In one desired embodiment, a nucleic acid of this invention includes a 5' or 3' regulatory sequence. Desirably, the regulatory sequence is operably linked to nucleotide sequence encoding the km23 polypeptide or fragment thereof. In one embodiment, the nucleic acid form would desirably encode a km23 polypeptide or fragment which modulates the intracellular signal transduction pathways mediated by TGFβ superfamily members. It is desired that the nucleic acid form is derived from a mammal, preferably a human.

In various embodiments, the nucleic acid forms of the present invention encode particular fragments of the km23 protein, such as those corresponding to the following amino acids in SEQ ID NO: 1 or SEQ ID NO: 2: 1-26, 2-26, 27-82, 83-96, 2-82, 27-96, and a fragment including a combination of (a) the amino acid sequence corresponding to amino acids 1-26; and (b) the amino acid sequence corresponding to amino acids 83-96.

A further cloned km23 nucleic acid form encompassed by the present invention is shown in the formula of SEQ ID NO: 7, which encodes an elongated km23 protein having SEQ ID NO: 6.

Also included within the scope of the present invention are altered nucleic acid sequences encoding km23 polypeptide or a fragment thereof. Such alterations may include, but are not limited to, deletions, insertions, or substitutions of different nucleotides resulting in a nucleic acid form that encodes the same or a functionally equivalent km23 protein. To this end, the encoded protein may also contain deletions, insertions, or substitutions of amino acid residues which produce a silent change and results in a functionally equivalent km23 protein. Such altered nucleic acid sequences and their encoded proteins may be useful for therapeutic purposes.

Also included within the scope of the invention are altered nucleic acid sequences resulting from at least one mutation in a nucleic acid sequence, which altered nucleic acid sequences may result in a polypeptide whose structure or function is altered. Such altered nucleic acid forms and the polypeptides resulting from them may be useful in the area of diagnosis of a particular disorder or design of therapeutic agents against such a disorder. This is further described below.

In one embodiment, a cloned mutant km23 nucleic acid form is a mutant characterized by a mutation of at least one nucleotide base relative to a wild-type km23 nucleic acid form, which mutation results in a mutant km23 polypeptide selected from the group of mutant km23 polypeptides having the following amino acid changes, which correspond to the amino acid number in SEQ ID NO: 1 or SEQ ID NO: 2: (a) a mutant km23 polypeptide having a Gly at the amino acid corresponding to amino acid number 55 of SEQ ID NO: 1 or SEQ ID NO: 2; (b) a mutant km23 polypeptide having a Val at the amino acid corresponding to amino acid number 89 of SEQ ID NO: 1 or SEQ ID NO: 2; (c) a mutant km23 polypeptide having a Ile at the amino acid corresponding to amino acid number 46 of SEQ ID NO: 1 or SEQ ID NO: 2; (d) a mutant km23 polypeptide having a Ser at the amino acid corresponding to amino acid number 56 of SEQ ID NO: 1 or SEQ ID NO: 2; and (e) a mutant km23 polypeptide having an Ala at the amino acid corresponding to amino acid 4 of SEQ ID NO: 1 or SEQ ID NO: 2.

In another embodiment, the mutation in the km23 nucleic acid form occurs at a potential phosphorylation site, the mutation resulting in a mutant km23 polypeptide selected from the following: (a) a mutant km23 polypeptide having an Ala, Asp, or Glu at the amino acid corresponding to amino acid number 32 of SEQ ID NO: 1 or SEQ ID NO: 2; (b) a mutant km23 polypeptide having a Glu or Asp at the amino acid corresponding to amino acid number 55 of SEQ ID NO: 1 or SEQ ID NO: 2; (c) a mutant km23 polypeptide having a Ala, Glu, or Asp at the amino acid corresponding to amino acid number 73 of SEQ ID NO: 1 or SEQ ID NO: 2; (d) a mutant km23 polypeptide having a Ala, Asp, or Glu at the amino acid corresponding to amino acid number 7 of SEQ ID NO: 1 or SEQ ID NO: 2; (e) a mutant km23 polypeptide having a Ala, Asp, or Glu at the amino acid corresponding to amino acid number 33 of SEQ ID NO: 1 or SEQ ID NO: 2; (f) a mutant km23 polypeptide having a Ala, Asp, or Glu at the amino acid corresponding to amino acid number 56 of SEQ ID NO: 1 or SEQ ID NO: 2; and (g) a mutant km23 polypeptide having an Ala or Glu at the amino acid corresponding to amino acid number 13 of SEQ ID NO: 1 or SEQ ID NO: 2.

It is noted that nucleic acid forms encompassed by this invention include, but are not limited to, all functional equivalents of any of the sequences described above. For example, a nucleic acid form would be a functional equivalent if its nucleic acid sequence is at least approximately 60% identical, preferably at least approximately 70% identical; most preferably at least approximately 80% identical, especially preferably at least approximately 90% identical, optimally at least approximately 95% identical, and especially optimally at least approximately 98% identical. Percent identity between the two strands of sequences is calculated by juxtaposing the two strands so as to achieve the highest possible identity of residues. Software is available to aid in the alignment.

Preparing km23 Polypeptides and Fragments Thereof

The km23 polypeptides, mutated versions or fragments of either provided by this invention, and DNA encoding the same may be chemically synthesized by methods known in the art. Suitable methods for synthesizing polypeptides are described by Stuart and Young in "Solid Phase Peptide Synthesis," Second Edition, Pierce Chemical Company (1984), Solid Phase Peptide Synthesis, Methods Enzymol., 289, Academic Press, Inc, New York (1997). Suitable methods for synthesizing DNA are described by Caruthers in Science 230:281-285 (1985) and DNA Structure, Part A: Synthesis and Physical Analysis of DNA, Lilley, D. M. J. and Dahlberg, J. E. (Eds.), Methods Enzymol., 211, Academic Press, Inc., New York (1992). The subject matter of all of the aforementioned citations are incorporated herein by reference.

Polypeptides may also be prepared by providing DNA that encodes the protein fragment; amplifying or cloning the DNA in a suitable host; expressing the DNA in a suitable host; and harvesting the protein. For example, the km23 protein or a fragment thereof may be translated either directly or indirectly from a cDNA encoding km23 amino acid sequence.

The DNA encoding polypeptides of the invention may be replicated and used to express recombinant protein following insertion into a wide variety of host cells in a wide variety of cloning vectors.

Cloning vectors may comprise segments of chromosomal, non-chromosomal, and synthetic DNA sequences. Some suitable prokaryotic cloning vectors include plasmids from *E. coli*, such as col E1, pCR 1, pBR 322, pMB9, pUC, pKSM, and RP4. Prokaryotic vectors also include derivatives of phage DNA such as M13 fd and other filamentous single-stranded DNA phages.

The host may be prokaryotic or eukaryotic. The DNA may be obtained from natural sources and, optionally, modified by, for example, site-specific mutagenesis. The genes may also be synthesized from the individual nucleotides in whole or in part. Synthetic methods, such as solid phase methods, are known in the art, such as those described by Caruthers in Science v. 230, pp 281-285 (1985) and DNA Structure Part A: Synthesis and Physical Analysis of DNA, Lilley, D. M. J. and Dahlberg, J. E. (Eds.), Methods Enzymol, v. 211, Academic Press, NY (1992).

The invention provides for an expression vector capable of expressing in a host cell any of the km23 polypeptides, mutant km23 polypeptides, or km23 fragments described above. Vectors for expressing proteins in bacteria, especially *E. coli*, are also known. Such vectors include the pK 233 (or any of the tac family of plasmids), T7, pBluescript II, bacteriophage lambda, ZAP, and lambda $P_L$ (Wu, R. (Ed.), *Recombinant DNA Methodology II, Methods in Enzymol.*, Academic Press, Inc., N.Y., (1995). Examples of vectors with expressed fusion proteins are PATH vectors described by Dieckmann and Tzagoloff in J. Biol. Chem., vol. 260, 1513-1520 (1985). These vectors contain DNA sequences that encode anthranilate synthetase (TrpE) followed by a poly-linker at the carboxy terminus. Other expression vector systems are based on beta-galactosidase (pEX); maltose binding protein (pMAL); glutathione-S-tranferase (PGST or pGEX)—see Smith, D. B. Methods Mol. Cell Biol., vol. 4: pp 220-229 (1993); Smith, D. B. and Johnson, K. S., Gene, vol. 67, pp 31-40 (1988); and Peptide Res., vol. 3; 167 (1990), and TRX (thioredoxin)

Fusion Protein (TRX FUS)—see La Vallie, R. et al., Bio/Technology, vol. 11, pp 187-193 (1993).

Vectors useful for cloning and expression in yeast are available. Suitable examples are 2 µm circle plasmid, Ycp50, Yep24, Yrp7, Yip5, and pYAC3 (Ausubel, F. M. et al. (Eds.), Current Protocols in Molecular Biology, John Wiley & Sons, Inc., New York, (1999)).

Suitable cloning/expression vectors for use in mammalian cells are also known. Such vectors include well-known derivatives of SV-40, adenovirus, cytomegalovirus (CMV) retrovirus-derived DNA sequences. Any such vectors, when coupled with vectors derived from a combination of plasmids and phage DNA, i.e. shuttle vectors, allow for the isolation and identification of protein coding sequences in prokaryotes.

Further eukaryotic expression vectors are known in the art (e.g., P. J. Southern and P. Berg, J. Mol. Appl. Genet. 1:327-341 (1982); S. Subramani et al, Mol. Cell. Biol. 1:854-864 (1981); R. J. Kaufmann and P. A. Sharp, "Amplification And Expression Of Sequences Cotransfected with A Modular Dihydrofolate Reductase Complementary DNA Gene," J. Mol. Biol. 159:601-621 (1982); R. J. Kaufmann and P. A. Sharp, Mol. Cell. Biol. 159:601-664 (1982); S. I. Scahill et al, "Expression And Characterization Of The Product Of A Human Immune Interferon DNA Gene In Chinese Hamster Ovary Cells," Proc. Natl. Acad. Sci. USA 80:4654-4659 (1983); G. Urlaub and L. A. Chasin, Proc. Natl. Acad. Sci. USA 77:4216-4220 (1980).

It is noted that expression and cloning vectors will likely contain a selectable marker, a gene encoding a protein necessary for survival or growth of a host cell transformed with the vector. The presence of this gene insures growth of only those host cells which express the insert. Typical selection genes encode proteins that: (a) confer resistance to antibiotics or other toxic substances (e.g. ampicillan, neomyicin, methotrexate, etc.); (b) compliment auxotrophec deficiencies or (c) supply critical nutrients not available from complex media, e.g. gene encoding d-alanine, racenase for Basillia. The choice of the proper selectable marker will depend on the host cell, and appropriate markers for different hosts are well known in the art.

The expression vectors useful in the present invention contain at least one expression control sequence that is operatively linked to the DNA sequence or fragment to be expressed. The control sequence is inserted in the vector in order to control and to regulate the expression of the cloned DNA sequence. Examples of useful expression control sequences are the lac system, the trp system, the tac system, the trc system, the tet system, major operator and promoter regions of phage lambda, the control region of fd coat protein, the glycolytic promoters of yeast, e.g., the promoter for 3-phosphoglycerate kinase, the promoters of yeast acid phosphatase, e.g., Pho5, the promoters of the yeast alpha-mating factors, and promoters derived from polyoma, adenovirus, retrovirus, and simian virus, e.g., the early and late promoters or SV40, and other sequences known to control the expression of genes of prokaryotic or eukaryotic cells and their viruses or combinations thereof.

Once the gene is cloned into such an expression vector, the gene product may be produced in a suitable expression host in either a constitutive or inducible manner. Useful expression hosts include well-known prokaryotic and eukaryotic cells. Some suitable prokaryotic hosts include, for example, E. coli, such as E. coli SG-936, E. coli HB 101, E. coli W3110, E. coli X1776, E. coli X2282, E. coli DH1, E. coli DH5αF', and E. coli MRCl, Pseudomonas, Bacillus, such as Bacillus subtilis, and Streptomyces. Suitable eukaryotic cells include yeasts and other fungi, insect, animal cells, such as COS cells and CHO cells, human cells and plant cells in tissue culture.

The invention provides for a host cell transfected with the expression vector of the present invention, which host cell is capable of expressing a km23 polypeptide, or a fragment thereof.

Host cells which contain the nucleic acid sequence encoding km23 and express km23 may be identified by a variety of procedures known to those skilled in the art. These procedures include, but are not limited to, DNA-DNA or DNA-RNA hybridization and protein bioassay or immunoassay techniques which include membrane and solution based technologies for the detection and/or quantification of nucleic acid or proteins.

The polypeptides/fragments of this invention may be purified using standard known techniques. Some examples of suitable techniques include, for example, gel purification, column chromatography, or electrophoretic methods. Recombinant constructions may be used to join sequences encoding km23 to nucleic acid sequence encoding a polypeptide domain which will facilitate purification of soluble proteins. Such purification facilitating domains include, but are not limited to, metal chelating peptides such as histidine-tryptophan modules that allow purification on immobilized metals, protein A domains that allow purification or immobilized immunoglobulin, and the domain utilized in the flags-extension/affinity purification system (Immunex Corp., Seattle, Wash.). Moreover, signal sequences may be used to facilitate the export of km23 into a cell culture supernatant to facilitate purification of the protein.

As described above, the expression vector according to this invention allows for the translation of protein domains which are capable of facilitating the function of km23 to affect various cellular processes associated with the TGFβ signaling pathway, including, but not limited to, inhibiting cellular proliferation.

In one embodiment of the present invention, the km23 polypeptide, fragment, or mutant thereof which is expressed is capable of modulating intracellular signal transduction pathways mediated by TGFβ superfamily members. In a particular embodiment of the expression vector, the km23 polypeptide, fragment, or mutant version thereof which is expressed is capable of modulating at least one of the following: regulation of gene expression, cell growth, cell differentiation, cell survival, apoptosis, senescence, cell migration, angiogenesis, fibrosis, wound healing, extracellular matrix induction, adhesion, autoproduction, embryogenesis and combinations thereof. As described above, km23 protein mediates TGFβ signals inside the cell. This is clearly illustrated in the examples below. To this end, since TGFβ is found everywhere in the body and regulates a diverse array of cellular functions, including those described, any means of altering the expression or activity of km23 or km23 functional analogs has important consequences for TGFβ responses.

In a further embodiment of the present invention, an expression vector according to this invention, which expresses a km23 polypeptide, km23 protein fragment, or a mutant form of km23, is capable of modulating at least one of the following: actin cytoskeleton dynamics, microtubule dynamics, intracellular transport, cell polarity, dynein-mediated microtubule transport and combinations thereof. As illustrated by Example 10 shown below, km23 has been shown to interact with dynein in MDCK cells, which are a type of canine kidney cell type. Based on this association and the fact that km23 is a dynein LC, km23 polypeptides are expected to have an effect on any one of actin cytoskeleton dynamics, microtubule dynamics, intracellular transport, cell polarity, dynein-mediated microtubule transport and combinations thereof. For example, dynein's role in these various functions have been previously established by others (see for example Hirokawa, 1998).

As described above, dynein is a molecular motor protein which mediates intracellular transport; it conveys its cargo along polarized microtubules towards the minus ends. Dynein appears to control various cell functions which include axonal transport, flagellar motility, organization of the mitotic spindle, distribution of late endosomes and lysosomes, the centrosomal localization of the Golgi complex, vesicular transport from early to late endosomes, the apical transport of Golgi-derived membranes in intestinal epithelial cells, the movement of phagosomes, and others as reviewed in Hirokawa, 1998.

Figure 6A:
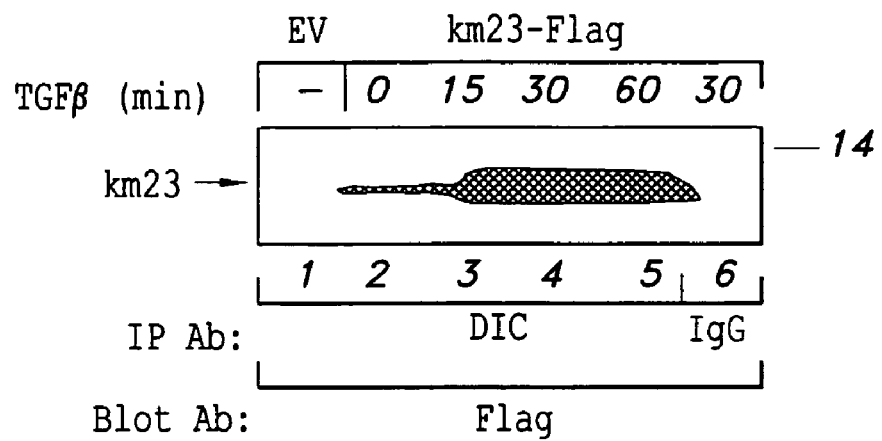
FIG. 6. Interaction of km23 with the dynein intermediate chain (DIC) in MDCK cells. MDCK cells were transiently transfected with either empty vector or km23-flag. 36 h after transfection, cells were treated with TGFβ for various time points and then lysed. Cell lysates were subjected to immunoprecipitation using a monoclonal anti-DIC Ab, followed by immunoblot analysis using an anti-flag Ab (A). Cell lysates were then blotted with anti-flag (B) or anti-DIC (C) as controls for expression. The presence of the km23 bands in lanes 2-5 (A) indicates that dynein and km23 interact in all samples in which km23 was expressed, and that TGFβ increases this interaction (lanes 3-5).
Figure 6B:
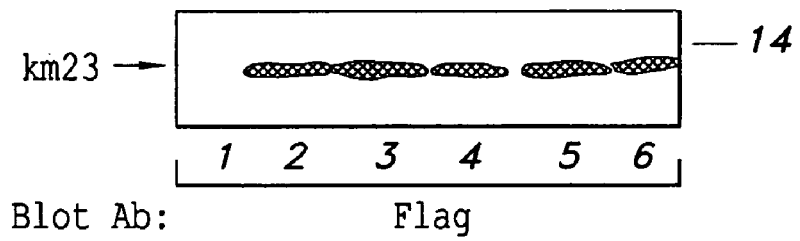
Figure 6C:
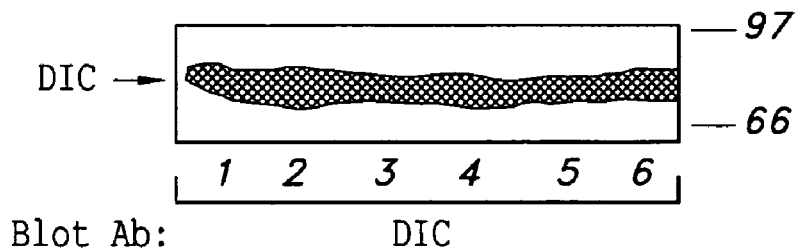

The inventor's finding that TGFβ can regulate km23 protein, a member of the dynein-associated proteins, and thereby control dynein motoring along microtubules towards the minus ends, demonstrates a novel function for TGFβ in microtubule dynamics. Microtubules are polar structures with a fast-growing plus end and a minus end. They function as "rails" for the transport of organelles via microtubule-associated motor proteins such as dynein. Microtubules are important for many cellular processes, and play an important role in the generation and maintenance of epithelial cell polarity (Hofer et al., 1998). The inventor has established that km23 plays a role in dynein functions in polarized epithelial cells, such as the Madin-Darby canine kidney (MDCK) cells as shown below in the examples and as illustrated in FIG. 6.

Oligonucleotides and Primers

In yet another aspect of the present invention, a substantially pure oligonucleotide or primer is provided, wherein the oligonucleotide or primer includes a region of nucleotide sequence capable of hybridizing under stringent conditions to at least about 12 consecutive nucleotides of sense or anti-sense sequence of any of the mutant km23 nucleic acid forms provided by this invention. Also encompassed by the present invention are oligonucleotides or primers such as those described above wherein the oligonucleotide or primer further includes a detectable label attached thereto.

There is no upper limit to the length of the oligonucleotide probes or primers. However, normally, the oligonucleotide probe will not contain more than 50 nucleotides, preferably not more than 40 nucleotides, and more preferably not more than 30 nucleotides.

The oligonucleotides and primers provided by the present invention may be useful for diagnosing a particular disorder, such as by PCR amplification of portions of the km23 nucleotide sequence which may harbor a mutation, insertion, or deletion of a nucleotide base, as one example. Moreover, the probe and primers provided herein may be used as part of anti-sense therapy. This is further described below and relates to a potential therapeutic use of such oligonucleotides or primers.

Kits for Diagnostic or Prognostic Screening

The present invention provides kits useful for diagnostic or prognostic screening of a km23 nucleic acid sample.

For example, the invention provides a kit useful for nested RT-PCR analysis of a km23 RNA form from a patient sample. The RNA sample is desirably isolated from snap-frozen LCM microdissected tissues or cnaps. The kit includes at least the following components: (a) a first pair of PCR primers comprising SEQ ID NO:20 and SEQ ID NO:21; (b) a second pair of PCR primers comprising SEQ ID NO:22 and SEQ ID NO:23; (c) a negative control comprising a wild-type km23 cDNA; and (d) a positive control comprising a km23 mutant cDNA. A useful positive control is the km23 nucleic acid form identified by the present inventor which encodes a truncated km23 protein form which lacks amino acids 27-82 of SEQ ID NO: 1 or SEQ ID NO: 2. Other useful kit components which may be included are the following: reverse transcripase; Pfu polymerize, and RNA isolation components.

Other diagnostic or prognostic kits are also well within the scope of this invention. For example, this invention encompasses nested PCR kits for amplification of individual exons of a km23 nucleic acid patent sample. Nested PCR would be carried out on DNA which had been isolated from LCM microdissected tissues or which had been extracted from serum and plasma samples to obtain cnaps. One useful kit for screening of exon 2 includes: (a) a first set of primers comprising SEQ ID NO: 12 and SEQ ID NO:13; (b) a second set of PCR primer comprising SEQ ID NO:14 and SEQ ID NO: 15; (c) a negative control comprising wild type km23 cDNA; and (d) a positive control comprising a km23 mutant cDNA having an alteration within the relevant exon.

Similar nested PCR kits are contemplated by this invention for amplification of exon 3 or exon 4 that would include the relevant primers indicated in Example 14. Furthermore, it is contemplated that a single kit may contain the components necessary for analysis of each of the individual exons.

Method of Modulating Intracellular Signal Transduction Pathways Mediated by TGFβ

A method of modulating signal transduction pathways mediated by the TGFβ superfamily members is provided by the present invention, wherein the method includes introducing into the cell a km23 polypeptide, fragment thereof, or mutant form of either.

In another embodiment of this method, the km23 polypeptide is introduced into the cell by expressing in the cell a nucleic acid molecule that encodes a km23 polypeptide. Alternatively, the km23 polypeptide may be introduced into the cell by contacting the cell with the polypeptide or a nucleic acid form encoding the polypeptide.

Active km23 molecules can be introduced into cells by micro-injection or by use of liposomes, for example, alternatively, some active molecules may be taken up by cells, actively or by diffusion. Extracellular application of the km23 polypeptide can, in this instance, be sufficient to effect cell growth.

Desirably, the km23 polypeptide for use in the method described above is of a mammal and most desirably is of a human. In one desired embodiment, the km23 polypeptide includes approximately amino acids 1 to the C-terminus. For example, one useful polypeptide would be the human km23 protein represented in SEQ ID NO: 1. A further useful polypeptide would be that represented by SEQ ID NO: 2. The method above further encompasses the use of a km23 protein fragment provided by this invention. For example, fragments of the protein which may be useful in the method described above include the following peptide fragments, wherein the numbering corresponds to the amino acid sequence shown in SEQ ID NO: 1 or SEQ ID NO: 2: 1-26, 2-26, 27-82, 83-96, 27-96 and a fragment comprising a combination of (a) the amino acid sequence corresponding to amino acids 1-26 in SEQ ID NO: 1 or SEQ ID NO: 2; and (b) the amino acid sequence corresponding to amino acids 83-96 in SEQ ID NO: 1 or SEQ ID NO: 2.

As described above, the experimental results incorporated herein support the role of km23 protein as an inhibitor of cell growth. Therefore, in one desired embodiment, the cell into which the km23 polypeptide or a functional analog thereof is introduced is a malignant cell. In one embodiment, the cell is a carcinoma. In another embodiment, the cell is an osteocarcinoma, sarcoma, osteosarcoma, glioma, melanoma, myxoma, adenoma, rhabdomyoma-derived cell, or pre-malignant versions thereof. Moreover, the cell may be a lung, breast, colon, prostate, kidney, ovary, liver, testes, skin, heart, pancreas, thyroid, adrenal, pituitary, brain, muscle, uterine or bone cell. The cell may be a metastasized cell. Moreover, the cell may be either a post-embryonic cell or an embryonic cell.

The present invention further encompasses a method of modulating the intracellular signal transduction pathways mediated by TGFβ superfamily members, the method including introducing into the cell an antagonist of a km23 nucleic acid form, inclusive of mutant forms, or an antagonist of amino acids encoded by the nucleic acid form. Antagonists of both nucleic acid and protein forms of km23 provide a means by which this TGFβ signaling intermediate may be controlled both at a nucleic acid and protein level. In one embodiment, the antagonist of the km23 nucleic acid form is an anti-sense construct. In a further embodiment, the antagonist of the km23 nucleic acid form is a peptide antagonist. For example, the peptide antagonist can effect a change in the cellular localization of the km23 protein.

Moreover, antagonists of amino acids encoded by the km23 nucleic acid form include a dominant negative version of the km23 protein or a hormone-inducible or drug-inducible version thereof. In one example, tumor tissue such as ovarian tumor tissue is injected with DNA or RNA, such as mRNA, which, when translated, forms an inactive version of the km23 protein capable of blocking the ability of km23 wild-type protein to mediate TGFβ signal transduction activity. Given the inventor's preliminary data suggesting that km23 is a potent inhibitor of cell growth, translation of a dominate negative version of the km23 protein would be expected to block the ability of TGFβ to inhibit the growth of the cells. If this occurs in cancer patients that express a mutant form of km23 in their cells, then the expressed mutant dominate-negative form can be used as a screen to identify therapeutics for such patients.

In a further embodiment, the antagonists of amino acids encoded by the km23 nucleic acid form is a monoclonal antibody. The monoclonal antibody provided herein is further described below.

In a preferred embodiment, the antagonist is a therapeutic agent that modulates the interaction of a km23 polypeptide or mutant form thereof with the dynein intermediate chain. This is described in further detail below.

Antibodies

This invention provides antibodies, preferably monoclonal antibodies that bind specifically to an antigenic determinant in a mutant km23 polypeptide. In one embodiment, the mutant km23 polypeptide form functions in a growth factor or cytokine signaling pathway.

Monoclonal antibodies may be produced by methods known in the art. These methods include the immunological method described by Kohler and Millstein in Nature vol. 256, pp 495-497 (1975) and by Campbell in "Monoclonal Antibody Technology", The Production And Characterization Of Rodent And Human Hybridomas" in Burdon, et al. (Eds.), Laboratory Techniques in Biochemistry and Molecular Biology, vol. 13, Elsevier Science Publishers, Amsterdam (1985); and Coligan, J. E., et al. (Eds.), Current Protocols In Immunology, Wiley Intersciences, N.Y., (1999); as well as recombinant DNA methods described by Huse, et al., Science, vol. 246, pp 1275-1281 (1989). The recombinant DNA method preferably comprises screening phage libraries for human antibody fragments.

In order to produce monoclonal antibodies, a host mammal is inoculated with a km23 peptide or peptide fragment as described above, and then boosted. Spleens are collected from inoculated mammals a few days after the final boost. Cell suspensions from the spleens are fused with a tumor cell in accordance with the general method described by Kohler and Millstein in Nature, vol. 256, pp 495-497 (1975).

If the fragment is too short to be immunogenic, it may be conjugated to a carrier molecular. Some suitable carrier molecules include key hold limpet, hemocyanin and bovine serum albumin. Conjugation may be carried out by methods known in the art (Coligan, J. E., et al. (Eds.), Current Protocols In Immunology, Chapter 9, Wiley Intersciences, N.Y., (1999). One such method is to combine a cysteine residue of the fragment with a cysteine residue on the carrier molecule.

Methods of Use: Gene Therapy

As described above, nested RT-PCR analysis of human ovarian tumor specimens indicates that mutations of km23 nucleic acid forms are associated with disorders of cell proliferation, and in particular, cancer. Accordingly, the present invention encompasses a method of supplying a functional km23 nucleic acid form of this invention to a cell which carries a mutated form of a gene.

For example, part of the km23 gene may be introduced into the cell in a vector such that the gene remains extrachromosomal. More preferred, is a situation where the part thereof is introduced into the mutant cell in such a way that it recombines with the endogenous mutant km23 gene present in the cell. Methods for introducing DNA into cells such as electroporation, calcium phosphate coprecipitation, lipofectamine, and viral transduction are known in the art.

A km23 nucleic acid form or fragment thereof of this invention, where applicable, may be employed in gene therapy methods in order to increase the amount of the expression products of such forms. Such gene therapy may be particularly appropriate for use in both cancers and pre-cancer cells in which the level of a functional km23 polypeptide is absent or diminished compared to normal cells.

Gene therapy is carried out according to generally accepted methods, for example, as described by Friedman in Therapy for Genetic Disease, T. Friedman, Ed., Oxford University Press 1991, pp 105-121.

Anti-sense polynucleotide sequences are useful to modulate km23 activity or to achieve regulation of gene function. To this end, anti-sense to nucleic acid sequence encoding an altered km23 protein may be used in situations in which it would be desirable to block the transcription of the mRNA. In particular, cells may be transformed with sequences complimentary to nucleic acid sequences encoding the km23 form. Such technology is now well known in the art, and sense or anti-sense oligomers or larger fragments, can be designed for various locations along the coding or control regions of sequences encoding km23.

Methods of Use: Peptide Therapy

Polypeptides or fragments of this invention which have km23 activity can be supplied to cells which carry an altered km23 gene. A polypeptide can be produced by expression of cDNA sequence in bacteria, for example, using known expression vectors described above. Alternatively, km23 polypeptide forms can be extracted from km23-producing mammalian cells. Moreover, the techniques of synthetic chemistry can be employed to synthesize km23 polypeptide forms. The preparation used for peptide therapy is substantially free of other human proteins. This can be most readily accomplished by synthesis of the polypeptide in a microorganism or in vitro. The preparation is a pharmaceutical composition.

Methods of Use: Diagnostics and Prognostics

The present invention provides methods for determining the presence or absence of a lesion in a patient specimen which is characterized by a specific alteration in sequence of a km23 nucleic acid or polypeptide form. Such methods can be both diagnostic and prognostic.

Preferred diagnostic and prognostic methods of this invention employ oligonucleotides designed from the sequences encoding km23 protein and involve the use of PCR. Such oligomers may be chemically synthesized by methods described above. Moreover, such oligonucleotides may be generated enzymatically or produced from a recombinant source. Oligomers will preferably consist of two nucleotide sequences, one with sense orientation and another with antisense orientation, employed under optimized conditions for identification of a specific gene or condition. The specific oligomers may be employed for the detection and/or quantitation of closely related DNA or RNA sequences.

In a particular aspect, primer pairs of the present invention are useful for determination of the nucleotide sequence of a particular altered form of the km23 gene using PCR. The pairs of single-stranded DNA primers can be annealed to sequences within or surrounding the km23 gene in order to amplify DNA sequence of the km23 gene itself. A complete set of these primers allows synthesis of all of the nucleotides of the km23 gene coding sequences, that is, the exons. The set of primers preferably allows synthesis of both intron and exon sequences. Mutation-specific primers can also be used, wherein such primers anneal only to particular km23 mutant genes, and thus will only amplify a product in the presence of the mutant gene as a template.

Figure 11:
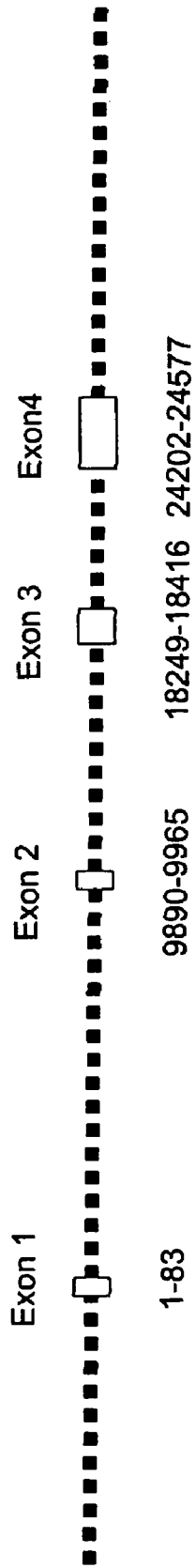
FIG. 11 is a schematic representation of the positioning of exons 1-4 of the human km23 genomic sequence having GenBank Accession Number 16195178, except that the numbering of the nucleotides in the present figure differs from the GenBank genomic sequence by the addition of 34 base pairs; these 34 bps correspond to an extra region at the 5'-end of the 5'-UTR which was identified by the present inventor and is shown in FIG. 1.
Figure 12:
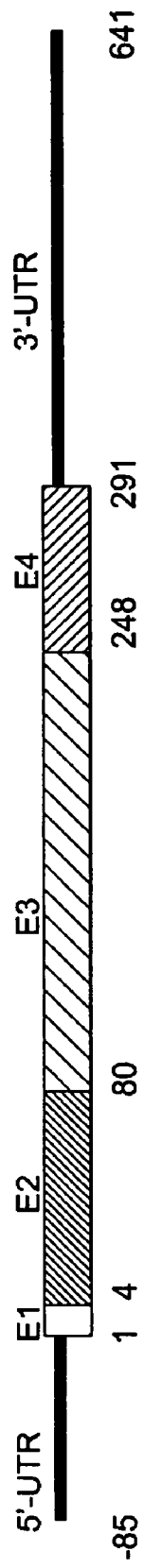
FIG. 12 is a schematic representation of the km23 wild-type gene showing the positions of the coding region and 5' and 3' untranslated regions. The present figure further shows primer pairs useful for RT-PCR amplification of the entire coding region of the km23 gene, the primers being useful in diagnostic/prognostic screening methods of the present invention.
Figure 13:
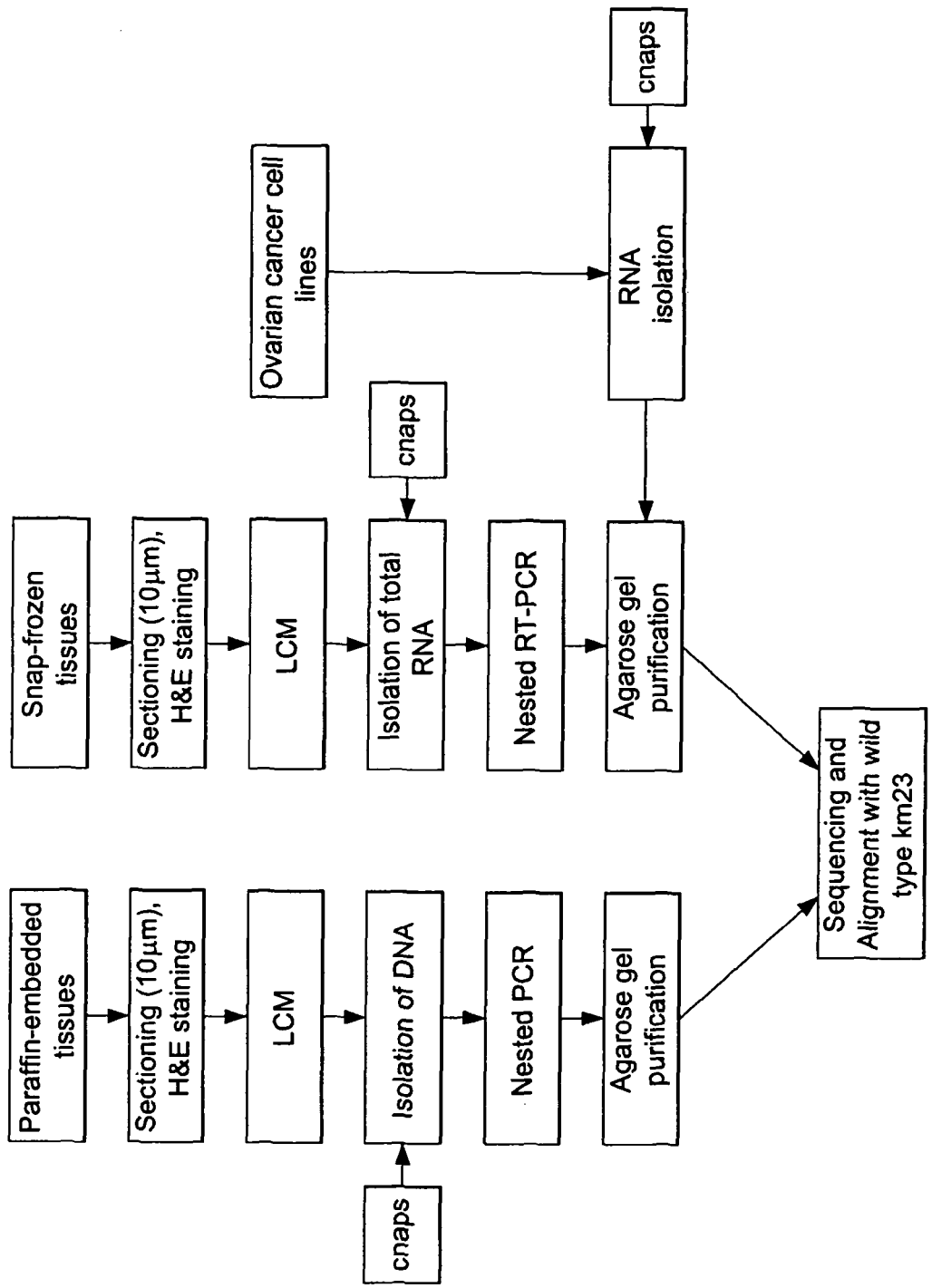
FIG. 13 is a flow chart which indicates the different approaches used to identify the types and frequency of km23 alterations in ovarian cancer, as well as the different sources of materials for diagnostic and prognostic assays.

With reference now to Example 14, and with further reference to FIGS. 11-13, the present invention provides preferred methods for diagnostic/prognostic screening of patient samples to detect the presence or absence of a specific alteration in sequence (relative to wild-type) of a km23 nucleic acid or polypeptide form. These screening methods will now be described in detail.

One preferred screening method of this invention is a nested RT-PCR method, the method including: (a) providing a km23 RNA form from a patient specimen; (b) providing a first pair of PCR primers which span the entire open reading frame of km23; (c) performing a first round of nested RT-PCR using (i) the km23 RNA form as the reaction template and (ii) the first primer pair under suitable conditions to obtain a first PCR product; (d) providing a second pair of PCR primers capable of binding within the first PCR product; (e) performing a second round of nested RT-PCR using the first PCR product as the reaction template under suitable conditions to obtain a second PCR product; and (f) sequencing and aligning the second PCR product with a wild-type km23 nucleic acid form to determine a specific alteration in sequence.

In one embodiment of the nested RT-PCR screening method, the method further includes correlating the specific alteration in sequence with a specific disorder or a risk for a disorder selected from the following: ovarian cancer, breast cancer and colon cancer.

In one embodiment of the RT-PCR screening method, the first primer pair for first round PCR corresponds to SEQ ID NO: 20 (forward primer) and SEQ ID NO: 21 (reverse primer). In a further desired embodiment, the second primer pair for second round PCR corresponds to SEQ ID NO: 22 (forward primer) and SEQ ID NO: 23 (reverse primer).

The km23 RNA form from the patient specimen is preferably isolated from snap-frozen tissue after laser capture microdissection, or is isolated from circulating nucleic acids in plasma/serum (cnaps) according to methods described below. Moreover, RNA may be isolated from cancer cells from the patient. In the case of breast cancer, the cells or nucleic acids may also be obtained from needle biopsies or nipple aspirates, in the case of colon cancer, from stool samples or fecal matter, and in the case of ovarian cancer, from peritoneal fluids such as ascites. Following RT-PCR, the relevant PCR products are purified by agarose gel electrophoresis and sequenced to identify the presence of any alterations.

Other preferred diagnostic/prognostic methods provided by this invention are nested PCR method which involves PCR amplification of individual exons. For example, the method includes: (a) providing a km23 genomic nucleic acid form from a patient specimen; (b) providing a first pair of PCR primers which span exon 2, 3, or 4 of the km 23 genomic nucleic acid form; and (c) performing a first round of nested PCR amplification of a region of the km23 genomic nucleic acid form comprising exon 2, 3 or 4 using the first pair of primers under suitable conditions to obtain a first PCR product; (d) providing a second pair of PCR primers capable of binding within the first PCR product; (e) performing a second round of nested PCR amplification using the first PCR product as the reaction template under suitable conditions to obtain a second PCR product; and (f) sequencing and aligning the second PCR product with a wild-type km23 nucleic acid form to determine a specific alteration in sequence.

In one embodiment of the nested PCR method for amplification of a region including exon 2, the first pair of primers correspond to SEQ ID NO: 12 and SEQ ID NO: 13 and the first PCR product is about 302 bps. In another embodiment of this method, the second pair of exon 2 PCR primers correspond to SEQ ID NO: 14 and SEQ ID NO: 15 and the second PCR product is about 225 bps.

Desirably, the nested PCR method for amplification of a region including exon 3 employs a first pair of primers corresponding to SEQ ID NO: 8 and SEQ ID NO: 9 to yield a first PCR product of about 356 base pairs. In another desired embodiment of this method, the second pair of exon 3 primers correspond to SEQ ID NO: 10 and SEQ ID NO: 11; and the second PCR product is about 254 base pairs.

Furthermore, the nested PCR method for amplifying a region including exon 4 preferably employs a first pair of primers corresponding to SEQ ID NO: 16 and SEQ ID NO: 17 to produce a first PCR product of about 286 base pairs. In a further embodiment of this method, the second pair of exon 4 primers corresponds to SEQ ID NO: 18 and SEQ ID NO: 19 and the second PCR product is about 197 base pairs.

In particular embodiments of the nested PCR methods provided by this invention, the method would further include correlating the identified specific alteration in sequence with a disorder selected from the following: ovarian cancer, breast cancer and colon cancer.

In another embodiment, the nested PCR methods provided by this invention could include modifications to the PCR approach such as in performing digital PCR (Vogelstein & Kinzler, 1999; PNAS 96; 9236-9241).

With reference to FIG. 13, it can be seen that template DNA for the nested PCR screening methods of this invention is preferably isolated from tissues which have been laser capture microdissected or from cnaps. In the case of breast cancer, the cells or nucleic acids may also be obtained from needle biopsies or nipple aspirates, in the case of colon cancer, from stool samples or fecal matter, and in the case of ovarian cancer, from peritoneal fluids such as ascites. Following nested PCR amplification, relevant PCR products are purified by agarose gel electrophoresis, sequenced and aligned with wild-type km23 to determine alterations.

In a further embodiment of the invention, the alterations in km23 may be detected in conjunction with other genetic alterations of the disorder.

This invention further provides a method for screening for the presence or absence of a lesion in a patient specimen which is characterized by an alteration in a km23 nucleic acid or polypeptide form. The method includes: (i) providing a km23 nucleic acid form from a patient specimen; (ii) detecting the presence of an alteration in a km23 nucleic acid form relative to the wild-type km23 nucleic acid form, which alteration results in one of the following: (a) a mutant km23 polypeptide having a Gly at the amino acid corresponding to amino acid number 55 of SEQ ID NO: 1 or SEQ ID NO: 2; (b) a mutant km23 polypeptide having a Val at the amino acid corresponding to amino acid number 89 of SEQ ID NO: 1 or SEQ ID NO: 2; (c) a mutant km23 polypeptide having a Ile at the amino acid corresponding to amino acid number 46 of SEQ ID NO: 1 or SEQ ID NO: 2; and (d) a mutant km23 polypeptide having a Ser at the amino acid corresponding to amino acid number 56 of SEQ ID NO: 1 or SEQ ID NO: 2; (e) a mutant km23 polypeptide having an Ala at the amino acid corresponding to amino acid number 4 of SEQ ID NO: 1 or SEQ ID NO:2; (f) a mutant km23 polypeptide having an Ala, Asp, or Glu at the amino acid corresponding to amino acid number 32 of SEQ ID NO: 1 or SEQ ID NO: 2; (g) a mutant km23 polypeptide having a Glu or Asp at the amino acid corresponding to amino acid number 55 of SEQ ID NO: 1 or SEQ ID NO: 2; (h) a mutant km23 polypeptide having a Ala, Glu, or Asp at the amino acid corresponding to amino acid number 73 of SEQ ID NO: 1 or SEQ ID NO: 2; (i) a mutant km23 polypeptide having a Ala, Asp, or Glu at the amino acid corresponding to amino acid number 7 of SEQ ID NO: 1 or SEQ ID NO: 2; (j) a mutant km23 polypeptide having a Ala, Asp, or Glu at the amino acid corresponding to amino acid number 33 of SEQ ID NO: 1 or SEQ ID NO: 2; (k) a mutant km23 polypeptide having a Ala, Asp, or Glu at the amino acid corresponding to amino acid number 56 of SEQ ID NO: 1 or SEQ ID NO: 2; (l) a mutant km23 polypeptide having an Ala or Glu at the amino acid corresponding to amino acid number 13 of SEQ ID NO:1 or SEQ ID NO:2; (m) a km23 polypeptide having SEQ ID NO:1 or SEQ ID NO:2, except that the polypeptide lacks amino acids corresponding to amino acids 27-82 in SEQ ID NO:1 or SEQ ID NO:2; and (n) a km23 polypeptide having the amino acid sequence corresponding to SEQ ID NO:6.

In one embodiment of the method just described, the identified alteration is correlated specifically with a disorder or a risk therefore, wherein the disorder is selected from, but not limited to, the following: ovarian cancer, breast cancer, and color cancer. In another embodiment, the identified alteration is used to predict patient characteristics, including but not limited to, disease recurrence and response to chemotherapeutic agents.

The invention also provides a method for detecting the presence or absence of a lesion in a patient specimen characterized by an alteration in post-translational modification of a km23 nucleic acid or polypeptide form. In one embodiment of this method, the presence or absence of a lesion is characterized by an altered transduction activity of a km23 polypeptide. This method is useful for both diagnostic, as well as prognostic screening.

Functional assays can be used in the diagnosis of a particular disorder. For example, it is known that km23 protein is a protein capable of associating with the TGFβ receptor complex. Thus, an assay to assess the ability of a particular km23 protein form to associate with the receptor can be employed in the determination of whether a patient has a particular disorder.

In a further embodiment of the invention, polynucleotides encoding the km23 polypeptides, km23 fragments and km23 mutants of this invention may be used for diagnostic purposes. These polynucleotides may include oligonucleotide sequence such as anti-sense, RNA and DNA molecules. For example, polynucleotides may be used to detect and quantitate gene expression in biopsied tissues in which expression of km23 may be correlated with a specific disease. The diagnostic assay can be used for example to distinguish between the absence, presence, or an excess expression of km23, as well as to monitor the regulation of km23 levels during therapeutic intervention. It is also contemplated within the scope of the invention that the nucleic acid probe assays will employ a cocktail of nucleic acid probes capable of detecting km23 genes.

A wide variety of labels and conjugation techniques are known by those skilled in the art and may be used, for example, in the various nucleic acid hybridization assays and amino assays. Methods for producing labeled hybridization or PCR probes for detecting sequences related to polynucleotides encoding km23 include oligo-labeling, mixed translation, and labeling or PCR amplification using a labeled nucleotide. Suitable labeled reporter molecules which may be used include radionuclides, enzymes, fluorescents, chemiluminescent, or chromogenic agents as well as substrates, cofactors, inhibitors, magnetic particles, and the like.

Furthermore, DNA sequences of the km23 gene which have been amplified by use of PCR may be screened using mutation-specific probes. For example, these probes are nucleic acid oligomers, each of which contains a region of a km23 gene sequence harboring a known mutation. By use of a battery of such mutation-specific probes, PCR amplification products can be screened to identify the presence of a previously identified mutation in the km23 gene. Such hybridization of mutation-specific probes with amplified km23 nucleic acid sequences can be performed, for example, on a nylon filter. Hybridization to a particular probe under stringent hybridization conditions would indicate the presence of the same mutation in the tumor tissue as in the mutation-specific probe. The ability of the probe to identify naturally occurring sequences encoding km23 mutations, will depend on the stringency of the hybridization or amplification.

Alteration of km23 mRNA expressions can be detected by any techniques known in the art. These include Northern blot analysis, PCR (e.g., RT-PCR amplification), as well as RNase protection. Diminished mRNA expression indicates an alteration of the wild-type km23 gene.

Alteration of the wild-type km23 gene can also be detected by immunoscreening for alteration of wild-type km23 protein. For example, monoclonal antibodies provided by this invention which are specific for an antigenic determinant in a mutant km23 protein can be used to screen a tissue. Presence of antigen in the tissue would indicate a km23 mutation. Such immunological assays can be done in any convenient format known in the art. These include Western blot, immunoblots, chemical assays and ELISA.

The antibodies used for diagnostic purposes may be prepared in the same manner as those described above for therapeutics. Diagnostic assays for km23 protein include those methods which utilize a labeled antibody to detect km23 protein in human body fluids or extracts of cells or tissues. The antibodies may be used with or without modification, and may be labeled by joining them with a reporter molecule. Such reporter molecules are known in the art.

Methods for Identifying Therapeutic Agents

The present invention provides a method for identifying therapeutic agents that inhibit, potentiate, or mimic the ability of a km23 polypeptide or a nucleic acid encoding the polypeptide to modulate the signal transduction activity of a TGFβ growth factor, the method including: treating a cell with an effective amount of at least one candidate so as to alter at least one of the following: regulation of gene expression, cell growth, cell differentiation, cell survival, apoptosis, senescence, cell migration, antiogenesis, fibrosis, wound healing, extra cellular matrix induction, adhesion, auto production, embryogenesis and combinations thereof; and (b) measuring the effect of the candidate on the cell. Preferably, candidates which are therapeutic agents that modulate or mediate at least one of the cellular functions described above do so by an amount at least 10% relative to the cell in the absence of the candidates.

For example, in one embodiment, the method includes measuring the effect of a candidate on the proliferation of the cell, wherein candidates that inhibit the proliferation of the cell by an amount at least 10% that of a functional km23 polypeptide are therapeutic agents. In another embodiment, the therapeutic agent inhibits the proliferation of the cell by an amount at least about 25% of the functional km23 polypeptide. In yet another embodiment, the therapeutic agent inhibits the proliferation of the cell by an amount at least about 50% that of the functional km23 polypeptide. In a further embodiment, the therapeutic agent inhibits the proliferation of the cell by an amount at least about 75% that of the functional km23 polypeptide. Most desirably, the therapeutic agent would inhibit the proliferation of the cell by an amount at least about 90% that of the functional km23 polypeptide. It is noted that the proliferation may be inhibited either ex vivo or in vivo. In this method, therapeutic candidates are compared in performance with a standard, wherein the standard is a functional km23 polypeptide.

The present invention provides a cell-based assay for screening therapeutic agents that stimulate or inhibit the interaction of a km23 polypeptide form with a specific binding protein, the method including: (a) providing drug-inducible km23 expressing cells (e.g. tet-inducible km23 expressing cells), wherein the expressed km23 is a wild-type form or an altered form thereof; (b) treating the cells of (a) with an effective amount of a therapeutic candidate so as to alter the growth inhibitory effect of km23; and (c) measuring the effect of the candidate on the cells with a cell growth assay.

In one embodiment of the cell-based assay, the specific binding protein is the dynein intermediate chain. In another embodiment, the specific binding protein is a receptor for a growth factor. This method is described in detail in Example 17 below.

The present inventor has determined that km23 functions as a tumor suppressor, blocking cell growth under normal conditions. In contrast, alterations in the km23 gene in epithelial cancers abrogate the tumor suppressive function of km23. The cell-based assay of this invention is useful for screening to identify agents that restore the normal functions of km23, or replace the altered forms/functions of km23.

In this regard, the invention provides a method of restoring the growth inhibitory activity of at least one TGFβ superfamily member, the method including introducing into the cell an antagonist of a mutant km23 polypeptide form. In one embodiment of this method, the antagonist is a therapeutic agent identified by the cell-based therapeutic screening assay provided herein.

Other useful therapeutic agents which can be identified by the cell-based assay of this invention include those that block TGFβ production by interfering with wild-type km23's actions in this regard (see Example 15 and 15.1). For example, blocking TGFβ production would be desirable in situations where tumors are no longer inhibited by TGFβ, and TGFβ leads to tumor spread. In this situation, a mimetic of the R58V mutant is a useful therapeutic agent. In this regard, the present invention provides a method of regulating TGFβ production, the method including introducing into the cell a mimetic or antagonist of a mutant km23 polypeptide form. In one embodiment, the mimetic or antagonist is a therapeutic agent.

This invention also provides a method of screening for a therapeutic agent that modulates the interaction of a km23 polypeptide form with the dynein intermediate chain, the method including: (a) providing a fusion protein which includes a dynein intermediate chain polypeptide labeled with a first fluorophore; (b) providing a fusion protein which includes a km23 polypeptide form labeled with a second fluorophore; (c) incubating components (a) and (b) in the presence and absence of an effective amount of a therapeutic candidate under suitable conditions to allow protein interaction between components (a) and (b); and (d) detecting the effect of the candidate on the interaction by comparing the fluorescence spectra for each of the fluorescently labeled polypeptides in the presence and absence of the candidate.

In one embodiment of this method, the dynein intermediate chain (DIC) polypeptide is wild-type, or a fragment or mutant form thereof. In another embodiment, the km23 polypeptide is wild-type, or a fragment or mutant form thereof. As described below in Example 11, the present inventor has determined that a spliced variant of km23 from *Drosophila* binds weakly to DIC as compared to the wild-type protein. A similar spliced variant has been found by the present inventor in both ovarian cancer tissue samples and in ovarian cancer cell lines, providing evidence that alterations in the normal interaction between km23 and DIC may lead to cancer. Therefore, a useful therapeutic agent is one which would be capable of altering the interaction of km23 forms with the DIC. A preferred method used to identify such an agent is the FRET assay described in Example 18.

Figure 15:
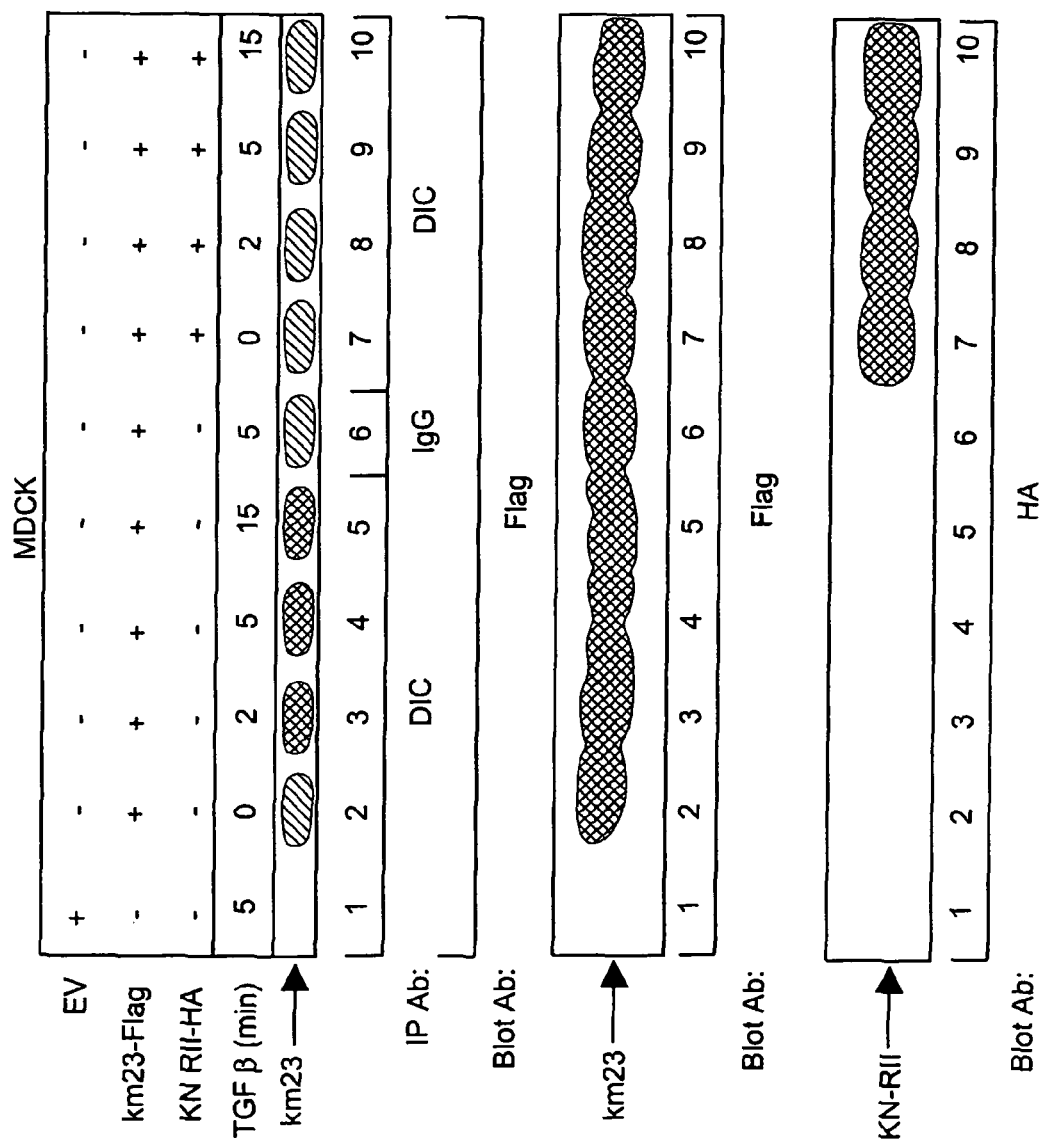
FIG. 15. The kinase activity of TGFβ RII is required for the km23-DIC interaction. In this experiment, MDCK cells were transiently transfected with empty vector, km23-flag or km23-flag and KN RII-HA (a kinase-deficient receptor). Cells were treated for various times with TGFβ. Cell lysates were subjected to immunoprecipitation using a monoclonal anti-DIC antibody, followed by immunoblot analysis using anti-flag (top panel). Bottom panels-western blotting controls demonstrating expression of km23 (flag) and KN-RII (HA).

The inventor has provided evidence that km23 interacts with the DIC (see FIG. 6 and Example 10) and that the phosphorylation of km23 appears to be necessary for this interaction to occur (see FIG. 15 and Example 12). In view of this, the present invention also provides a method for identifying therapeutic agents that inhibit, potentiate, or mimic the ability of a km23 polypeptide, mutant form thereof, or a nucleic acid encoding the polypeptide, or mutant form thereof, to modulate the signal transduction activity of a growth factor or cytokine, the method including: (a) treating a cell with an effective amount of at least one candidate so as to alter at least one of the following: actin cytoskeleton dynamics, microtubule dynamics, intracellular transport, cell polarity, dynein-mediated microtubule transport and combinations thereof; and (b) measuring the effect of the candidate on the cell. It is noted that actin cytoskeleton dynamics, microtubule dynamics, intracellular transport, and cell polarity are, at least in part, dynein motor protein related events.

In one aspect of the invention, km23, its fragments, or mutant fragments or forms, or oligopeptides thereof, can be used for screening libraries of compounds using any of drug screening techniques of the present invention. The fragment employed in such a screening may be free in solution, affixed to a solid support, borne on a cell surface, or located intracellularly. The formation of binding complexes between km23 and the agent being tested, may be measured. Formation of a complex between km23 and an agonist agent would have the effect of potentiating the ability of km23 to act as a signaling intermediate in the TGFβ signaling pathway. Alternatively, the formation of a binding complex between km23 and an antagonist of its function can inhibit its ability to act as a signaling intermediate in the TGFβ pathway and can provide an overall means of modulating km23 activity. This latter effect may be useful for application to cells other than the tumor epithelial cells in an in vivo setting, since it is well established that the paracrine effects of TGFβ (on stromal cells such as immune cells, fibroblasts, endothelial cells, etc., surrounding the tumor epithelial cells) enhance tumor spread. In these cells, km23 would be expected to result in cellular responses similar to those TGFβ induces, and these are essentially all tumor enhancing.

EXAMPLE 1

Preparation of a cDNA Expression Library from TGFβ-Stimulated IEC 4-1 Cells

The rat IEC line IEC 4-1 (Mulder et al., 1993) was used as a source of RNA for synthesis of the cDNA library to be screened for proteins which interact with the bacterially expressed, phosphorylated TβR intracellular domains. Cells were cultured as previously described and tested for growth inhibition following treatment with TGFβ$_3$ (10 ng/ml) by a $^3$H-thymidine incorporation assay to measure DNA synthesis (Hartsough et al., 1996). To harvest total cellular RNA, IEC 4-1 cells were plated at a density of 6660 cells/cm$_2$ and were switched to serum-free medium the following day. After 24 h, TGFβ$_3$ was added to the cell cultures at a concentration of 10 ng/ml and cells were incubated for an additional 3 minutes prior to RNA harvest by a standard protocol (Chirgwin et al., 1979). Messenger RNA was purified via passaging of total cellular RNA over an oligo(dT) cellulose column (Gibco BRL). cDNA synthesis was carried out using the Superscript Choice System for cDNA Synthesis (Gibco BRL). First-strand synthesis was performed using both random oligo- and oligo-dT primers provided by the manufacturer. Double-stranded cDNA ligated to Eco RI adapters was size-selected and fractions were analyzed by agarose gel electrophoresis. Fractions 6 through 8 were pooled and ligated into the Eco RI site of the TriplEx expression vector (Clontech). The ligated DNA was incorporated into phage particles (Gigapack II Gold, Stratagene, La Jolla, Calif.) and titered by infection of E. coli strain XL 1-Blue. The phage/bacteria mixture was plated onto NZY/agar plates containing IPTG and X-gal following the manufacturer's protocols (Clontech) to determine the titer and percentage of recombinant phage generated.

EXAMPLE 2

Screening of the cDNA Expression Library for Proteins which Interact with Phosphorylated TGFβ Receptors Recombinant phage were screened using a modified CORT protocol (Skolnik et al., 1991). The packaged cDNA library was plated at a density of 20,000 plaques/150 mm petri dish. Following incubation of the petri dishes at 42° C. for 4 to 5 h to allow for phage growth, plates were overlaid with nitrocellulose filters (Millipore) which had been soaked in 10 mM IPTG for 20 minutes, and the plates were incubated at 37° C. for an additional 3 h. Filters were removed and rinsed 3 times in TBST, incubated at room temperature for 1 h in 5% milk/TBST, rinsed an additional 3 times in TBS, and finally incubated overnight at room temp with freshly harvested TβR protein, which had been phosphorylated in an in vitro kinase assay and resuspended in PBS. Typically, the proteins were labeled at a concentration of 15-17 Ci/mmol, which represented between 5 and 10 μg of protein, and were eluted and used for screening 10 filters. Following incubation, filters were washed 3 times at room temperature for 5 min each in TBS. The occurrence of interactions between recombinant $^{32}$P-labeled TβR proteins, and expressed proteins from the cDNA library, were determined by autoradiography. Positive plaques were picked and resuspended in phage buffer SM at 4° C. for several hours to elute phage particles. Eluted phage were titered and replated for secondary screening to enrich for positive clones. A third round of screening confirmed the presence of a pure culture of a single clone.

To obtain a plasmid containing the positive clone, a single, isolated positive phage plaque was picked from the tertiary screen plate, placed in one ml of SM buffer, and incubated at 4° C. for several hours to allow the phage particles to elute. Bacterial strain BM25.8 (Clontech) was grown and infected with the eluted phage particles following the manufacturer's protocol. Briefly, the bacteria were cultured overnight at 31° C. in NZY media containing 20 mM maltose and the following day, the culture was supplemented with 1 M M$_g$Cl$_2$ to a final concentration of 10 mM. Two hundred μl of BM25.8 culture was added to 150 μl of eluted phage and the solution was placed at 31° C. for 30 minutes without shaking to allow for infection to take place. Four hundred μl of LB broth was added and the mixture was allowed to grow at 31° C. for 1 h with shaking to induce the DNA recombination necessary to generate a plasmid containing the inserted clone. Aliquots of the culture were plated onto LB/agar plates containing carbenicillin. After incubation overnight, a single colony was picked and cultured to obtain plasmid DNA for sequencing and further analysis.

EXAMPLE 3

Identification of a km23 Protein and Isolation of the Full-Length cDNA

The positive clone was sequenced and the generated sequence (approx. 463 bp) was compared by BLAST analysis to sequences published in available databases (Genbank, EST, etc). The DNA insert from the positive clone was removed with Eco RI or Not I digestion and used to screen the phage library to obtain a full-length cDNA copy of the gene. Briefly, phage were plated at a density of 50,000/150 mm plate and incubated overnight. Plaques were lifted onto nitrocellulose filters according to standard protocols and the presence of positive clones was identified using the DNA insert described above which had been labeled with $^{32}$p-dCTP using a random priming kit (Gibco BRL). The resulting clones were picked and rescreened twice to ensure a pure phage clone had been obtained. Plasmid DNA was harvested and sequenced to determine if the entire gene had been isolated.

EXAMPLE 4

Cell Culture 293T cells were obtained from T. Wong (Bristol-Myers Squibb) and were maintained in Dulbecco's Modified Eagle Medium (GibcoBRL, Cat. No. 11995-065) supplemented with 10% fetal bovine serum (FBS). Madin Darby canine kidney (MDCK) cells were obtained from American Type Culture Collection (ATCC, Cat. No. CCL-34) and were maintained in Minimum Essential Medium-α Medium (Gibco-BRL, Cat. No. 12561-056) supplemented with 10% FBS. Cells were routinely subcultured prior to 90-95% confluency using 0.26% trypsin in S-MEM Joklik Modified medium (GibcoBRL, Cat. No. 22300-024) containing 0.1% EDTA. Mink lung epithelial cells (Mv1Lu/CCL64) were obtained from ATCC and cultured as described previously (Mulder and Morris, 1992; Hartsough and Mulder, 1995).

EXAMPLE 5

Transient Transfections 293T cells were transiently transfected with TGFβ receptors using Lipofectamine Plus (GibcoBRL, Cat. No. 10964-013) according to the manufacturer's instructions. Briefly, cells were plated in 60 mm plates so that the confluency was approx. 50% by 24 h later. 3 μg total DNA was added to 0.3 ml PBS and 6 ml Plus reagent, followed by addition of 10 ml Lipofectamine and incubation for another 20 min at room temperature. After washing plates with Opti-MEM I (Gibco-BRL, Cat. No. 31985-070), the DNA/Plus/Lipofectamine solution was applied to the plates for a 4-6 h incubation at 37° C. in 5% $CO_2$. MEM I/20% FBS was then added for 24 h.

MDCK (or Mv1Lu) cells were transiently transfected using Superfect (Qiagen Cat. No. 301305) according to the manufacturer's protocol. Briefly, cells were plated in 60 mm dishes as described for 293T cells. DNA (10 μg) was added to MEM-α without serum, followed by addition of Superfect. MEM-α 10% FBS (1 ml) was added to the DNA/Superfect solution and then applied to the plates for a 4-6 h incubation at 37° C. in 5% $CO_2$. Plates were then incubated in MEM-α 10% FBS for approx. 36 h.

EXAMPLE 6

$^{125}$I-TGFβ Crosslinking Studies

This example describes the crosslinking studies verifying that km23 interacts with the TGFβ receptors. Additional studies performed by the inventor demonstrate that there is a direct interaction between km23 and TGFβ receptors, and that TGFβ increased the interaction between km23 and the TGFβ receptors, as determined by immunoprecipitation/blot experiments (not shown).

$^{125}$I-TGFβ crosslinking studies were performed essentially as described (Mulder et al, 1993; Zhou et al, 1995a; 1995b; Yue et al, 1999a). Briefly, 293T cells were plated at a density of 4×10$^5$ cells/cm$^2$ in T-75 flasks in DMEM medium. The next day, cells were transfected with km23-flag and tagged-TβR's as described for the in vivo phosphorylation assays. Cells were then washed twice with PBS and incubated in serum-free medium for 1 h, followed by incubation in blocking buffer (DMEM, 25 mM Hepes, pH 7.4, 2 mg/ml BSA) for 30 min at 37° C. Cells were then incubated with binding buffer (DMEM, 25 mM Hepes, pH 7.4, 5 mg/ml BSA) containing 200 pM $^{125}$I-TGFβ$_1$ in presence or absence of cold TGFβ (1 nM) for 4 h at 4° C. The labeling medium was removed, and cells were incubated with wash buffer containing 0.3 mM disuccinimidyl suberrate (DSS) for 15 min at 4° C. Cells were washed with termination buffer three times and were lysed with lysis buffer. Cell lysates (200 μl) were immunoprecipitated using either an anti-Flag antibody or mouse IgG. Immunocomplexes were resolved by SDS-PAGE (10%), and gels were dried and exposed to X-ray film at 70° C. Total cell lysates were subjected to immunoblot analysis for confirmation of expression of km23 and receptors.

Figure 2B:
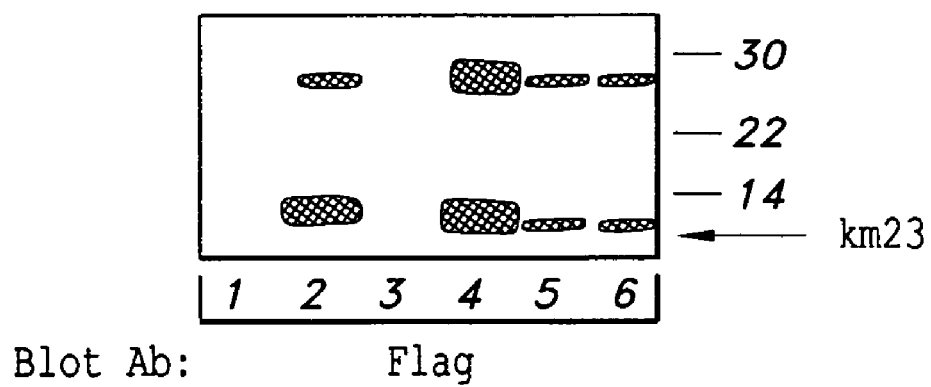
Figure 2C:
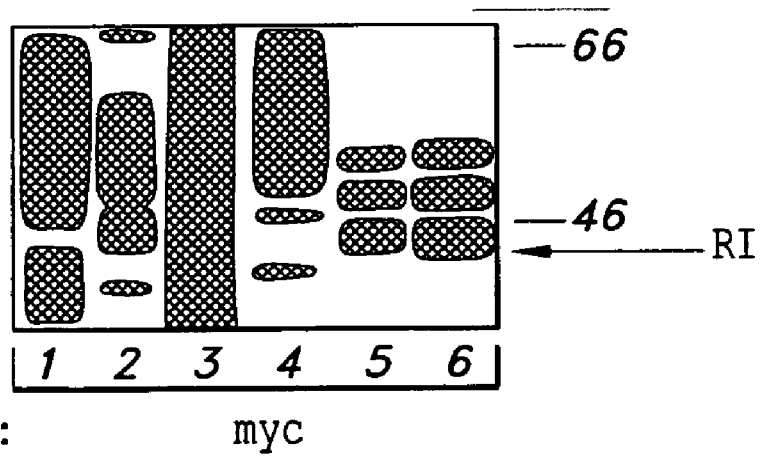
Figure 2D:
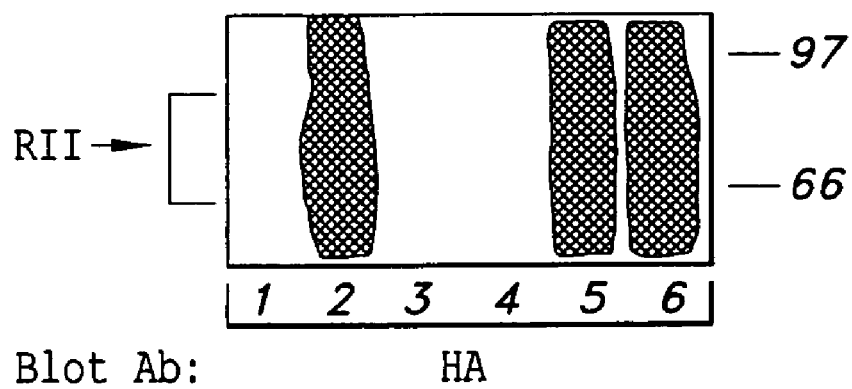
Figure 3A:
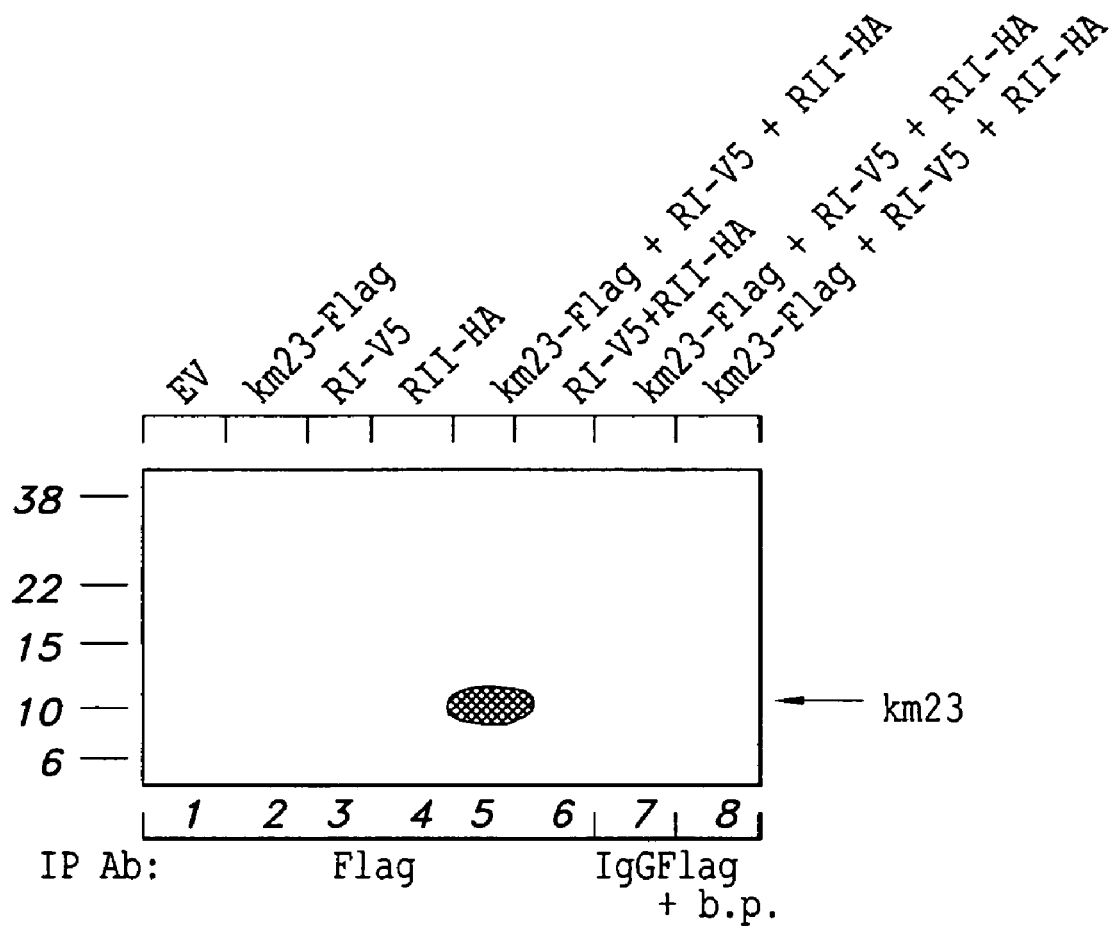
FIG. 3. km23 is phosphorylated by the RI/RII TGFβ receptor complex. 293T cells were transiently transfected with RI-V5, RII-HA, and either empty vector (EV) or km23-flag. 48 h after transfection, cells were labeled for 3 h with [$^{32}$P$_i$], lysed, and IP'd with an anti-flag Ab. A: In vivo phosphorylation of km23 was visualized by SDS-PAGE and autoradiography. B: Flag immunoblot of A confirms expression of km23-flag in the relevant lanes (2,5). C: V5 immunoblot of A confirms expression of RI-V5 in the relevant lane (5). D: HA immunoblot of A confirms expression of RII-HA in the relevant lane (5).
Figure 3B:
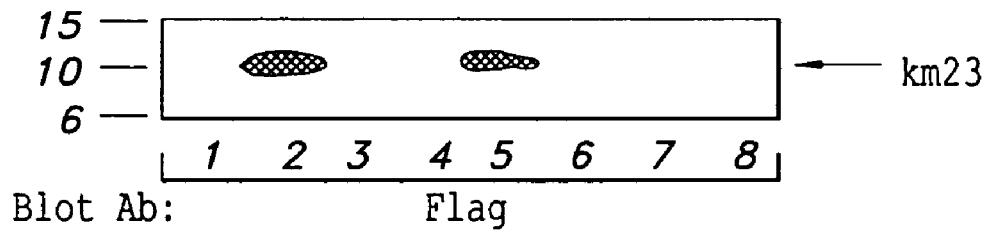
Figure 3C:
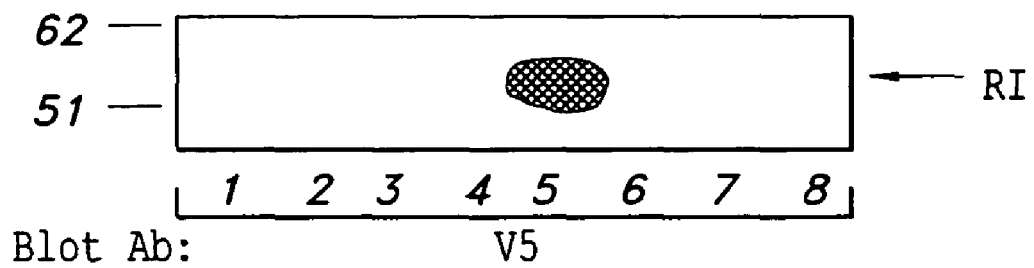
Figure 3D:
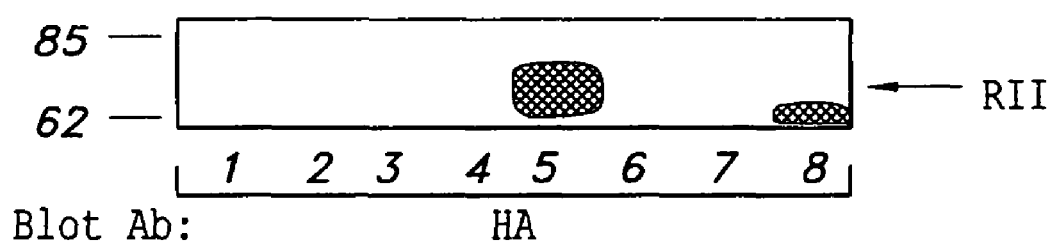

FIG. 2A depicts the results of affinity crosslinking experiments, which indicate that both RI and RII are present in km23-flag immunocomplexes (lane 5) from cell lysates of 293T cells which had been transiently transfected with TGFβ receptors and/or km23 flag, prior to $^{125}$I-TGFβ affinity labeling. As expected, cold TGFβ and IgG controls demonstrated no TGFβ receptors (lanes 6, 7). Immunoblotting controls demonstrating expression of the transfected km23-flag (B), RI-myc (C) and RII-HA (D) are also shown. FIG. 2B confirms that km23 was present in all lanes corresponding to samples from cells in which it had been expressed. FIGS. 2C and 2D demonstrate that RI-myc or RII-HA was present in the expected lanes (2, 5, and 6). Thus, the transfection, expression, and loading aspects of the assays were appropriately performed. The results clearly indicate that the TβR complex can phosphorylate km23.

EXAMPLE 7

In Vivo Phosphorylation Assays

This example demonstrates that km23 is phosphorylated by the RI/RII TGFβ receptor complex.

In vivo phosphorylation assays were performed essentially as described previously (Liu et al, 1998; Yue et al, 1999a; b). Briefly, 293T cells were plated in 60 mm dishes at 0.7×10$^6$ cells/cm$^2$ and were transfected using Lipofectamine Plus (Gibco-BRL) during experimental phase growth. After the 4-h transfection period, Opti-MEM supplemented with 10% FBS was added for 24 h followed by normal growth medium for an additional 24 h. Cells were then incubated in serum-free, phosphate-free DMEM for 30 min, labeled for 3 h with [$^{32}$p]-orthophosphate (mCi/ml) at 37° C. in 5% $CO_2$, washed with cold PBS, and lysed in 120 μl of lysis buffer (1% Triton X-100, 10 Mm Tris [pH 7.6], 50 mM NaCl, 30 mM Na pyrophosphate, 50 Mm NaF, 1 mM PMSF, 1 mM Na orthovanadate, 1 μg/ml aprotinin, 5 mM benzamidine, 1 mM EGTA, pH 8.0, 100 nM okadaic acid) at 4° C. for approx 5 min. Insoluble debris was removed by micro-centrifugation at 10,000 rpm for 20 min. The supernatants were then normalized for radioactivity as determined by TCA precipitation. Equal radioactivity of cleared cell lysates were immunoprecipitated for 2 h at 4° C. with 10 μg of Anti-Flag M2 monoclonal antibody (Sigma) or Mouse IgG (Sigma), followed by absorption to protein A-agarose (Gibco-BRL). Beads were washed 3 times in lysis buffer without aprotinin and okadaic acid. Bound proteins were eluted by heating in electrophoresis sample buffer containing DTT, and analyzed by SDS-PAGE (6-20% gradient). The wet gel was exposed to X-OMAT AR film (Kodak) at −80° C. Proteins on the gel were transferred to an Immobilon-P PVDF membrane (Millipore) and immunoblotted with anti-Flag antibody to detect expression of tagged proteins.

As shown in FIG. 3, the TβR complex can phosphorylate km23, whereas no phosphorylation is observed in empty vector or IgG controls (lanes 1, 5). FIG. 3B is the blotting control to demonstrate that km23 was expressed in the relevant samples (lanes 2, 4). As a positive control we were also able to show that Smad 3 was phosphorylated by the TβR complex as expected (data not shown). The results demonstrate that the TβR complex can phosphorylate km23.

EXAMPLE 8

Kinetics for TGFβ Induction of km23 Expression in MDCK Cells

MDCK cells were transiently transfected with km23-flag. 36 h after transfection, cells were treated with TGFβ for various time points and then lysed. Total cell lysates were subjected to Western Blot analysis with an anti-Flag Ab.

Referring to FIG. 4, the presence of the km23 band migrating at approximately 11 kD in lanes 2-7 indicates that TGFβ induces expression of km23 in MDCK cells and that this induction is almost immediate.

EXAMPLE 9 km23 Induces CRE Luciferase Reporter Activity and TGFβ Synergizes with km23 in Inducing this Effect Luciferase Reporter Assays were performed essentially as described previously (Liu et al, 1998; Yue et al, 1999a; b). Briefly, cells were transiently transfected as described above and the Dual Luciferase Assay System (Promega) was performed according to the manufacuturer's instructions using renilla luciferase as a control for transfection efficiency.

Figure 5A:
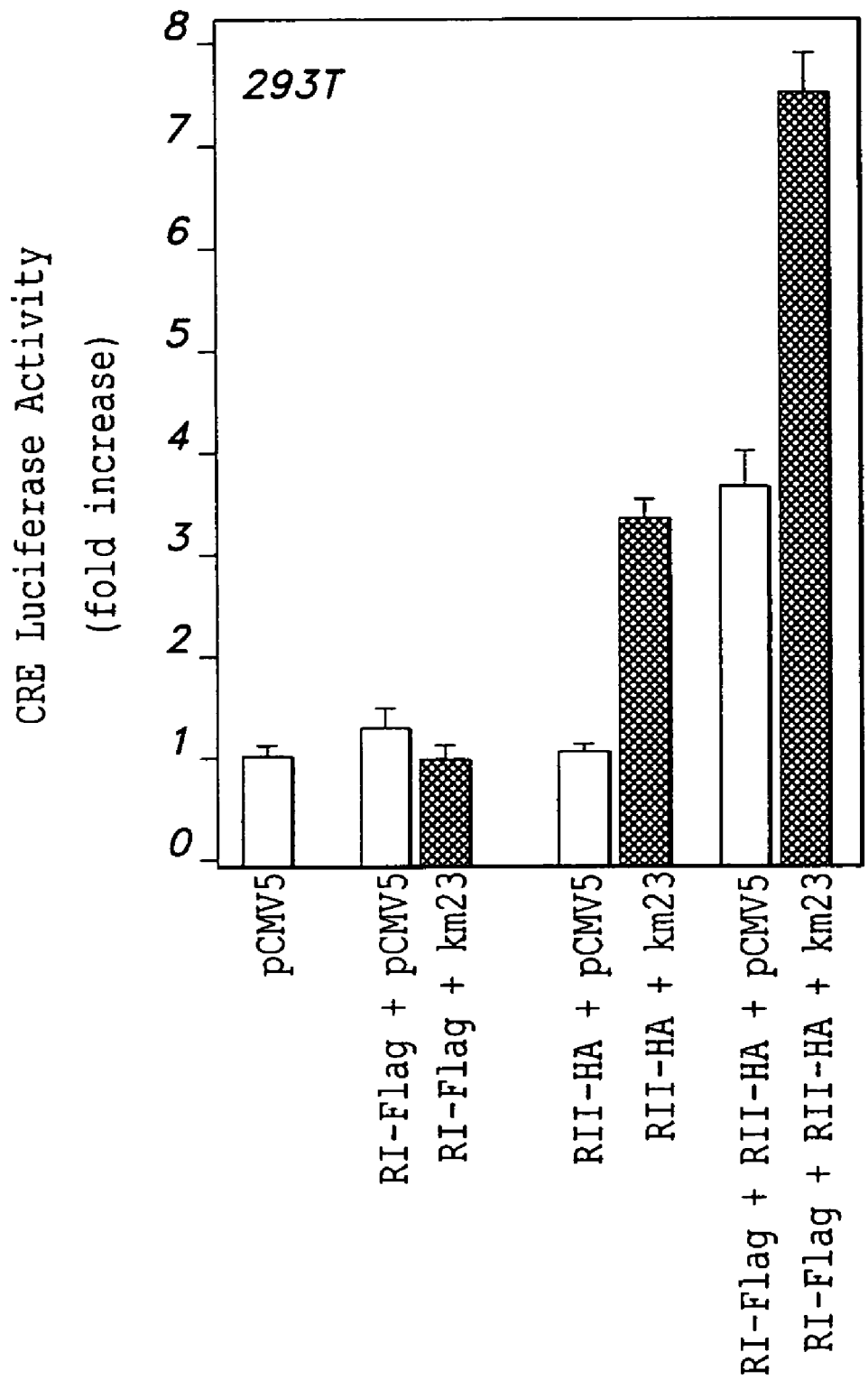
FIG. 5. Induction of CRE-Lux luciferase activity by km23 and TGFβ or its receptors. A: 293T cells were transfected with 0.2 ug CRE, 0.05 ug Renilla, and 0.1 ug of either RI-flag, RII-HA and km23-flag as indicated. 48 h later, cells were lysed and the Luciferase Assay was performed using the Dual Luciferase Assay System (Promega). The results are representative of triplicate experiments. B: Mv1Lu cells were transfected with 0.4 ug cis-CRE, 0.08 ug Renilla, and either 0.04, 0.2, or 0.4 ug of km23 or its empty vector as indicated. 21 h later, cells were changed to serum-free conditions for 1 h, followed by treatment with TGFβ (10 ng/ml) for 24 h. The results are representative of triplicate experiments.

FIG. 5A depicts CRE luciferase reporter activity in 293T cells, in the absence and presence of km23, after transfection with either RI-flag only, RII-HA only, or both TGFβ receptors. As shown, km23 expressed with RII alone was able to stimulate CRE activity by approximately 3-4-fold, whereas expression of RI alone did not. This may be due to the presence of a modest number of endogenous RI receptors in 293T cells. km23 expression with both TGFβ receptors stimulated activity to a greater extent (approximately 7-fold) than did expression of TβR II alone (3-4 fold). Controls for expression of the relevant components transfected were as for the other figures. Since 293T cells express a low level of endogenous RI, and since RII controls expression of RI, it cannot be concluded with certainty that RII alone is sufficient to induce CRE activity. However, it is clear that the TβR complex can synergize with km23 to induce CRE-Lux. The data are consistent with km23 being in a signaling pathway for TGFβ activation of CRE activity. Since activation of CRE sites in the TGFβ$_2$ and TGFβ$_3$ promoters are likely to lead to production of TGFβ$_2$ or TGFβ$_3$, the data also support a role for km23 in TGFβ production.

Figure 5B:
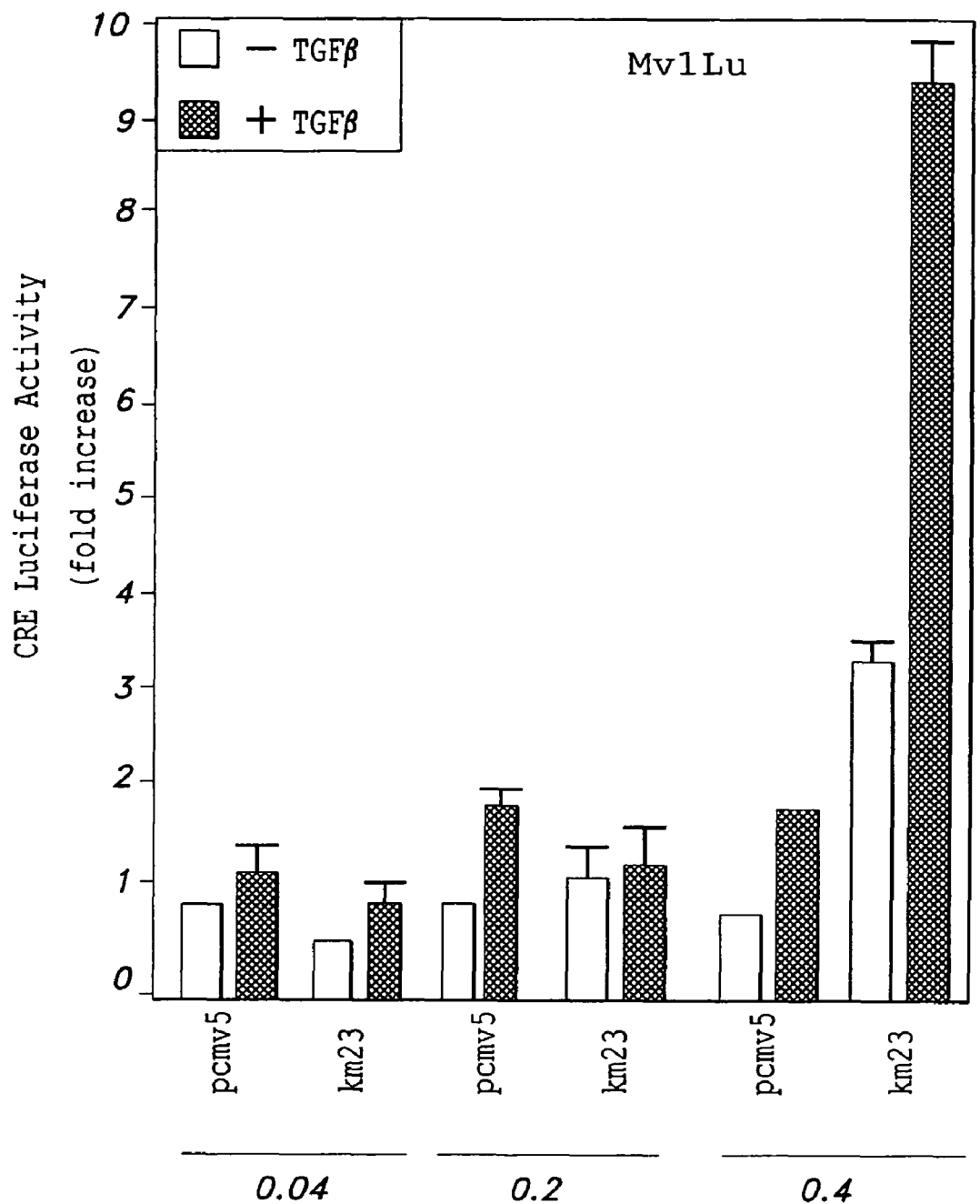

FIG. 5B demonstrates that while TGFβ alone had little effect on CRE reporter activity in mink lung epithelial (Mv1Lu) cells, the combination of km23 and TGFβ synergizes to stimulate CRE activity. Mv1Lu cells express endogenous TGFβ receptors and are highly TGFβ responsive. These results provide additional evidence that km23 is in a TGFβ signaling pathway, and suggest, further, that other events activated by TGFβ and km23 are involved in this transcriptional effect.

EXAMPLE 10 km23 Interacts with the Dynein Intermediate Chain in TGFβ-responsive MDCK Cells

Referring to FIG. 6(A-C), MDCK cells were transiently transfected with either empty vector or km23-flag. 36 h after transfection, cells were treated with TGFβ for various time points and then lysed. Cell lysates were subjected to immunoprecipitation using a monoclonal anti-DIC Ab, followed by immunoblot analysis using an anti-Flag Ab (A). Cell lysates were then blotted with anti-Flag (B) or anti-DIC (C) as a control for expression (B). The presence of the km23 bands in lanes 2-5 (A) indicates that DIC and km23 interact in all samples in which km23 was expressed. Further, the data demonstrate that TGFβ can induce a rapid, time-dependent increase in the interaction between km23 and dynein. This is further evidence that TGFβ can regulate dynein interactions with its associated proteins.

This example illustrates that km23 interacts with DIC biochemically in TGFβ-responsive epithelial cells. For these studies, MDCK cells were chosen to be examined, for which DNA synthesis is inhibited by 60% in thymidine incorporation assays after a 24-h treatment with TGFβ. Moreover, MDCK epithelial cells are often utilized in transport studies due to their highly polarized nature. Thus, these cells will transport proteins along polarized MT's and require dynein for such functions. For the studies shown in FIG. 6, we transfected the MDCK cells with km23-flag and performed immunoprecipitation/blot experiments using an anti-flag Ab to immunoprecipitate km23 and its associated proteins, and a monoclonal anti-DIC Ab to detect cytoplasmic dynein in the km23 immunocomplexes. As shown in FIG. 6A, a 74-kD band corresponding to cytoplasmic DIC was only present in lanes 2-5 where km23 had been expressed in the cells. No specific band was observed when km23 was not expressed (lane 1) or in the IgG lane (lane 6), even when different exposures were examined. The results shown in FIG. 6B and C demonstrate that km23 and dynein were present in the relevant lanes (2-6 for km23, 1-6 for dynein), and were equally expressed. This example demonstrates that km23 interacts with cytoplasmic dynein in TGFβ-responsive epithelial cells. Further, this interaction is enhanced by TGFβ in a rapid, time-dependent manner.

EXAMPLE 11

A Truncated km23 Polypeptide Form Analogous to the *Drosophila* Mutant robl$^z$ Lacking Amino Acids 27-82, Weakly Binds DIC as Compared to Wild-type km23

Figure 14:
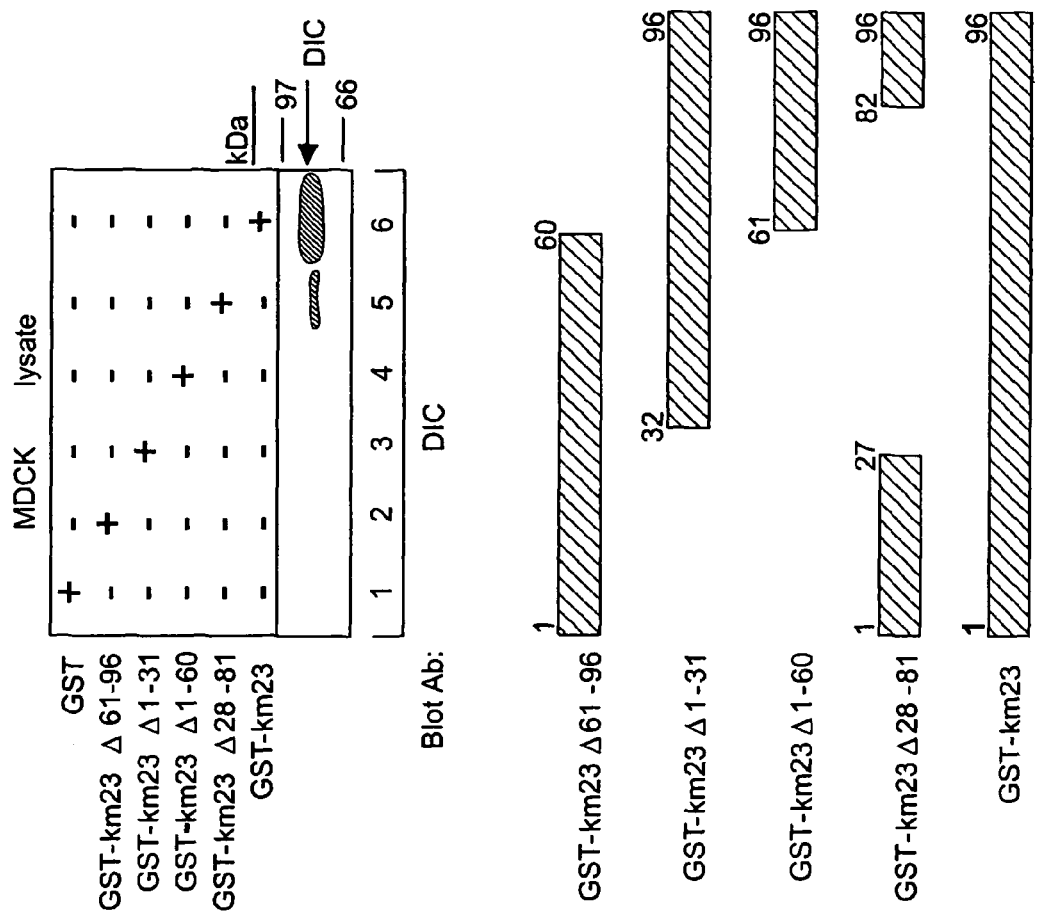
FIG. 14 is an immunoblot of the GST pull-down analysis of the interaction between DIC and GST fusions with wild-type km23 protein and km23 polypeptide fragments. The antibody used is anti-DIC. The GST fusions are depicted below according to km23 amino acid numbers.

Referring to FIG. 14, GST fusions with wild-type km23 and various fragments of km23 were expressed in MDCK cells. Cell lysates were subjected to immunoblot analysis using a monoclonal anti-DIC antibody, following GST pulldowns. As shown in this figure, expression of an altered form of km23, which lacked amino acids 28-81 in SEQ ID NO: 1 or SEQ ID NO: 2, (lane 5), lead to an aberrant interaction with DIC as compared to the wild-type protein (lane 6). The fragment in lane 5 corresponds to a *Drosophila* mutant, which has been shown previously to lead to an accumulation of intracellular cargoes and an increase in the mitotic index (Bowman et al., 1999). The *Drosophila* mutant is similar to the human spliced variant (truncated km23) shown in FIG. 8 of the present invention. This inventive km23 polypeptide fragment lacks amino acids 27-82 in SEQ ID NO: 1 or SEQ ID NO: 2 and behaves similarly. The weak binding of this inventive fragment will not permit appropriate attachment or movement of TGFβ signaling components, causing aberrant TGFβ signaling, and disrupting normal TGFβ responses.

The weak interaction with the GST km23Δ28-81 construct in lane 5 further indicates that both the C- and N-terminal ends of km23 are important for binding to the DIC of the multi-subunit dynein complex. Moreover, DIC does not appear to interact with either the C- or N-terminal ends of km23 alone. The inventor believes that km23 phosphorylation after TGFβ receptor activation causes a conformational change in km23, permitting interaction with DIC. This is further supported by the results in Example 12 below.

EXAMPLE 12

The Kinase Activity of TGFβ Receptor RII's Required for the Recruitment of km23 to the Dynein Intermediate Chain of the Dynein Multi-Subunit Complex With reference to the top panels of FIG. 15, MDCK cells (a TGFβ-responsive cell line) were transiently transfected with empty vector (EV), km23-Flag or km23-Flag and KN RII-HA (a kinase-deficient TGFβ receptor). Cells were treated with TGFβ for various times. Cell lysates were subjected to immunoprecipitation using a monoclonal anti-DIC antibody, followed by immunoblot analysis using anti-Flag. Western blot analysis for km23 and KN RII (lower panels) demonstrated equal protein expression and loading. These results demonstrated that the TGFβ-induced interaction between km23 and DIC was blocked when KN RII was expressed. This indicates that km23 phosphorylation by kinase-active TGFβ receptors is required for the recruitment of km23 to the dynein intermediate chain.

EXAMPLE 13 km23 Interacts with the TGFβ Signaling Component Smad2

Figure 7A:
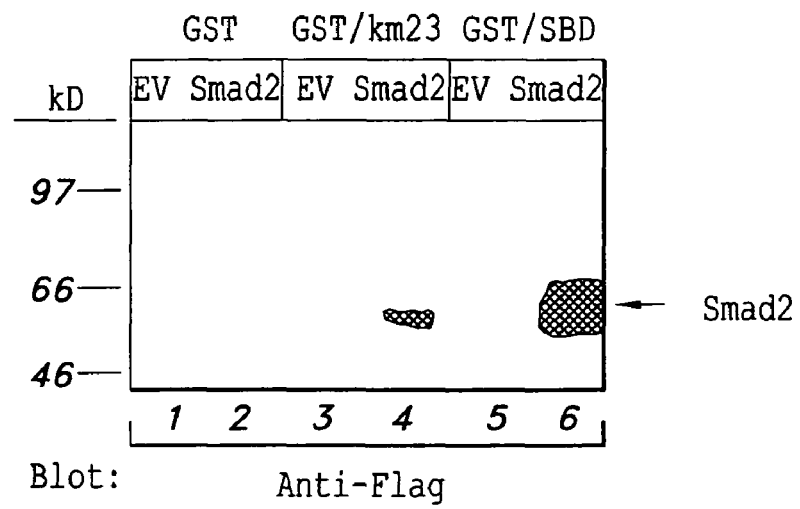
FIG. 7. km23 interacts with Smad2 via GST pull-down assay. 293T cells were transfected with Flag-tagged Smad2 and lysates were incubated with sepharose-bound bacterially expressed GST alone, GST-rkm23, or GST-SBD (Smad-binding domain of SARA, positive control). A: GST-bound proteins were analyzed by SDS-PAGE (10%) and were immunoblotted with an anti-flag Ab. Flag-tagged proteins were detected by ECL. Smad 2 interacts with GST-km23 and GST-SBD, but not with GST alone (control). Empty vector (EV) control lanes were also negative. B: Western blot analysis with an anti-Flag Ab to confirm expression of Smad2 in the relevant lanes (2, 4, 6). C: Coomassie staining of gel in A demonstrating the presence of GST and GST fusion proteins in the relevant lanes. The sizes are as expected for the different fusion proteins (approx. 37 kDa for GST-km23, approx. 35 kDa for GST-SBD) or GST alone (approx. 27 kDa).
Figure 7B:
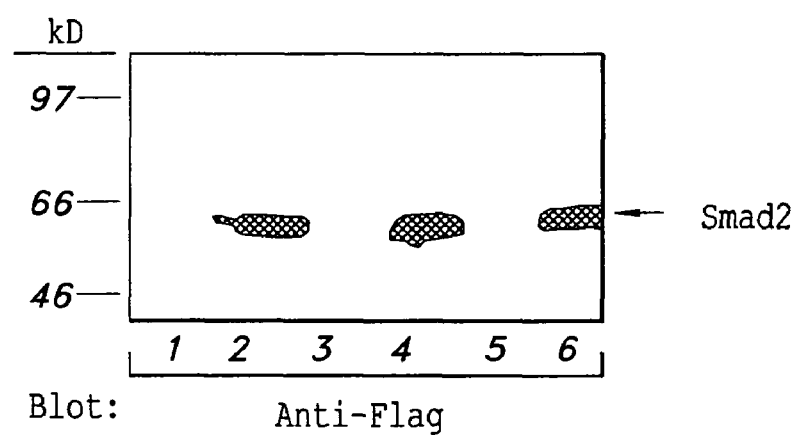
Figure 7C:
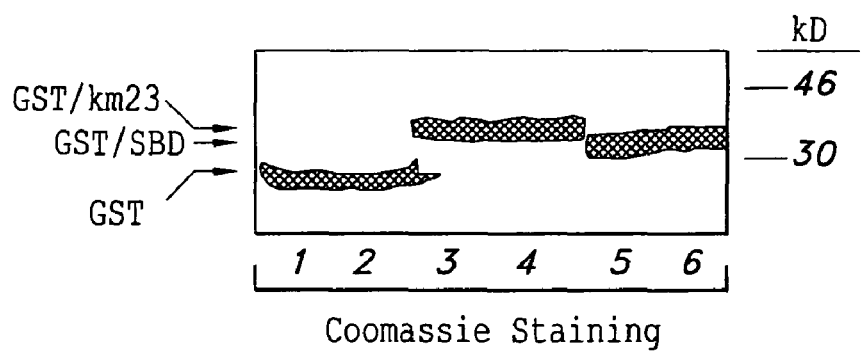

Referring to FIG. 7 (A-C), 293T cells were transfected with Flag-tagged Smad2 and lysates were incubated with sepharose-bound bacterially expressed GST alone, GST-rkm23, or GST-SBD (Smad-binding domain of SARA, positive control). A: GST-bound proteins were analyzed by SDS-PAGE (10%) and were immunoblotted with an anti-flag Ab. Flag-tagged proteins were detected by ECL. Smad 2 interacts with GST-km23 and GST-SBD, but not with GST alone (control). Empty vector (EV) control lanes were also negative. B: Western blot analysis with an anti-Flag Ab to confirm expression of Smad2 in the relevant lanes (2, 4, 6). C: Coomassie staining of gel in A demonstrating the presence of GST and GST fusion proteins in the relevant lanes (2,4,6). The sizes are as expected for the different fusion proteins (approx. 37 kDa for GST-km23, approx. 35 kDa for GST-SBD) or GST alone (approx. 27 kDa). These results demonstrate that km23 interacts with Smad2, a TGFβ superfamily member signaling component known to be important for some biological responses of TGFβ. This interaction was also verified by If/blot analysis. The interaction suggests that km23 can modulate Smad2 function in some way or vice versa.

EXAMPLE 14

Diagnostic/Prognostic Screening Methods of the Present Invention

H&E Staining

Sterile tissues were provided by Cooperative Human Tissue Network (CHTN, Eastern division, University of Pennsylvania) and were sent in dry ice and stored at −80° C. until use. H&E staining was essentially as described by Goldsworthy et al. (see Molecular Carcinogenesis 25:86-91, 1999).

Sections of frozen tissues (10 μm) were mounted on slides (SL Microtest, Germany), and fixed for 3 min in 70% ethanol. After fixation, the slides were rinsed in water for 15 s, then stained with Mayer's hematoxylin (Sigma) for 30 s, rinsed in water 10 seconds, and then treated with 1× Automation buffer (Biomeda Corp, Calif.) for 15 s. After another water rinse, the slides were dehydrated in 70% ethanol for 1 min and 95% with ethanol for 1 min, and then stained in eosin (Sigma) for 20 s. The slides were then cleared with changes of 95% ethanol for 1 min and 100% ethanol for 1 min, followed by xylene for 1 min, and air dried before LCM. All reagents for H&E staining were prepared with DEPC treated distilled water.

Laser Capture Microdissection (LCM)

LCM was performed using a μCut Laser Microdissection system (SL Microtest, Germany) according to the manufacturer's instructions. After microdissection of each specimen, the thermoplastic film-coated cap containing the captured tissue was placed in a 0.5 ml microtube.

RNA Isolation from Histologic Sections

RNA was isolated from a laser capture micro-dissected tissue using a Total RNA Microprep Kit (Stratagene, La Jolla, Calif., Cat# 400752), according to manufacturer's recommendations. The RNA was suspended in 30 μl of elution buffer and preserved at −80° C.

RNA Isolation from Cells

RNA was isolated from cell lines using Trizol reagent (Gibco) according to the manufacturer's suggestions.

RNA Isolation from Circulating Nucleic Acids in Plasma/Serum

The serum and plasma samples are collected in the same type of tubes used for DNA isolation from cnaps (described below). The blood is kept on ice following venipuncture and, within 30 min of collection, serum is separated by centrifugation at 1100×g for 10 min at 4 (degrees). Sera are then aliquoted and frozen at −70 (degrees) for storage until used. Care must be taken to minimize freeze-thaw cycles in order to minimize mRNA degradation. Serum RNA is harvested from 1.75-ml aliquots using the Perfect RNA Total RNA Isolation Kit (Five Prime-Three Prime, Boulder, Colo.), according to the instructions. Concentrations are determined by spectrophotometry. Additional details of the methodology may be found in Kopreski et al (Clin. Cancer Res 5: 1961-1965, 1999; Ann. NY Acad. Sci. 945: 172-178). Additional details related to plasma may be found in Lo et al (Clin Chem 45: 1292-1294, 1999).

Analysis of the Types and Frequency of km23 Alterations by Nested RT-PCR and DNA Sequencing RNA which was isolated from tissues, cell lines, or cnaps according to the methods above was employed as the reaction template for RT-PCR. cDNA synthesis was performed using Sensicript Reverse Transcriptase (QIAGEN, Germany, Cat# 205211) according to the manufacturer's recommendation. Nested PCR was performed using 2 pairs of primers spanning the whole open reading frame of hkm23. The forward primer of first round PCR was 5'-GTTTTGACAGAAAC-CTTTGCG-3' (SEQ ID NO: 20; spans nucleotides −85 to −65 of the 5'-untranslated region (UTR) in FIG. 12) and the reverse primer was 5'-TTGGTGCACA CAGGGGTTC-3' (SEQ ID NO: 21; spans nucleotides 451 to 469 of 3'-UTR in FIG. 12). The conditions used for the RT-PCR assay were: 94° C., 50 sec; 54° C., 50 sec; 72° C., 1 min; 30 cycles. The second round of PCR was performed using the first round PCR product as a reaction template. The forward primer for the second round was 5'-ACTCGCTAAGTGTTCGCTACG-3' (SEQ ID NO: 22; spans nucleotides −44 to −24 of 5'-UTR in FIG. 12) and the reverse primer was 5'-TGCCATGTGCTAGTC CACTGA, (SEQ ID NO: 23; spans nucleotides 360-380 of 3'-UTR in FIG. 12) with the following conditions: 94° C., 50 sec; 64° C., 50 sec; 72° C., 1 min; 30 cycles. The PCR products were electrophoresed on 2% agarose gels, visualized with ethidium bromide staining, purified using a QIAquick Gel Extraction Kit (QIAGEN, Germany, Cat# 28704), subcloned into pGEM-T easy vector (Promega, Madison, Wis., Cat#A1380), and finally sequenced using T7 and SP6 universal primers in both directions.

DNA Isolation from Histologic Sections

DNA was isolated from paraffin-embedded LCM tissues or, alternatively, from cnaps by the method described below. DNA in the paraffin-embedded LCM tissues was isolated in isolation buffer (10 mM TrisCl pH 8.0, 1 mM EDTA, 1% Tween 20, and 0.1 mg/ml proteinase K (Fisher Biotech, Fair Lawn, N.J., Cat# BP1700-100) as described by Emmert-Buck et al. in Science 274 (5289):921-922, 1996. Briefly, 20 µl of isolation buffer was added to the tissues, and the cells were covered and incubated at 37° C. overnight. After a brief centrifugation, the samples were heated to 95° C. for 8 min, and transferred to a new 0.5 ml tube after another brief centrifugation.

DNA Isolation from Cnaps

Blood Collection:

The serum samples are collected from the clinic using VACUTAINER brand no additive tubes with a red top (Becton Dickinson, L10263-00). The plasma samples are collected by the VACUTAINER CPT tube for plasma and mononuclear cells. (VACUTAINER CPT—Mononuclear Cell Preparation Tube from Becton Dickinson, Cat # 362761).

Blood Processing:

All of the following steps are performed in a hood dedicated for PCR.

Serum sample: The blood sample is left at 4° C. or room temperature (RT) for 2 hours and is then spun at 3000 rpm in a horizontal rotor at 1500-xg RCF for 3 minutes. Following centrifugation, the yellowish liquid is collected for serum.

Plasma samples: Peripheral blood (8 ml) is collected in a CPT tube and processed within 2 hours of collection. The blood sample is gently inverted 8 times. This is followed by centrifugation of the tube at RT for 20 minutes in a horizontal rotor at 1500-xg RCF.

Four layers should be visible in the tube after centrifugation of the serum or plasma samples: from top to bottom, they are (1) plasma, (2), lymphocytes & monocytes, (3) gel barrier, and (4) erythrocytes & neutrophils. Using a disposable transfer pipette, the upper plasma layer is removed without interrupting other layers.

DNA Extraction:

Serum or plasma (1.5 ml) is carefully transferred into a 50 ml centrifuge tube. Remaining serum or plasma is pipetted out and into a 1.8 ml Nunc CryoTube vials (Nunc Brand Products, Cat # 368632) and stored at −80° C. Next, 1.5 ml of 1×SDS proteinase K solution is added to the tube containing the serum or plasma and mixed well. The digestion occurs overnight at 55° C. in a water bath. There is total 3-ml of solution in each tube. Three ml of water saturated phenol/chloroform (PC-8) at room temperature is placed in each of 2 sets of SST Tubes labeled as "A" and "B" for each sample (VACUTAINER Brand SST Tubes with gel barrier Cat # 366510). The 3 ml of digested solution is decanted into the "A" set of the SST tubes with same label as the sample, Vortexed 30 seconds to mix well and centrifuged for 10 min at 2500 rpm using a horizontal rotor. After centrifuging, there are 3 phases in the tube which are (1) the organic phase at the bottom, (2) gel barrier in the middle, and (3) the upper liquid layer which contains the digested DNA. The upper liquid is poured into the "B" set of SST tubes containing PC-8 and the phenol/chloroform extraction procedure is repeated.

DNA Precipitation:

A fresh 50-ml centrifuge tube is prepared for each sample. The upper liquid from the "B" set is decanted after PC 8 extraction into the fresh 50 ml tube. In order, the following are added to the sample: 3-µl glycogen (Boehringer Mannheim, Cat #901393), 1 ml 7.5 M Ammonium acetate (Sigma, Cat # A2706), and 8 ml 100% ethanol. After capping the sample is mixed gently by inverting it several times. The tube is next centrifuged at 6000 rpm for 30-60 minutes. The supernatant is poured off carefully, keeping the pellet on the bottom of the tube. Ten ml of 70% ethanol is added into the tube and the tube is spun again at 6000 rpm for 10 minutes. After discarding the ethanol, the tube is spun again briefly and the remaining ethanol is pipetted out. The tube is left open in the hood to air-dry for 10 minutes. This is followed by the addition of 200 µl of LoTE buffer to resuspend DNA for about 2 hours or overnight at RT. The tube is then centrifuged briefly and the DNA solution is transferred into 1.5-ml eppendorf tubes and stored at −20° C. as the DNA stock solution. Typically 1-3 µl of the DNA samples is used in a 50 µl PCR reaction.

Determination of DNA Concentration:

Take 5-µl DNA stocks and add 95-µl distilled water in 0.5-µl tube, mix thoroughly. Next, pipet 100-µl mixture into a micro cell of a spectrometer and check for OD value at 260 nm, calculate the concentration of serum DNA according the following Formula:

The value of OD/260 nm×50 (DNA conversion factor)×20 (dilution factor)=Concentration of DNA in ng/µl Solutions:

10×SDS/Protein K:
Mix 20 ml Lauryl sulfate (SDS) 10% solution (Sigma, Cat # L-4522 for 100 ml/bottle) with one vial Proteinase K (100 mg) until dissolve. Aliquot into 1 ml each and store in a 1.5 ml tube at −20?C. Final concentration is 5 mg PK/ml 10% SDS.

1×1% SDS/protein K working solution:
Take 1 ml 10×SDS/PK stock and mix with 9 ml TE-9 buffer. Use fresh or store at −20?C. The final concentration is 1% SDS, 500 µg/ml PK:

TE-9:
500 mM Tris, 9.0 (Sigma T6003), 20 mM EDTA, and 10 mM NaCl.

LOTE:
30 mM Tris and 0.3 mM EDTA.

Analysis of Types and Frequency of km23 Alterations by Nested PCR and DNA Sequencing Nested PCR was used to amplify individual exons of the km23 gene. This method was performed using two pairs of primers spanning the second, third, or fourth exons of the hkm23 gene shown in FIG. 11 as indicated below. It was performed on (1) DNA which had been isolated from tissues following H & E staining and microdissection; or (2) DNA that had been extracted from serum and plasma samples using circulating nucleic acids in plasma/serum (cnaps). The first PCR round employs a genomic nucleic acid form (obtained from patient tissues or cnaps) as the reaction template to yield a first PCR product of the indicated size. The second PCR round employs the first PCR product as the reaction template to generate a second PCR product of the indicated size. The PCR products were purified by electrophoresis on agarose gels, and sequenced to identify alterations from the wild-type sequence of km23. Desired primers and PCR conditions are as follows:

Detection of mutations in exon 2 of the km23 gene:

First round PCR:

```
Forward primer (SEQ ID NO:12):
5'-TGC CAG GTG CCT GAG TAT TA-3'      (9766-9785)

Reverse primer (SEQ ID NO:13):
5'-GAT CAG ATT CAT GAA GGG CTT-3'     (10047-10067)
```

The length of PCR products is 302 base pairs.

| | | |
|---|---|---|
| 94° C. | 4 min | |
| 94° C. | 45 seconds | |
| 52° C. | 50 seconds | ] 35 cycles |
| 72° C. | 1 min | |
| 72° C. | 7 min | |

Second round PCR:

```
Forward primer (SEQ ID NO:14):
5'-CAA ACG TAT GAT TCA TCT GCC-3'     (9805-9825)

Reverse primer (SEQ ID NO:15):
5'-ATG CTG TGT TAT GGC TGC TT-3'      (10010-10029)
```

The length of PCR products is 225 base pairs.

| | | |
|---|---|---|
| 94° C. | 4 min | |
| 94° C. | 45 seconds | |
| 52° C. | 50 seconds | ] 35 cycles |
| 72° C. | 1 min | |
| 72° C. | 7 min | |

Detection of mutations in exon 3 of the km23 gene:

First round PCR:

```
Forward primer (SEQ ID NO:8):
5'-TGC TAT TCC AGT TCT CCC CAA-3'     (18157-18177)

Reverse primer (SEQ ID NO:9):
5'-ATC CTC TGG AGA CAC CAC TGT-3'     (18492-18512)
```

The length of PCR products is 356 base pairs.

| | | |
|---|---|---|
| 94° C. | 4 min | |
| 94° C. | 45 seconds | |
| 51° C. | 50 seconds | ] 35 cycles |
| 72° C. | 1 min | |
| 72° C. | 7 min | |

Second round PCR:

```
Forward primer (SEQ ID NO:10):
5'-TCC ACA TCC TCT CAG TCT CCG-3'     (18212-18232)

Reverse primer (SEQ ID NO:11):
5'-AAT GTG CCA TGA GGT CTG TTC-3'     (18445-18465)
```

The length of PCR products is 254 base pairs.

| | | |
|---|---|---|
| 94° C. | 4 min | |
| 94° C. | 45 seconds | |
| 53° C. | 50 seconds | ] 35 cycles |
| 72° C. | 1 min | |
| 72° C. | 7 min | |

Detection of mutations in exon 4 of the km23 gene:

First round PCR:

```
Forward primer (SEQ ID NO:16):
5'-ATT TGG AGA TGC TGA ACG TTG-3'     (24056-24075)

Reverse primer (SEQ ID NO:17):
5'-AAG CGA CTG CCA TGT GCT AGT-3'     (24321-24341)
```

The length of PCR products is 286 base pairs.

| | | |
|---|---|---|
| 94° C. | 4 min | |
| 94° C. | 45 seconds | |
| 54° C. | 50 seconds | ] 35 cycles |
| 72° C. | 1 min | |
| 72° C. | 7 min | |

Second round PCR:

```
Forward primer (SEQ ID NO:18):
5'-TGG TTT ATT TGC TTT CTT GTG-3'     (24127-24147)

Reverse primer (SEQ ID NO:19):
5'-AGT CCA CTG ACA TGA TTG ACA-3'     (24303-24323)
```

The length of PCR products is 197 base pairs

| | | |
|---|---|---|
| 94° C. | 4 min | |
| 94° C. | 45 seconds | |
| 50° C. | 50 seconds | ] 35 cycles |
| 72° C. | 1 min | |
| 72° C. | 7 min | |

The PCR products were electrophoresed in 2% agarose gels, and then were visualized with ethidium bromide staining. Next, they were purified using QIAquick Gel Extraction Kit (QIAGEN, Germany, Cat# 28704) and sequenced directly.

EXAMPLE 15

A km23 Mutant Form Blocks TGFβ Promoter Activity

A luciferase reporter assay was performed essentially as described previously (Lu, et al, 1998; Yue, et al. 1999 a; b) in Mv1Lu cells in the presence and absence of a mutant km23 polypeptide comprising a Val in place of Arg at the amino acid corresponding to amino acid 58 of SEQ ID NO: 1 or SEQ ID NO: 2 (i.e., R58V mutant). The effect of expression of this R58V mutant on the region of the $TGF\beta_1$ promoter responsible for $TGF\beta_1$ production was examined. This region was previously identified as an AP-1 site in the $TGF\beta_1$ promoter by the present inventor (see Yue and Mulder, J. Biol. Chem. 275:30765-30773, 2000). The luciferase reporter assay was performed using a region including this AP-1 site as the reporter. The data obtained from this reporter assay indicated that expression of the R58V mutant inhibited by 50% or more both basal and TGFβ-stimulated $TGF\beta_1$ promoter activity, indicating a role for km23 protein in TGFβ production.

The results indicate a role for wild-type km23 in TGFβ production in cells that are no longer growth inhibited by TGFβ. In these instances, a therapeutic agent would be sought which would be a mimetic of the R58V km23 mutant.

EXAMPLE 15.1

Stable Expression of km23 Activates Jun N-terminal Kinase (JNK) and Induces the Phosphorylated of c-Jun The inventor's previous results have indicated that TGFβ can induce a rapid activation of JNK and a rapid phosphorylation of the JNK downstream effector, c-Jun, events which are required for $TGF\beta_1$ production (Frey and Mulder, 1997; Yue and Mulder, 2000). The present example describes the use of the Mv1Lu cells, stably transfected with wild-type km23, or with empty vector (EV), as shown in FIG. 16. The cells were incubated in the presence of absence of TGFβ (10 ng/ml) for time periods varying from 0 to 30 min. Cell lysates were immunoprecipitated with an anti-JNK antibody (C-17), and subjected to in vitro kinase assays using GST-c-JUN (1-79) as the substrate. The phosphorylated proteins were resolved by SDS-PAGE. Normal rabbit IgG was used as the negative control and equal JNK and km23 expression was verified by blotting controls. Parallel samples were analyzed for phosphorylation of c-Jun via Western blotting using a phospho-c-Jun antibody.

The results (not shown) indicated the following: (1) when km23 was stably expressed in Mv1Lu cells, JNK was superactivated in the absence of TGFβ; (2) JNK activity was approximately 15 times greater in the km23-expressing cells than in the EV-expressing cells during the 2-10 min period after TGFβ addition; (3) expression of km23 induced phosphorylation of c-Jun as TGFβ does; (4) km23 can function as a signaling intermediate for TGFβ, leading to JNK activation and c-Jun phosphorylation; (5) since activation of JNK and c-Jun are generally required for activation of promoter regions containing AP-1 and CRE sites (the promoter regions important for production of the $TGF\beta_1$ isoform, and the $TGF\beta_2$ and $TGF\beta_3$ isoforms, respectively), this indicates that expression of km23 can also mediate TGFβ production.

EXAMPLE 16

Stable Expression of km23 Inhibits Cell Growth

With reference to FIG. 16, Mv1Lu cells were stably transfected with either empty vector (hatched bars) or GFP-km23-Flag (solid bars), were plated and analyzed using the Crystal Violet Assay (EM Science) described below. The results indicate that (1) stable expression of km23 results in approximately 50% inhibition of the growth of Mv1Lu cells; and (2) the expression of wild-type km23 results in growth inhibition of epithelial cells, as TGFβ does.

EXAMPLE 17

Screening for Therapeutic Agents Using a Cell-Based Assay for Detecting Growth Inhibition As shown in Example 16, km23 appears to function as a tumor suppressor, blocking cancer cell growth under normal conditions. In contrast, alterations in the km23 gene in epithelial cancers abrogate the tumor suppressive function of km23.

The present example describes a cell-based assay for screening to identify agents that restore the normal functions of km23 or replace the altered forms/functions of km23. Altered forms of km23 protein, as well as wild-type km23 are expressed using tet-inducible km23 expressing cells. These cells are developed using TGFβ-responsive MDCK cells or cancer cells. Agents are sought that either (1) restore the growth inhibition of km23 or, (2) block TGFβ production by interfering with wild-type km23's actions in this regard (see Example 15 and 15.1); blocking TGFβ production would be useful in cases where tumors are no longer inhibited by TGFβ, and TGFβ leads to immunosuppression and tumor spread.

The crystal violet assay is used to assess cell growth in the presence and absence of therapeutic candidates. Dose-response assays will be performed to determine effective amounts of the therapeutic agents. The crystal violet assay allows one to obtain quantitative information about the relative density of cells adhering to multi-well cluster dishes. The dye in this assay, crystal violet, stains DNA. Upon solubilization, the amount of dye taken up by the monolayer can be quantified in a spectrophotometer or plate reader. This method is described in the following reference: Tang, Q., Staub, C. M., Gao, G., Jin, Q., Wang, Z., Ding, W., Aurigemma, R. E., and Mulder, K. M. A TGFβ receptor-interacting protein that is also a light chain of the motor protein dynein. Molec. Biol. of the Cell, *In Press*, 2002. Further details of the protocol can be found at http://www-ufk.med.uni-rostock.de/lablinks/protocols/e_protocols/cvassay.htm.

EXAMPLE 18

Screening for Therapeutic Agents Using Fluorescence Resonance Energy Transfer (Fret)

Fluorescence resonance energy transfer (FRET) is a quantum mechanical process wherein excitation energy is transferred from a donor fluorophore to an appropriately positioned acceptor positioned acceptor fluorophore without emission of a photon. Energy can be transferred this way only over a very limited distance, and the efficiency of the energy transfer varies inversely with the sixth power of the distance separating the donor and acceptor fluorophores, effectively limiting FRET to a range of 0.002-0.01 um (Forster, T. in Modern Quantum Chemistry (Sinanglu, O., Ed.), Vol. 3, pp.

93-137, Academic Press, New York, 1965; Wu, P. and Brand, L, Anal. Biochem. 218:1-13, 1994). FRET has been used for measuring the distances between interacting molecules under physiological conditions with near angstrom resolution (Selvin, P. R., Meth. Enzymol. 246:300-334, 1995). It is highly sensitive, specific, and flexible. These conditions must be met for FRET to occur. First, the donor emission spectrum must significantly overlap the absorption spectrum of the acceptor. Second, the distance between the donor and the acceptor fluorophores must fall within the range of 2-10 nm. Third, the donor and acceptor fluorophores must be in a favorable mutual orientation (Day et al, Methods. 25:4-18, 2001). One of the most important uses of FRET spectroscopy is to study protein-protein interactions. Structural information is not required to measure the binding proximity of two components (Rye, H. S., Methods. 24:278-288, 2001).

As described by Tang, et al, km23 is both a TGFβ receptor-interacting protein, as well as a light chain of the motor protein dynein (see Tang, Q., Staub, C. M., Gao, G., Jin, Q., Wang, Z., Ding, W., Aurigemma, R. E., and Mulder, K. M. A TGFβ_receptor-interacting protein that is also a light chain of the motor protein dynein, Molec. Biol. of the Cell, In Press, 2002.) The present inventor has determined that km23 interacts with the dynein intermediate chain of the motor protein dynein. The present inventor has also determined that a spliced variant of km23 binds weakly to DIC, as compared to the wild-type km23 protein (see Example 11). This inventive polypeptide comprises SEQ ID NO: 1 or 2, except that it lacks amino acids 27-82 in SEQ ID NO: 1 or 2. Since this truncated km23 polypeptide was found in 2 out of 6 ovarian cancer samples, it provides evidence that alterations in the normal interaction between km23 and DIC may lead to cancer. Therefore, a therapeutic agent would be sought which would be capable of altering the interaction of km23 forms with the dynein intermediate chain.

A useful strategy to screen for therapeutics involves the use of the purified recombinant GST-km23 protein forms (including wild-type, mutant, and truncated km23 polypeptide forms) in conjunction with GST-DIC forms. These fusion proteins will be used to perform FRET spectroscopy (Matyus, L., J. Photochem. Photobiol. B 12(4):323-337, 1992). The fusion proteins are purified from mammalian or bacterial cells using GST pulldowns, or other tag-related methods.

Figure 17:
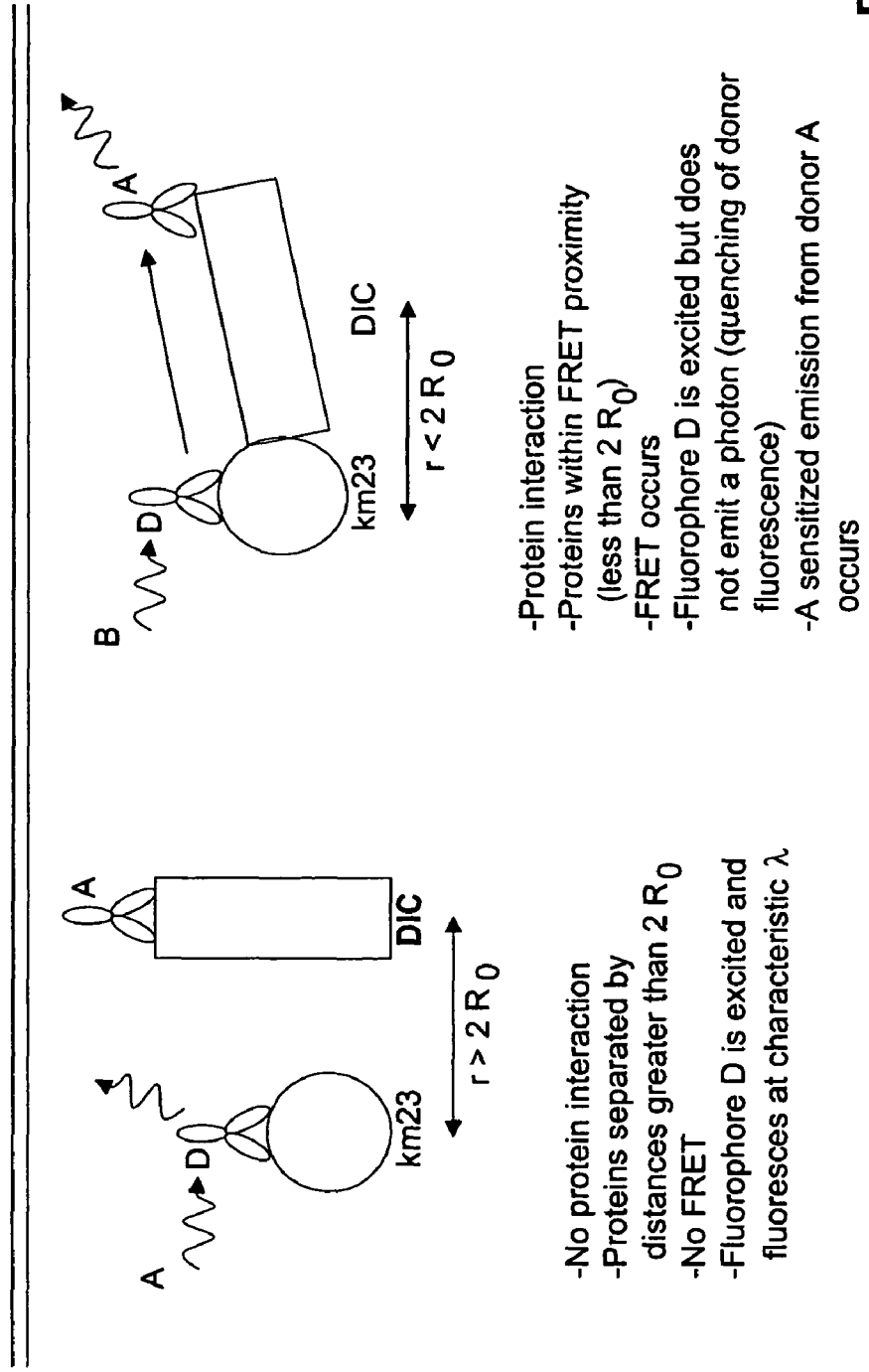
FIG. 17 is a schematic representation of a fluorescence resonance energy transfer (FRET) assay useful for screening for therapeutic agents which affect the protein interaction between km23 and DIC.

Based on the regions of interaction of other dynein light chains (DLCs) with DIC, various truncation mutants of DIC are used. Full-length DIC is also used. For these studies, Alexa Fluors 555 and 488 available from Molecular Probes (Eugene, Oreg.) are useful fluorophores. Alexa Fluor 488 is the best fluorescein substitute available for this type of assay; it has strong absorption, and an extinction coefficient greater than 65,000 per cm per M, and it is more photostable than fluorescein, allowing more time for observation and image capture. Similarly, the Alexa Fluor 555 dye is a match to the spectra of the Cy3 dye, with an extinction coefficient of greater than 150,000 per cm per M. Protein labeling kits to conjugate the dye to the proteins of interest (in this case to various forms of each of km23 and DIC) are also available from Molecular Probes (http://wwwprobes.com/handbook/bpxes/0422.html). The basis for the FRET spectroscopy studies is depicted in FIG. 17. The FRET analyses are performed in microplate formats. This type of protein-protein interaction screen is highly amenable to the development of platform screens to identify agents that can modify defective interactions to accomplish the desired outcome. The benefits of FRET microplate assays are significant, since an action-specific signal is generated, and detection above background is improved.

The effect of the test compound on the protein-protein interaction is detected by comparing the fluorescence spectra for each fluorescently labeled polypeptide in the absence and presence of the test compound, wherein the fluorophore is the label. In particular, an interaction is detected by observing a decrease in the fluorescence spectra of the donor and an increase in the fluorescence spectra of the acceptor as shown in FIG. 17. This will occur only when the proteins interact. Therefore, the spectra are different when the proteins are not interacting than when they interact. A drug candidate could block, enhance, or modulate this protein interaction.

Small molecular weight compounds or peptides are useful if they can inhibit the interactions of mutant and truncated km23 polypeptide forms with DIC, assuming that a sufficient amount of km23 is still available in the cell to interact with DIC appropriately.

As provided in Example 15 and 15.1, the present inventor has evidence linking km23 to the production of TGFβ. Therefore, in instances where tumors are no longer inhibited by TGFβ, it would be desirable to block the wild-type km23-DIC interactions to block TGFβ production in such tumors. For example, a desirable therapeutic agent in this case would be a mimetic of the R58V mutant km23 form described in Example 15.

LIST OF REFERENCES

1. Ausubel, F. M., et al. (1992), Current Protocols in Molecular Biology, (John Wiley and Sons, New York, N.Y.)
2. Bassing, C. H., Yingling, J. M., Howe, D. J., Wang, T., He, W. W., Gustafson, M. L., Shah, P., Donahoe, P. K., and Wang, X.-F. (1994) A transforming growth factor β type I receptor that signals to activate gene expression. Science 263:87-89.
3. Bilder, D., Li, M., and Perrimon, N. (2000) Cooperative regulation of cell polarity and growth by Drosophila tumor suppressors. Science 289:113-116.
4. Bowman, A. B., Patel-King, R. S., Benashski, S. E., McCaffery, J. M., Goldstein, L. S. B., and King, S. M. (1999) Drosophila roadlbock and Chlamydomonas LC7: A conserved family of dynein-associated proteins involved in axonal transport, flagellar motility, and mitosis. J. Cell Biol. 146:165-179.
5. Buard, A., Zipfel, P. A., Frey, R. S., and Mulder, K. M. (1996) Maintenance of growth factor signaling through Ras in human colon carcinoma cells containing K-ras mutations. Int. J. Cancer 67:539-546.
6. Carabatsos, M. J., Elvin, J., Matzuk, M. M., and Albertini, D. F. (1998) Characterization of oocyte and follicle development in growth differentiation factor-9-deficient mice. Dev. Biol. 204(2):373-384.
7. Charng, M.-J., Zhang, D., Kinnunen, P., and Schneider, M. D. (1998) A novel protein distinguishes between quiescent and activated forms of the type I transforming growth factor β receptor. J. Biol. Chem. 273:9365-9368.
8. Chirgwin, J. M., Przybyla, A. E., MacDonald, R. J., and Rutter, W. G. (1979) Isolation of biologically active ribonucleic acid from sources enriched in ribonuclease. Biochemistry 18:5294-5299.
9. Datta, P. K., Chytil, A., Gorska, A. E., and Moses, H. L. (1998) Identification of STRAP, a novel WD domain protein in transforming growth factor-β signaling. J. Biol. Chem. 273:34671-34674.
10. Dong, C., Li, Z., Alvarez, R., Jr., Feng, X.-H., and Goldschmidt-Clermont, P. J. (2000) Microtubule binding to Smads may regulate TGFβ activity. Molecular Cell 5:27-34.

11. Frey, R. S. and Mulder, K. M. (1997a) Involvement of ERK2 and SAPK/JNK activation by TGFβ in the negative growth control of breast cancer cells. Cancer Res. 57:628-633.
12. Griswold-Prenner, I., Kamibayashi, C., Maruoka, E. M., Mumby, M. C. and Derynck, R. (1998) Physical and functional interactions between type I transforming growth factor β receptors and Bα, a WD-40 repeat subunit of phosphatase 2A. Mol. Cell. Biol. 18:6595-6604.
13. Hartsough, M. E. and Mulder, K. M. (1995) Transforming growth factor β activation of p44$^{mapk}$ in proliferating cultures of epithelial cells. J. Biol. Chem. 270:7117-7124.
14. Hartsough, M. T., Frey, R. S., Zipfel, P. A., Buard, A., Cook, S. J., McCormick, F. and Mulder, K. M. (1996) Altered TGFβ signaling in epithelial cells when Ras activation is blocked. J. Biol. Chem. 271:22368-22375.
15. Hartsough, M. E., and Mulder, K. M. (1997) Transforming growth factor-β signaling in epithelial cells. Pharmacol. Ther. 75:21-41.
16. Hata, A., Seoane, J., Lagna, G., Montalvo, E., Hemmati-Brivanlou, A., and Massague, J. (2000) OAZ uses distinct DNA- and protein-binding zinc fingers in separate BMP-Smad and olf signaling pathways. Cell 100:229-240.
17. Hirokawa, N. (1998) Kinesin and dynein superfamily proteins and the mechanism of organelle transport. Science 279:519-526.
18. Höfer, D., Jöns, T., Kraemer, J., and Drenckhahn, D. (1998) From cytoskeleton to polarity and chemoreception in the gut epithelium. Ann N Y Acad. Sci. 859:75-84.
19. Kawabata, M., Imamura, T., Miyazono, K., Engel, M. E., and Moses, H. L. (1995) Interaction of the transforming growth factor-β type I receptor with farnesyl-protein transferase-α. J. Biol. Chem. 270:29628-29631.
20. Kim, S-J., Im, Y.-H., Markowitz, S. D., and Bang, Y.-J. (2000) Molecular mechanisms of inactivation of TGF-β receptors during carcinogenesis. Cytokine & Growth Factor Reviews 11: 159-168.
21. King, S. M. (2000) The dynein microtubule motor. Biochimica et Biophysica Acta 1496:60-75.
22. Knudson, A. G., (1993) Nature Genet. 5:103.
23. Lipshitz, H. D., Peattie, D. A., and Hogness, D. S. (1987) Novel transcripts from the *Ultrabithorax* domain of the bithorax complex. Genes & Development 1:307-322.
24. Liu, X., Yue, J., Frey, R. S., Zhu, Q. and Mulder, K. M. (1998) TGFβ signaling through Smad1 in human breast cancer cells. Cancer Res. 58:4752-4757.
25. Markowitz, S., Wang, J. Myeroff, L., Parsons, R., Sun, L., Lutterbaugh, J., Fan, R. S., Zboroska, E., Kinzler, K., Volgelstein, B., Brattain, M., and Willson, J. K. (1995) Inactivation of the Type II TGF-β receptor in colon cancer cells with microsatellite instability. Science 268:1336-1338.
26. Massagué, J. (1998) TGF-β signal transduction. Annu. Rev. Biochem. 67:753-791.
27. Massagué, J. and Chen, Y.-G. (2000) Controlling TGF-β signaling. Genes & Development 14:627-644.
28. Milisav, I. (1998) Dynein and dynein-related genes. Cell Motility and the Cytoskeleton 39:261-272.
29. Miyazono, K. (2000) TGF-β signaling by Smad proteins. Cytokine & Growth Factor Reviews 11:15-22.
30. Morata, G. and Kerridge, S. (1981) Sequential functions of the bithorax complex of *Drosophila*. Nature 290:778-781.
31. Mulder, K. M. and Morris, S. L. (1992) Activation of p21ras by transforming growth factor β in epithelial cells. J. Biol. Chem. 267:5029-5031.
32. Mulder, K. M., Segarini, P. R., Morris, S. L., Ziman, J. M., and Choi, H. G. (1993) Role of receptor complexes in resistance or sensitivity to growth inhibition by TGFβ in intestinal epithelial cell clones. J. Cell. Phys. 154:162-174.
33. Reddy, K. B., Karode, M. C., Harmony, J. A. K., and Howe, P. H. (1996) Interaction of transforming growth factor β receptors with apolipoprotein J/clusterin. Biochemistry 35:309-314.
34. Sambrook, J., et al. (1989), Molecular cloning: A laboratory manual, 2$^{nd}$ Ed. (Cold Spring Harbor Laboratory, Cold Spring Harbor, N.Y.).
35. Skolnik, E. Y., Margolis, B., Mohammadi, M., Lowenstein, E., Fischer, R., Drepps, A., Ullrich, A., and Schlessinger, J. (1991) Cloning of PI3 kinase-associated p85 utilizing a novel method for expression/cloning of target proteins for receptor tyrosine kinases. Cell 65:83-90.
36. Smolik-Utlaut, S. M., (1990) Dosage requirements of *Ultrabithorax* and *bithoraxoid* in the determination of segment identity of *Drosophila* melanogaster. Genetics 124: 357-366.
37. Sporn, M. B., Roberts, A. B., Wakefield, L. M., and de Crombrugghe, B. (1987) Some recent advances in the chemistry and biology of transforming growth factor-beta. J. Cell. Biol. 105:1039-1045.
38. Sporn, M. B. and Vilcek, J. T., eds. Cytokine and Growth Factor Reviews—TGFβ Special Issue 11:1-168, 2000.
39. Stern, D. L., A role of Ultrabithorax in morphological differences between *Drosophila* species, Nature 396: 463-466, 1998.
40. Tsukazaki, T., Chiang, T. A., Davison, A. F., Attisano, L. and Wrana, J. L. (1998) SARA, a FYVE domain protein that recruits Smad2 to the TGFβ receptor. Cell 95:779-791.
41. Ventura, F., Liu, F., Doody, J., and Massague, J. (1996) Interaction of transforming growth factor-β receptor I with farnesyl-protein transferase-α in yeast and mammalian cells. J. Biol. Chem. 271:13931-13934.
42. Wakefield, L. M., Smith, D. M., Masui, T., Harris, C. C., and Sporn, M. B. (1987) Distribution and modulation of the cellular receptor for transforming growth factor-beta. J. Cell. Biol. 105:965-975.
43. Wrana, J. L., Attisano, L., Wieser, R., Ventura, F., and Massagué, J. (1994) Mechanism of activation of the TGFβ-receptor. Nature 370:341-346.
44. Wrana, J. L. and Attisano, L. (2000) The Smad pathway. Cytokine & Growth Factor Reviews 11:5-13.
45. Yue, J., Buard, A., and Mulder, K. M. (1998) Blockade of TGFβ up-regulation of p27$^{Kip1}$ and p21$^{Cip1}$ by expression of RasN17 in epithelial cells. Oncogene 17:47-55.
46. Yue, J., Mulder, K. M. TGFβ Signal Transduction in Epithelial Cells. Pharmacol. Ther., *In Press*, 2001.
47. Yue, J., Frey, R. S. Hartsough, M. T., Frielle, T., and Mulder, K. M. (1999a) Cloning and expression of a rat Smad1: Regulation by TGFβ and modulation by the Ras/MEK pathways. J. Cell. Physiol. 178:387-396.
48. Yue, J., Frey, R. S., and Mulder, K. M. (1999b) Cross-talk between the Smad1 and Ras/MEK signaling pathways for TGFβ. Oncogene 18:2033-2037.
49. Yue, J. and Mulder, K. M. (2000) Requirement of Ras/MAPK pathway activation by TGFβ for TGFβ$_1$ production in a Smad-dependent pathway. J. Biol. Chem. 275:30765-30773.
50. Zhou, G. H. K., Sechrist, G. L., Brattain, M. G., and Mulder, K. M. (1995) Clonal heterogeneity of the sensitivity of human colon carcinoma cell lines to TGFβ isoforms. J. Cell. Physiol. 165:512-520.

What is claimed is:

1. A method for identifying therapeutic agents that inhibit, potentiate or mimic the ability of a km23 polypeptide mutant form, or a nucleic acid encoding the polypeptide mutant form to modulate a signal transduction activity of a growth factor or cytokine, the method comprising:
   (i) treating a cell with an effective amount of at least one candidate so as to alter at least one of the group consisting of regulation of gene expression, cell growth, cell differentiation, cell survival, apoptosis, senescence, cell migration, angiogenesis, fibrosis, extracellular matrix induction, adhesion, autoproduction and combinations thereof; and
   (ii) measuring the effect of the candidate on the cell;
   wherein said mutant form modulates TGFβ signaling events or dynein intermediate chain (DIC) binding activity and is a km23 polypeptide comprising SEQ ID NO: 1, except that the polypeptide lacks amino acids corresponding to amino acids 27-82 in SEQ ID NO: 1.

2. A method for identifying therapeutic agents that inhibit, potentiate or mimic the ability of a km23 polypeptide mutant form, or a nucleic acid encoding the polypeptide mutant form to modulate a signal transduction activity of a growth factor or cytokine, the method comprising:
   (i) treating a cell with an effective amount of at least one candidate so as to alter at least one of the group consisting of actin cytoskeleton dynamics, microtubule dynamics, intracellular transport, cell polarity, dynein-mediated microtubule transport and combinations thereof; and
   (ii) measuring the effect of the candidate on the cell;
   wherein said mutant form modulates TGFβ signaling events or dynein intermediate chain (DIC) binding activity and is a km23 polypeptide comprising SEQ ID NO: 1, except that the polypeptide lacks amino acids corresponding to amino acids 27-82 in SEQ ID NO: 1.

* * * * *